(12) United States Patent
Campbell et al.

(10) Patent No.: US 8,716,469 B2
(45) Date of Patent: May 6, 2014

(54) SYNTHETIC OLIGOSACCHARIDES FOR MORAXELLA VACCINE

(75) Inventors: A. Stewart Campbell, Framingham, MA (US); Gregory Lohman, Cambridge, MA (US); Obadiah J. Plante, Danvers, MA (US)

(73) Assignee: Ancora Pharmaceuticals, Inc., Woburn, MA (US)

( * ) Notice: Subject to any disclaimer, the term of this patent is extended or adjusted under 35 U.S.C. 154(b) by 0 days.

(21) Appl. No.: 13/643,184

(22) PCT Filed: Apr. 27, 2011

(86) PCT No.: PCT/US2011/034172
§ 371 (c)(1),
(2), (4) Date: Jan. 11, 2013

(87) PCT Pub. No.: WO2011/137181
PCT Pub. Date: Nov. 3, 2011

(65) Prior Publication Data
US 2013/0102759 A1    Apr. 25, 2013

Related U.S. Application Data

(60) Provisional application No. 61/328,576, filed on Apr. 27, 2010.

(51) Int. Cl.
*C07H 3/06* (2006.01)
*A61K 31/715* (2006.01)
*A61K 31/70* (2006.01)

(52) U.S. Cl.
USPC ............ 536/123.1; 536/4.1; 514/54; 514/25; 514/23; 530/350

(58) Field of Classification Search
USPC ........ 536/123.1, 4.1; 514/54, 25, 23; 530/350
See application file for complete search history.

(56) References Cited

PUBLICATIONS

Ekelof et al. (Carbohydrate Research 278 (1995) 289-300).*

* cited by examiner

*Primary Examiner* — Shaojia Anna Jiang
*Assistant Examiner* — Michael C Henry
(74) *Attorney, Agent, or Firm* — Brinks Gilson & Lione

(57) ABSTRACT

The present invention provides synthetic *Moraxella catarrhalis* lipooligosaccharide (LOS)-based oligosaccharides and conjugates containing various *M. catarrhalis* serotype-specific oligosaccharide antigens or various core *M. catarrhalis* oligosaccharide structures or motifs corresponding to one or more of the three major serotypes and/or members within a given serotype. The oligosaccharides may be synthesized by a chemical assembly methodology relying on a limited number of monosaccharide and disaccharide building blocks. The invention further provides *M. catarrhalis* LOS-based immunogenic and immuno-protective compositions and antibodies derived therefrom for diagnosing, treating, and preventing infections caused by *M. catarrhalis*.

25 Claims, 22 Drawing Sheets

| serot. | # | α-chain | β-chain |
|---|---|---|---|
| A | 27 | α-Gal-(1→4)-β-Gal-(1→4)-α-Glc-(1→2)-β-Glc | α-GlcNAc(1→2)-β-Glc |
| B6 |  | α-Glc-(1→2)-β-Glc | β-Glc |
| B7 | 8 | α-Glc-(1→2)-β-Glc | α-Glc-(1→2)-β-Glc |
| B8 |  | α-Glc-(1→2)-β-Glc | β-Gal-(1→4)-α-Glc-(1→2)-β-Glc |
| B9 | 11 | β-Gal-(1→4)-α-Glc-(1→2)-β-Glc | β-Gal-(1→4)-α-Glc-(1→2)-β-Glc |
| B10 |  | α-Gal-(1→4)-β-Gal-(1→4)-α-Glc-(1→2)-β-Glc | β-Gal-(1→4)-α-Glc-(1→2)-β-Glc |
| B11 | 20 | α-Gal-(1→4)-β-Gal-(1→4)-α-Glc-(1→2)-β-Glc | α-Gal-(1→4)-β-Gal-(1→4)-α-Glc-(1→2)-β-Glc |
| C8 |  | α-Glc-(1→2)-β-Glc | β-Gal-(1→4)-α-GlcNAc(1→2)-β-Glc |
| C10 |  | α-Gal-(1→4)-β-Gal-(1→4)-α-Glc-(1→2)-β-Glc | β-Gal-(1→4)-α-GlcNAc(1→2)-β-Glc |
| C11 | 37 | α-Gal-(1→4)-β-Gal-(1→4)-α-Glc-(1→2)-β-Glc | α-Gal-(1→4)-β-Gal-(1→4)-α-GlcNAc(1→2)-β-Glc |
| C11 frag | 40 | β-Glc | α-Gal-(1→4)-β-Gal-(1→4)-α-GlcNAc(1→2)-β-Glc |

FIG. 2

SYNTHETIC OLIGOSACCHARIDES FOR MORAXELLA VACCINE

This application is a National Stage application of International Application No. PCT/US2011/034172, filed Apr. 27, 2011, which claims the benefit of U.S. Provisional Application No. 61/328,576, filed Apr. 27, 2010.

FIELD OF THE INVENTION

The present invention relates to immunogenic and immunoprotective compositions and methods for making and using homogenous synthetic *Moraxella catarrhalis* lipooligosaccharide (LOS)-based oligosaccharides, conjugates, and antibodies derived therefrom.

BACKGROUND

*M. catarrhalis* is an important human mucosal pathogen that contributes to otitis media in infants and exacerbates conditions such as chronic obstructive pulmonary disease in the elderly. In view of the increased incidence of *M. catarrhalis* infection and increased virulence and antibiotic resistance found in modern clinical isolates, there is a need to identify and develop new therapies targeting this pathogen. Currently, there is no *M. catarrhalis* vaccine approved for human use.

The lipooligosaccharides (LOS) of *M. catarrhalis* share a high degree of structural homology across the three known serotypes (A, B and C), including a common glucose core, indicating the potential for broad based coverage if an antibody response to a common epitope can be elicited.

The present invention provides a synthetically produced vaccine approach targeting the LOS cores of *M. catarrhalis*. Native *M. catarrhalis* LOSs are composed of branched oligosaccharides anchored to the cell membrane via a $KDO_2$-lipid A linker. The $KDO_2$-lipid A glycolipid motif is found in many species of gram negative bacteria (Edebrink et al., *Carbohydr. Res.*, 295:127-146, 1996).

There is evidence that an antibody response to the LOS is a major part of the natural human immune response and that the anti-LOS antibodies from exposed patients are bactericidal to all the *M. catarrhalis* serotypes (U.S. Pat. No. 6,685,949). Monoclonal antibodies derived from animals exposed to killed *M. catarrhalis* are able to bind to all three serotype LOS structures equally well and display bactericidal activity towards all (Gergova et al., *Curr. Microbiol.*, 54:85, 2007). These antibodies are thought to bind to an LOS core structure shared by all three serotypes. These results suggest that it should be possible to elicit an immunogenic response against all three serotypes using an antigen composed of the *M. catarrhalis* LOS core or derivative thereof.

LOS preparations isolated and purified from cellular material have been shown to be lethal to mice (Fomsgaard et al., *Infect. Immun.*, 66:1891, 1998). The toxicity of the LOS preparations has been attributed to the $KDO_2$-lipid A motif, more specifically the lipid A component. Id. Several groups have tried to remove the lipid A portion from the isolated molecules (Gu et al., *Infect. Immun.*, 66:1891, 1998; Yu et al., *Infect. Immun.*, 73:2790, 2005; Yu et al., *Infect. Immun.*, 75:2974, 2007; U.S. Pat. No. 6,685,949). However, these methods do not completely and consistently remove the toxic lipid A portion.

The present invention provides synthetic *M. catarrhalis* LOS cores that are free of the $KDO_2$-lipid A moiety and are homogenous. Such synthetic cores of *M. catarrhalis* LOS provide several benefits for vaccine development. The present invention allows for the production of homogenous antigen compositions at high purity and at robust levels without contaminating carbohydrate structures that are an almost inevitable consequence of isolation from biological mixtures.

These synthetic oligosaccharide cores may include a linker to conveniently facilitate formation of conjugate molecules. These synthetic oligosaccharide cores can be modified in ways not possible with isolates from natural sources, i.e., by systematically varying length and composition, by functionalizing side chains, and by controlling the antigen-protein carrier conjugation ratio, etc. This enables ready access to minor sequences, deletion sequences, and other variants on the natural structures that would be difficult or impossible to obtain from natural sources in high purity and sufficient quantity for conjugation.

SUMMARY

The present invention provides synthetic oligosaccharides 1a:

where each of $R^1$ and $R^2$ is independently H, a monosaccharide or an oligosaccharide, and X is H or a protecting group. Oligosaccharides 1a include core oligosaccharides shared by the three *M. catarrhalis* serotypes.

The present invention further provides antigens 1b:

where each of $R^1$ and $R^2$ is independently H, a monosaccharide or a oligosaccharide; L is a linker; and Y is H or a carrier. Preferably, the antigens are free of endotoxins.

The present invention also includes compositions comprising an antigen 1b and a pharmaceutically acceptable vehicle. Preferably the composition contains a single antigen or a known, defined mixture of antigens.

The invention further provides vaccine compositions, including immunogenic and immunoprotective compositions, comprising antigen 1b and a pharmaceutically acceptable vehicle. These vaccine compositions can optionally include a pharmaceutically acceptable adjuvant. Preferably, the vaccine compositions are endotoxin-free. The vaccine compositions can be mono-, di-, tri- or tetravalent.

The invention further provides a method for synthetically forming oligosaccharides 1a and antigens 1b.

The invention further provides methods for diagnosing, treating, and preventing infections caused by *M. catarrhalis*.

BRIEF DESCRIPTION OF THE DRAWINGS

FIG. 2 depicts the α and β chains of the naturally occurring *M. catarrhalis* LOS structures shown in FIG. 1. The shaded entries are the most common sequence found in each serotype; the other entries correspond to sequences found as lesser components in LOS fractions and to exemplary core oligosaccharides or motifs corresponding to one or more of the three major serotypes and/or members within a given serotype.

DETAILED DESCRIPTION

Definitions

Figure 1:
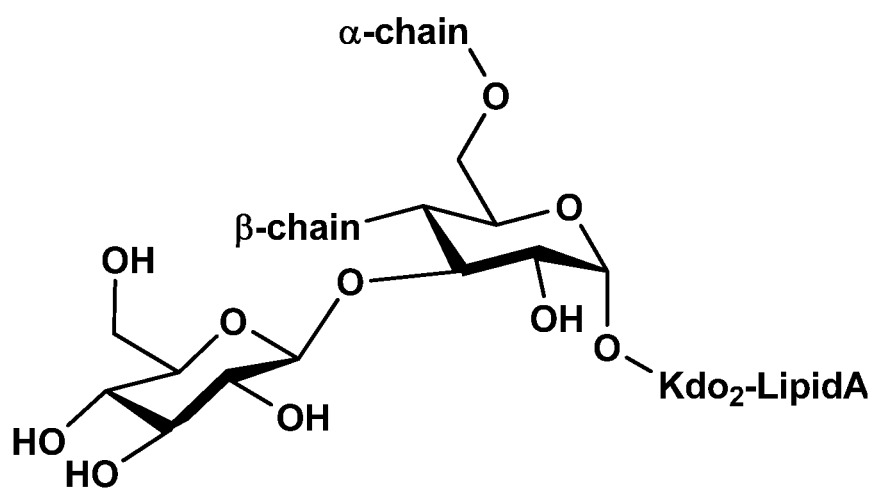
FIG. 1 depicts LOS structures shared by the three *M. catarrhalis* serotypes, which contain a common, highly branched glucose core and a $KDO_2$-lipid A motif at the reducing end. Structural variance can be found in the α and β chains. While all three serotypes are comprised of glucose and galactose residues, the A and C serotypes also contain an N-acetyl glucosamine in the β chain.
Figure 3:
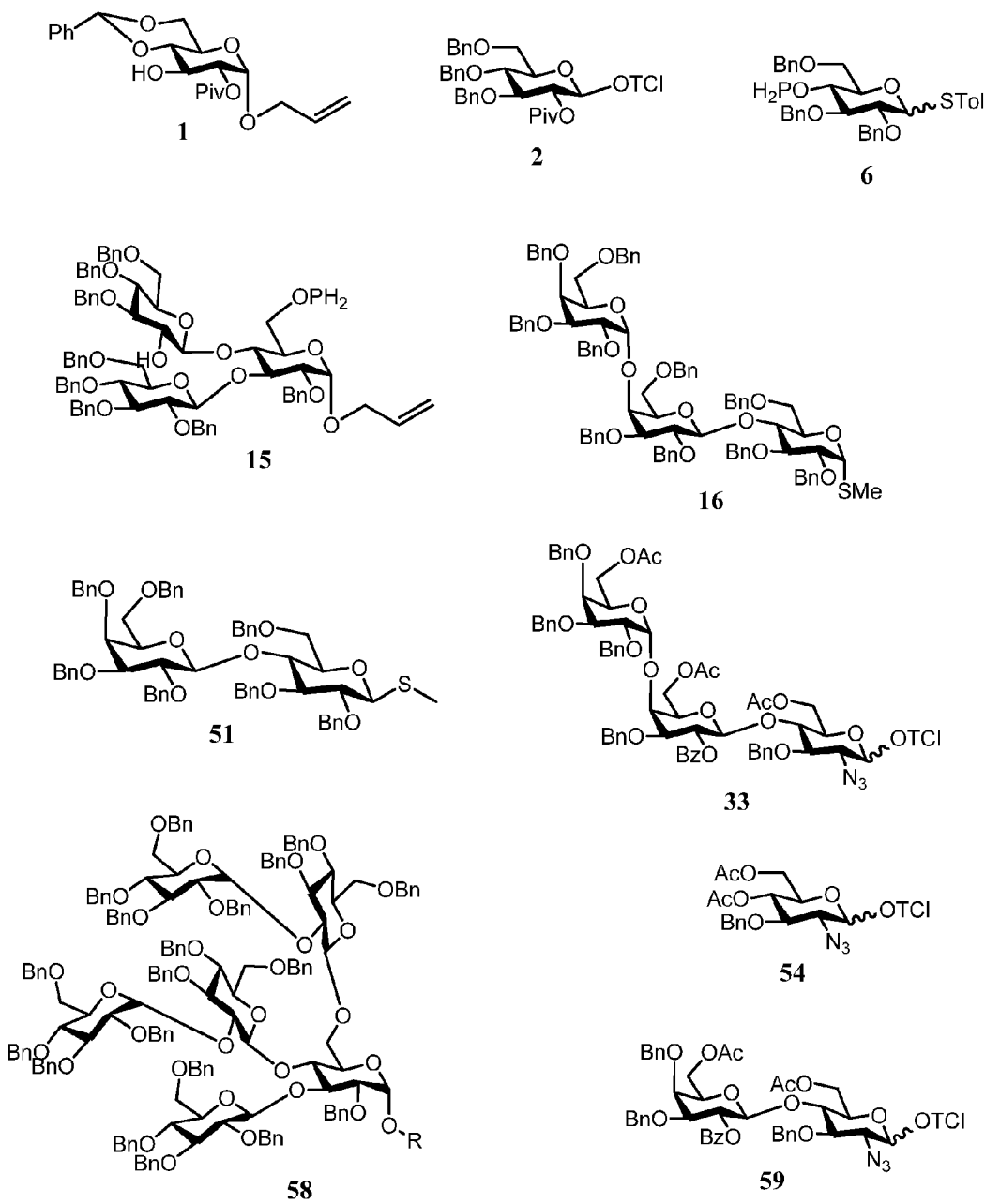
FIG. 3 depicts common intermediates used for synthesizing the oligosaccharide antigens of the present invention.

In order to provide a clear and consistent understanding of the specification and claims, the following definitions are provided.

Units, prefixes, and symbols may be denoted in their SI accepted form. Numeric ranges recited herein are inclusive of the numbers defining the range and include and are supportive of each integer within the defined range. Unless otherwise noted, the terms "a" or "an" are to be construed as meaning "at least one of." The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

As used herein, "oligosaccharide" refers to a compound containing two or more monosaccharide units. Oligosaccharides are considered to have a reducing end and a non-reducing end, whether or not the monosaccharide unit at the reducing end is in fact a reducing sugar. In accordance with accepted nomenclature, oligosaccharides are depicted herein with the non-reducing end on the left and the reducing end on the right. All oligosaccharides described herein are described with the name or abbreviation for the non-reducing monosaccharide (e.g., Gal), preceded by the configuration of the glycosidic bond (α or β), the ring bond, the ring position of the reducing monosaccharide involved in the bond, and then the name or abbreviation of the reducing monosaccharide (e.g., GlcNAc). The linkage between two sugars may be expressed, for example, as 2,3, 2→3, or 2-3. Each monosaccharide is a pyranose or furanose.

As used herein, "monosaccharide" or "monosaccharide unit" refers to a single sugar residue in an oligosaccharide, including derivatives therefrom. Within the context of an oligosaccharide, an individual monomer unit is a monosaccharide which is (or can be) bound through a hydroxyl group to another monosaccharide.

As used herein, "endotoxin-free" refers to an oligosaccharide that does not contain endotoxins or endotoxin components normally present in isolated bacterial carbohydrates and polysaccharides.

As used herein, "synthetic" refers to material which is substantially or essentially free from components, such as endotoxins, glycolipids, unrelated oligosaccharides, etc., which normally accompany a compound when it is isolated. Typically, synthetic compounds are at least about 90% pure, usually at least about 95%, and preferably at least about 99% pure. Purity can be indicated by a number of means well known in the art. Preferably, purity is measured by HPLC. The identity of the synthetic material can be determined by mass spectroscopy and/or NMR spectroscopy.

As used herein the term "linker" refers to either a bond or a moiety which at one end exhibits a grouping able to enter into a covalent bonding with a reactive functional group of the carrier, e.g. an amino, thiol, or carboxyl group, and at the other end a grouping likewise able to enter into a covalent bonding with a hydroxyl group or an amino group of an oligosaccharide according to the present invention. Between the two functional groups of the linker molecule there is a biocompatible bridging molecule of suitable length, e.g. substituted or unsubstituted heteroalkylene, arylalkylene, alkylene, alkenylene, or (oligo)alkylene glycol groups. Linkers preferably include a substituted or unsubstituted ($C_1$-$C_{10}$) alkylene group or an substituted or unsubstituted ($C_2$-$C_{10}$) alkenylene group.

As used herein, the term "carrier" refers to a protein, peptide, lipid, polymer, dendrimer, virosome, virus-like particle (VLP), or combination thereof, which is coupled to the oligosaccharide to enhance the immunogenicity of the resulting oligosaccharide-carrier conjugate to a greater degree than the oligosaccharide alone.

As used herein, "protein carrier" refers to a protein, peptide or fragment thereof, which is coupled or conjugated to an oligosaccharide to enhance the immunogenicity of the resulting oligosaccharide-protein carrier conjugate to a greater degree than the oligosaccharide alone. For example, when used as a carrier, the protein carrier may serve as a T-dependent antigen which can activate and recruit T-cells and thereby augment T-cell dependent antibody production.

As used herein, "conjugated" refers to a chemical linkage, either covalent or non-covalent, that proximally associates an oligosaccharide with a carrier so that the oligosaccharide conjugate has increased immunogenicity relative to an unconjugated oligosaccharide.

As used herein, "conjugate" refers to an oligosaccharide chemically coupled to a carrier through a linker and/or a cross-linking agent.

As used herein, "passive immunity" refers to the administration of antibodies to a subject, whereby the antibodies are produced in a different subject (including subjects of the same and different species) such that the antibodies attach to the surface of the bacteria and cause the bacteria to be phagocytosed or killed.

As used herein, "protective immunity" means that a vaccine or immunization schedule that is administered to a animal induces an immune response that prevents, retards the development of, or reduces the severity of a disease that is caused by a pathogen or diminishes or altogether eliminates the symptoms of the disease. Protective immunity may be predicted based on the ability of serum antibody to activate complement-mediated bactericidal activity or confer passive protection against a bacterial infection in a suitable animal challenge model.

As used herein, "immunoprotective composition" refers to a composition formulated to provide protective immunity in a host.

As used herein, "in a sufficient amount to elicit an immune response" or "in an effective amount to stimulate an immune response" (e.g., to epitopes present in a preparation) means that there is a detectable difference between an immune response indicator measured before and after administration of a particular antigen preparation. Immune response indicators include but are not limited to: antibody titer or specificity, as detected by an assay such as enzyme-linked immunoassay (ELISA), bactericidal assay (e.g., to detect serum bactericidal antibodies), flow cytometry, immunoprecipitation, Ouchter-Lowry immunodiffusion; binding detection assays of, for example, spot, Western blot or antigen arrays; cytotoxicity assays, and the like.

As used herein, "antibody" encompasses polyclonal and monoclonal antibody preparations, as well as preparations including hybrid antibodies, altered antibodies, $F(ab')^2$ fragments, F(ab) molecules, Fv fragments, single chain fragment variable displayed on phage (scFv), single domain antibodies, chimeric antibodies, humanized antibodies, and functional fragments thereof which exhibit immunological binding properties of the parent antibody molecule.

As used herein, "monoclonal antibody" refers to an antibody composition having a homogeneous antibody population. The term is not limited by the manner in which it is made. The term encompasses whole immunoglobulin molecules, as well as Fab molecules, $F(ab')_2$ fragments, Fv fragments, single chain fragment variable displayed on phage (scFv), and other molecules that exhibit immunological binding properties of the parent monoclonal antibody molecule.

As used herein, "specifically binds to an antibody" or "specifically immunoreactive with", when referring to an oligosaccharide, protein or peptide, refers to a binding reaction which is based on and/or is probative of the presence of the antigen in a sample which may also include a heterogeneous population of other molecules. Thus, under designated immunoassay conditions, the specified antibody or antibodies bind(s) to a particular antigen or antigens in a sample and does not bind in a significant amount to other molecules present in the sample. Specific binding to an antibody under such conditions may require an antibody or antiserum that is selected for its specificity for a particular antigen or antigens.

As used herein, "antigen" refers to any substance that may be specifically bound by an antibody molecule.

As used herein, "immunogen" and "immunogenic composition" refer to an antigenic composition capable of initiating lymphocyte activation resulting in an antigen-specific immune response.

As used herein, "epitope" refers to a site on an antigen to which specific B cells and/or T cells respond. The term is also used interchangeably with "antigenic determinant" or "antigenic determinant site." B cell epitope sites on proteins, oligosaccharides, or other biopolymers may be composed of moieties from different parts of the macromolecule that have been brought together by folding. Epitopes of this kind are referred to as conformational or discontinuous epitopes, since the site is composed of segments the polymer that are discontinuous in the linear sequence but are continuous in the folded conformation(s). Epitopes that are composed of single segments of biopolymers or other molecules are termed continuous or linear epitopes. T cell epitopes are generally restricted to linear peptides. Antibodies that recognize the same epitope can be identified in a simple immunoassay showing the ability of one antibody to block the binding of another antibody to a target antigen.

The term Ac means acetyl (—C(O)CH$_3$).
The term TBS means tert-butyldimethylsilyl.
The term Troc means 2,2,2-trichloroethoxycarbonyl.
The term TCI means trichloroacetimidate.
The term Phth means phthaloyl.
The term TFA means trifluoroacetate.
The term TCA means trichloroacetate.
The term Cbz means benzyloxycarbonyl.
The term Bz means benzoyl.
The term Bn means benzyl.
The term TES means triethylsilyl.
The term TBDPS means tert-butyldiphenylsilyl.
The term MCA means monochloracetate.
The term Lev means levulinoyl.
The term ADMB means 4-O-acetyl 12,2 dimethylbutanoate.
The term Tr means triphenylmethyl.
The term DMT means dimethoxytrityl.
The term FMOC means 9-fluorenylmethyl carbonate.
The term Alloc means Allyloxycarbonyl.
The term Nap means napthyl.
The term SEt means thioethyl.
The term SPh means thiophenyl.
The term STol means thiotolyl.
The term SAdm means thioadamantyl.

Synthetic Oligosaccharides

The present invention provides compositions and methods for chemically synthesizing antigenic structures corresponding to the *M. catarrhalis* lipooligosaccharide (LOS), a major surface component of the outer membrane. Greater than 95% of isolated *M. catarrhalis* strains possess one of three LOS serotypes: A (61%), B (29%) and C (5%; Vaneechoutte et al., *J. Clin. Microbiol.*, 28:182, 1990). The LOS structures of all three serotypes have been thoroughly characterized and are composed of a branched oligosaccharide anchored to the cell membrane via a KDO$_2$-lipid A moiety, a common glycolipid motif found in many species of gram negative bacteria (Edebrink et al., *Carbohydr. Res.*, 257:269, 1994; Edebrink et al., *Carbohydr. Res.*, 295:127, 1996; Edebrink et al., *Carbohydr. Res.*, 266:237, 1995). The oligosaccharide portion from all three of the characterized LOS structure serotypes contains a common, highly branched glucose core (FIG. 1). The structural variance observed among the three serotypes is found in the composition of the α and β chains (FIGS. 1 and 2; Braun et al., *Vaccine*, 22:898, 2004). The three serotypes all are comprised of glucose and galactose residues and the A and C serotypes also contain an N-acetyl glucosamine in the β chain. Analytical characterization shows that each serotype generates a full length, primary LOS structure, defined as A, B11 and C11. Additional characterization of the B and C *M. catarrhalis* serotypes reveals that different strains of these bacteria also display additional forms of the B and C oligosaccharides, representing partial deletion sequences of the primary serotype antigen (FIG. 2). Of the three serotypes, the B serotype shows the greatest natural variability; the full length sequence B11 is thought to be the primary virulence factor while the other B sequences are believed to be expressed at different points in the bacterial life cycle (Braun et al., *Vaccine*, 22:898, 2004).

FIG. 2 depicts the composition of α and β chains of the naturally occurring *M. catarrhalis* LOS structures. The shaded entries represent the most common sequence found in each serotype; the other entries include deletion sequences found as lesser components in LOS fractions (Braun et al., *Vaccine*, 22:898, 2004). In its natural presentation, the lipid portion is buried in the bacterial cell membrane, presenting the oligosaccharide region to the surrounding environment.

In one aspect, the present invention provides oligosaccharides 1a:

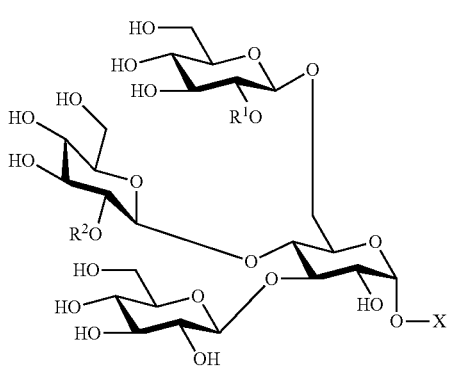

where each of R$^1$ and R$^2$ is independently H, a monosaccharide or a oligosaccharide, and X is H or a protecting group.

The present invention further provides antigens 1b:

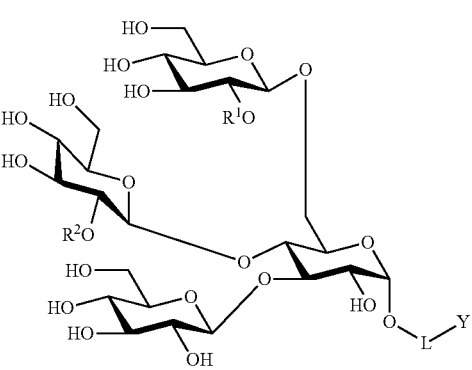

where each of R$^1$ and R$^2$ is independently H, a monosaccharide or a oligosaccharide; L is a linker; and Y is H or a carrier.

In compounds 1a and 1b, oligosaccharides may include one or more monosaccharide units linked to one another through one or more α- and/or β-glycosidic bonds. Preferably, the oligosaccharides will include monosaccharides and glycosidic linkages naturally found in *M. catarrhalis* LOS structures, generally in 1-2 or 1-4 connectivities. The invention further contemplates other connectivities, such as 1-3 and 1-6, especially where the oligosaccharide design is extended beyond naturally M. catarrhalis LOS structures.

When either of $R^1$ or $R^2$ is an oligosaccharide, it may contain between 1 to about 6, preferably up to about 4, monosaccharide units. The invention contemplates inclusion of natural and modified monosaccharide units, such as D-mannose, D-galactose, D-glucosamine, D-fucose, and sialic acid, especially where the oligosaccharide design is extended beyond naturally M. catarrhalis LOS structures.

In compounds 1a and 1b, preferred monosaccharides include Gal (galactosyl); GalNAc (N-acetylgalactosaminyl); Glc (glucosyl); GlcNAc (N-acetylglucosaminyl); sialic acid (Neu5Ac).

In compounds 1a and 1b, preferred oligosaccharides for $R^1$ and $R^2$ are di-, tri-, and tetra-saccharides. Preferred oligosaccharides contain one or more units of Gal, GalNAc, Glc, and GlcNAc. The units are preferably connected via 1-4 bonds.

Preferred oligosaccharides 1a according to the present invention have the $R^1$ and $R^2$ values in Table 1.

In Table 1, X is preferably H. In another embodiment, X is preferably a protecting group.

In another aspect, the present invention provides LOS antigens comprised of core oligosaccharide structures or motifs corresponding to one or more of the three major serotypes, members within a given serotype, and individual serotype subtypes as depicted in Table 1. In the following embodiments, L is exemplified as an alkylene thiol group, where p is an integer from 1 to 20, preferably between 1 and 8. In any of these embodiments, the linker shown (i.e., the alkylene thiol group) could be replaced with any other suitable linker as described herein. The following embodiments are identified elsewhere by Formula numbers corresponding to oligosaccharides of Formula 1a where the linker is —$(CH_2)_3$—S—, however, the structures are depicted as having generic thiol linkers.

Thus, in one embodiment, the invention provides an tetrasaccharide 5:

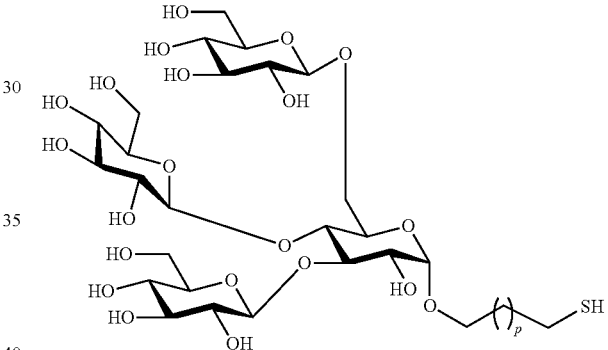

TABLE 1 preferred oligosaccharides 1a

| Compound # | R1 | R2 |
|---|---|---|
| 56 | αGlc(1-2) | H |
| 8 |  | αGlc(1-2) |
| 70 |  | βGal(1-4)αGlc(1-2) |
| 71 |  | αGal(1-4)βGal(1-4)αGlc(1-2) |
| 52 |  | αGlcNAc(1-2) |
| 54 |  | βGal(1-4)αGlcNAc(1-2) |
| 72 |  | αGal(1-4)βGal(1-4)αGlcNAc(1-2) |
| 5 | H | H |
| 72 |  | αGlc(1-2) |
| 74 |  | βGal(1-4)αGlc(1-2) |
| 75 |  | αGal(1-4)βGal(1-4)αGlc(1-2) |
| 76 |  | αGlcNAc(1-2) |
| 77 |  | βGal(1-4)αGlcNAc(1-2) |
| 78 |  | αGal(1-4)βGal(1-4)αGlcNAc(1-2) |
| 79 | βGal(1-4)αGlc(1-2) | H |
| 80 |  | αGlc(1-2) |
| 11 |  | βGal(1-4)αGlc(1-2) |
| 81 |  | αGal(1-4)βGal(1-4)αGlc(1-2) |
| 82 |  | αGlcNAc(1-2) |
| 83 |  | βGal(1-4)αGlcNAc(1-2) |
| 84 |  | αGal(1-4)βGal(1-4)αGlcNAc(1-2) |
| 46 | αGal(1-4)βGal(1-4)αGlc(1-2) | H |
| 85 |  | αGlc(1-2) |
| 86 |  | βGal(1-4)αGlc(1-2) |
| 20 |  | αGal(1-4)βGal(1-4)αGlc(1-2) |
| 27 |  | αGlcNAc(1-2) |
| 87 |  | βGal(1-4)αGlcNAc(1-2) |
| 37 |  | αGal(1-4)βGal(1-4)αGlcNAc(1-2) |

In another embodiment, the invention provides an pentasaccharide 56:

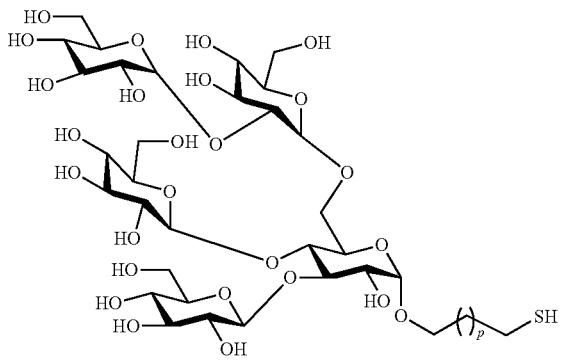

In another embodiment, the invention provides a heptasaccharide 46:
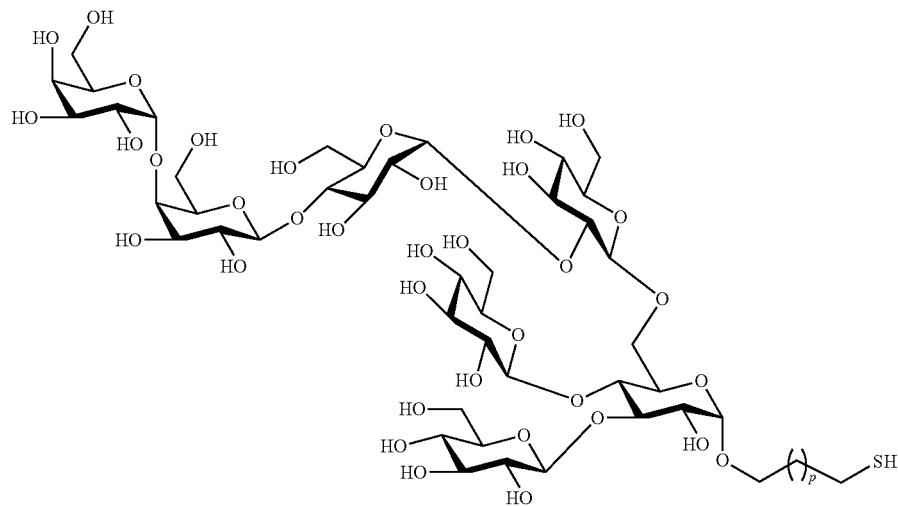
46
In another embodiment, the invention provides a hexsaccharide 52:
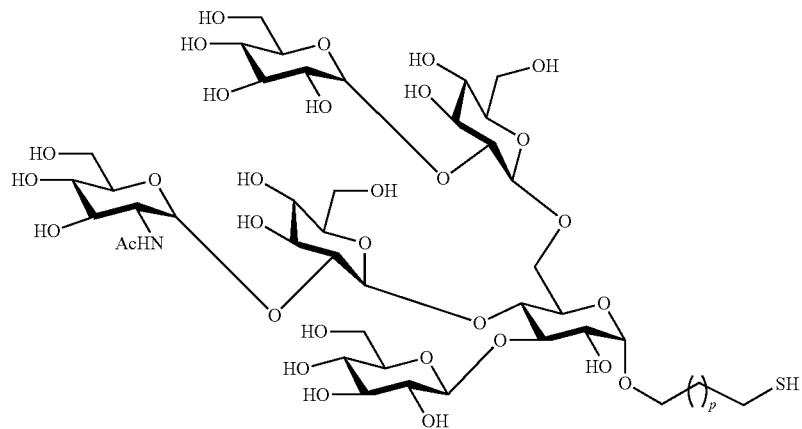
52
In another embodiment, the invention provides an octasaccharide 27:
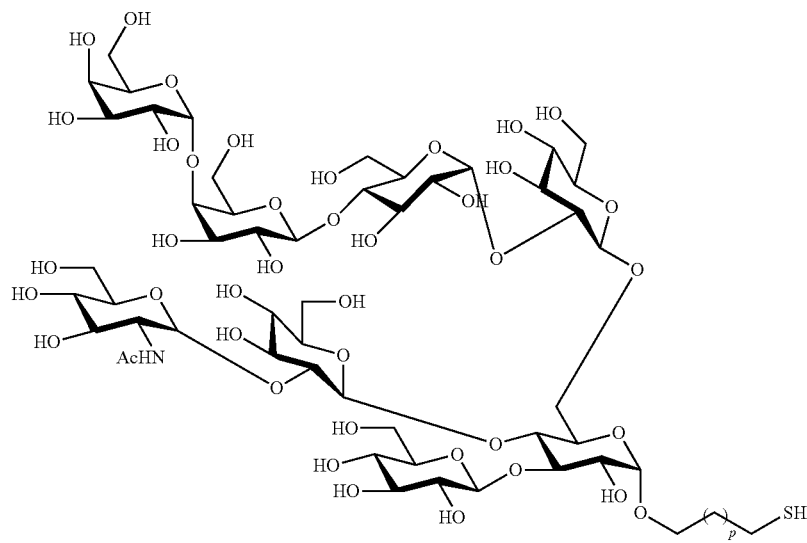
27

In another embodiment, the invention provides a hexasaccharide 8:
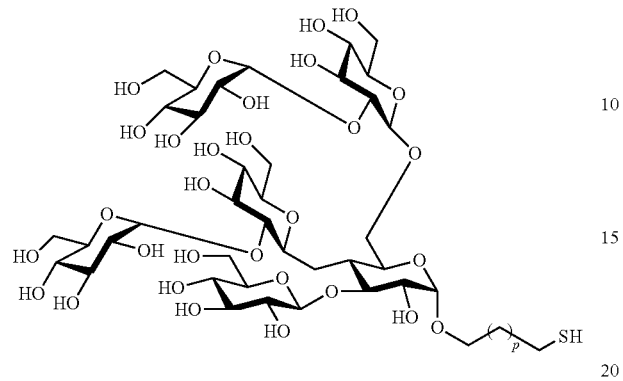
In a further embodiment, the invention provides an octasaccharide 11:
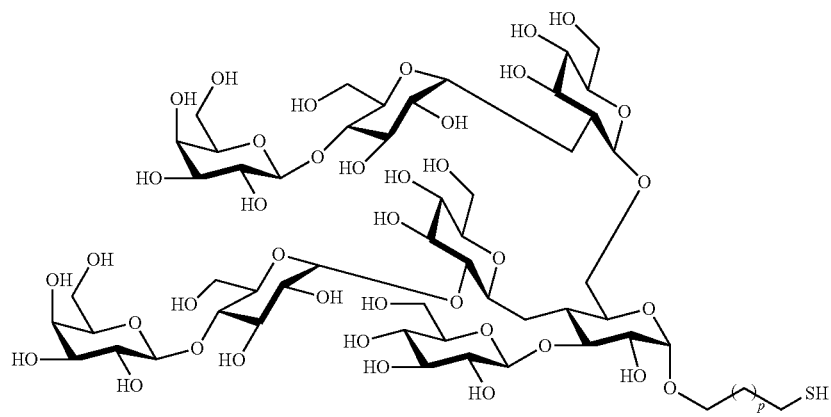
In a further embodiment, the invention provides a decasaccharide 20:
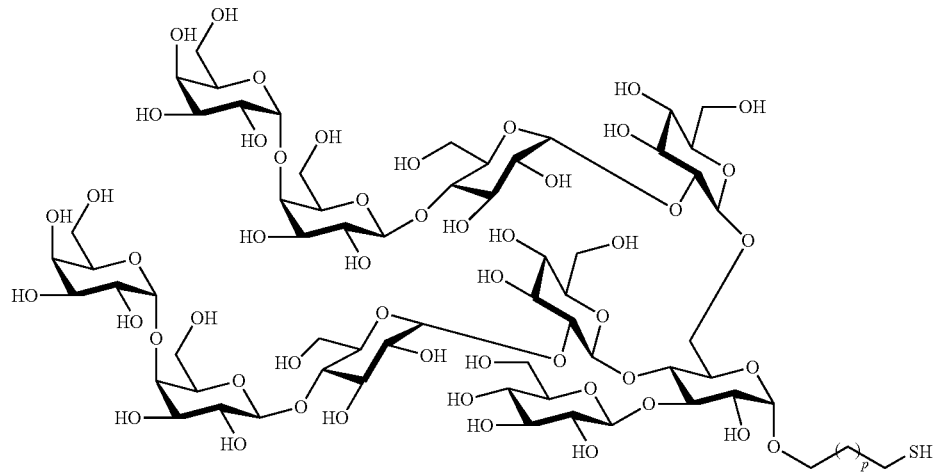

In another embodiment, the invention provides a heptasaccharide 54:
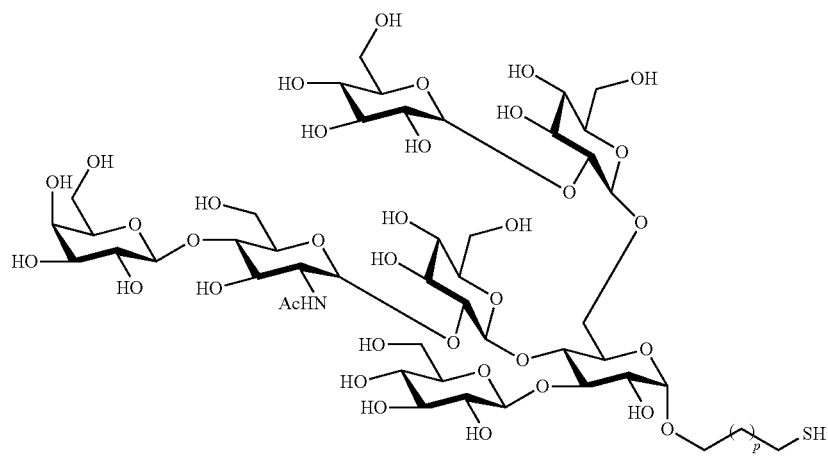
In a further embodiment, the invention provides a decasaccharide 37:
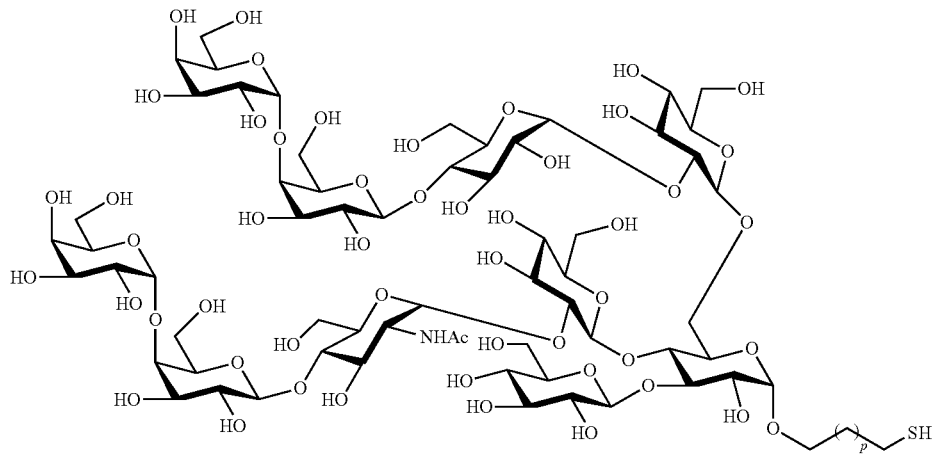
In a further embodiment, the invention provides a heptasaccharide 40:
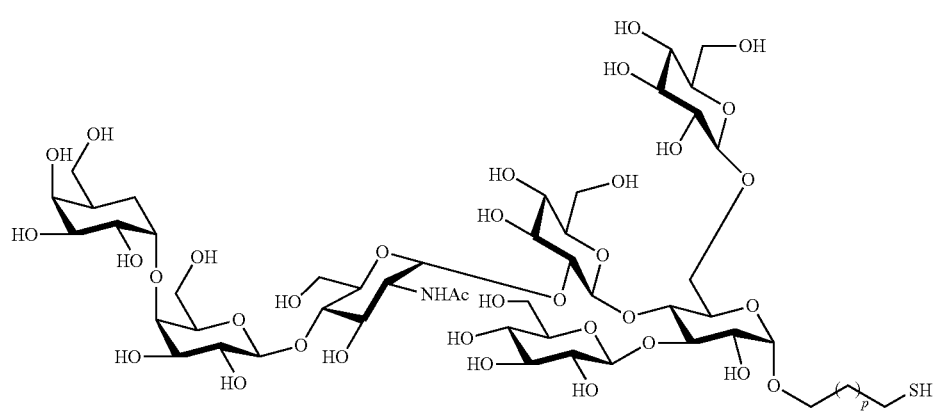

It should be recognized, that the present invention contemplates and provides sufficient guidance below for modifying any of the above-described thiol products with different linkers and/or spacers, and to make LOS structures directed to any of the oligosaccharide sequences listed in FIG. 2, including any subsequence combinations derived therefrom, or indeed, any *M. catarrhalis* LOS structure for that matter.

In a further aspect, the invention provides polyvalent LOS antigen combinations (and conjugates thereof) representing pluralities of any of the different oligosaccharides described in Table 1 or FIG. 2, for example.

The compositions can be mono-, di-, tri- or tetra-valent, containing antigens against the same serotype (i.e. two antigens to serotype A) or different serotypes. For example, the following compositions containing polyvalent antigen combinations aganst different serotypes are contemplated below in Table 2:

TABLE 2 combination vaccines

| Vaccine No. | Serotype | | | |
|---|---|---|---|---|
| | A | B | C | core |
| CV1 | 0 | 0 | 1 | 1 |
| CV2 | 0 | 1 | 0 | 1 |
| CV3 | 0 | 1 | 1 | 0 |
| CV4 | 0 | 1 | 1 | 1 |
| CV5 | 1 | 0 | 0 | 1 |
| CV6 | 1 | 0 | 1 | 0 |
| CV7 | 1 | 0 | 1 | 1 |
| CV8 | 1 | 1 | 0 | 0 |
| CV9 | 1 | 1 | 0 | 1 |
| CV10 | 1 | 1 | 1 | 0 |
| CV11 | 1 | 1 | 1 | 1 |

1 = present; 0 = absent

Compositions of the present invention include LOS-oligosaccharide structures defined by Formulas 1a and 1b, which may include a linker (L) and may optionally contain a carrier (Y is H or a carrier).

Suitable linkers comprise at one end a grouping able to enter into a covalent bonding with a reactive functional group of the carrier, e.g. an amino, thiol, or carboxyl group, and at the other end a grouping likewise able to enter into a covalent bonding with a hydroxyl group of an oligosaccharide according to the present invention. Between the two functional groups of the linker molecule there is a biocompatible bridging molecule of suitable length, e.g. substituted or unsubstituted heteroalkylene, arylalkylene, alkylene, alkenylene, or (oligo)alkylene glycol groups. Linkers preferably include substituted or unsubstituted alkylene or alkenylene groups containing 1-10 carbon atoms.

Linkers able to react with thiol groups on the carrier are, for example, maleimide and carboxyl groups; preferred groupings able to react with aldehyde or carboxyl groups are, for example, amino or thiol groups. Preferred covalent attachments between linkers and carriers include thioethers from reaction of a thiol with an α-halo carbonyl or α-halo nitrile, including reactions of thiols with maleimide; hydrazides from reaction of a hydrazide or hydrazine with an activated carbonyl group (e.g. activated NHS-ester or acid halide); triazoles from reaction of an azide with an alkyne (e.g. via "click chemistry"); and oximes from reaction of a hydroxylamine and an aldehyde or ketone as disclosed, for example, in Lees et al., *Vaccine*, 24:716, 2006. Although amine-based conjugation chemistries could be used in principle for coupling linkers and/or spacers to the oligosaccharides described herein, these approaches would typically sacrifice uniformity inasmuch as the oligosaccharides of the present invention typically contain a plurality of amines bonded to second carbon of the respective monosaccharide units.

Further suitable linker molecules are known to skilled workers and commercially available or can be designed as required and depending on the functional groups present and can be prepared by known methods.

Suitable carriers are known in the art (See e.g., Remington's Pharmaceutical Sciences (18th ed., Mack Easton, Pa. (1990)) and may include, for example, proteins, peptides, lipids, polymers, dendrimers, virosomes, virus-like particles (VLPs), or combinations thereof, which by themselves may not display particular antigenic properties, but can support immunogenic reaction of a host to the oligosaccharides of the present invention (antigens) displayed at the surface of the carrier(s).

Preferably, the carrier is a protein carrier, including but are not limited to, bacterial toxoids, toxins, exotoxins, and non-toxic derivatives thereof, such as tetanus toxoid, tetanus toxin Fragment C, diphtheria toxoid, CRM (a nontoxic diphtheria toxin mutant) such as CRM 197, cholera toxoid, *Staphylococcus aureus* exotoxins or toxoids, *Escherichia coli* heat labile enterotoxin, *Pseudomonas aeruginosa* exotoxin A, including recombinantly produced, genetically detoxified variants thereof; bacterial outer membrane proteins, such as *Neisseria meningitidis* serotype B outer membrane protein complex (OMPC), outer membrane class 3 porin (rPorB) and other porins; keyhole limpet hemocyanine (KLH), hepatitis B virus core protein, thyroglobulin, albumins, such as bovine serum albumin (BSA), human serum albumin (HSA), and ovalbumin; pneumococcal surface protein A (PspA), pneumococcal adhesin protein (PsaA); purified protein derivative of tuberculin (PPD); transferrin binding proteins, polyamino acids, such as poly(lysine:glutamic acid); peptidyl agonists of TLR-5 (e.g. flagellin of motile bacteria like *Listeria*); and derivatives and/or combinations of the above carriers. Preferred carriers for use in humans include tetanus toxoid, CRM 197, and OMPC.

Depending on the type of bonding between the linker and the carrier, and the structural nature of the carrier and oligosaccharide, a carrier may display on average, for example, 1 to 500, 1 to 100, 1 to 20, or 3 to 9 oligosaccharide units on its surface.

Methods for attaching an oligosaccharide to a carrier, such as a carrier protein are conventional, and a skilled practitioner can create conjugates in accordance with the present invention using conventional methods. Guidance is also available in various disclosures, including, for example, U.S. Pat. Nos. 4,356,170; 4,619,828; 5,153,312; 5,422,427; and 5,445,817; and in various print and online Pierce protein cross-linking guides and catalogs (Thermo Fisher, Rockford, Ill.).

In one embodiment, the carbohydrate antigens of the present invention are conjugated to CRM 197, a commercially available protein carrier used in a number of FDA approved vaccines. CRM-conjugates have the advantage of being easier to synthesize, purify and characterize than other FDA approved carriers such as OMPC. Carbohydrate antigens may be conjugated to CRM via thiol-bromoacetyl conjugation chemistry. CRM activation may be achieved by reacting the lysine side chains with the NHS ester of bromoacetic acid using standard conditions as previously described in U.S. Pat. Appl. Publ. 2007-0134762, the disclosures of which are incorporated by reference herein. CRM may be functionalized with 10-20 bromoacetyl groups per protein (n=10-20) prior to conjugation. Conjugation may be performed at pH=9 to avoid aggregation of CRM. Careful monitoring of pH must be employed to ensure complete CRM reaction with NHS-bromoacetate while minimizing background hydrolysis of CRM. Activated CRM may be purified by size exclusion chromatography prior to conjugation. Antigen-CRM conjugates may be synthesized by reacting thiol-terminated carbohydrate antigens with bromoacetamide-activated CRM.

CRM conjugates may be purified via size exclusion chromatography to remove and recover any unreacted carbohydrate. MBTH (specific for GlcNAc residues) and Bradford assays may be used to determine carbohydrate:protein ratio and protein content, respectively, as previously described (Manzi et al., Curr. Prot. Mol. Biol., section 17.9.1 (Suppl. 32), 1995. In preferred embodiments, a minimum carbohydrate content of about 10% by weight for each conjugate may be generated. Typically, a conjugate may include about 3-20 antigens per protein carrier.

In another embodiment, carbohydrate antigens may be conjugated to one or more carriers suitable for development of diagnostic assays, including ELISAs and microarrays. Exemplary carriers for use in such assays include bovine serum albumin (BSA), keyhole limpet hemocyanine (KLH), biotin, a label, a glass slide or a gold surface. By way of example, synthetic carbohydrate antigens may be conjugated to BSA by a thiol-maleimide coupling procedure (FIG. 5B). Maleimide-BSA contains 15-20 maleimide groups per protein (n=15-20). Accordingly, oligosaccharide antigens may be conjugated to maleimide functionalized BSA, whereby a 20-fold molar excess of the antigen is reacted with commercially available Imject maleimide BSA (Pierce) in maleimide conjugation buffer (Pierce). Conjugation may be performed at pH=7.2 to avoid hydrolysis of the maleimide group during conjugation.

BSA conjugates may be purified via size exclusion chromatography to remove and recover any unreacted carbohydrate. Characterization via the phenol-sulfuric acid and Bradford assays may be performed along with MALDI-MS to provide information on the carbohydrate content and valency of the conjugates. In preferred embodiments, conjugates will contain a minimum carbohydrate content of about 10% by weight per BSA conjugate and >8 antigen copies per conjugate.

Compositions and methods for synthesis of the above described LOS-oligosaccharides and conjugates thereof, including others described in Table 1 and FIG. 2 as further described in Examples 1 to 9 below.

Methods for Synthesizing LOS-Oligosaccharide Structures

In a further aspect, the present invention provides a method for assembling synthetic homogenous LOS-oligosaccharide structures from *M. catarrhalis*, including those described above from monosaccharide and disaccharide building blocks.

Thus, in one aspect, the invention provides a monosaccharide building blocks of Formulas 1 and 2:

1

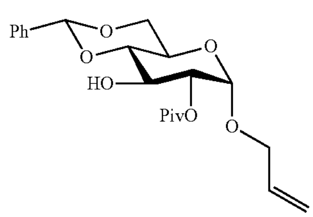

-continued

2

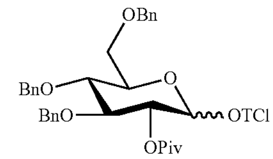

A method for synthesizing the building block 1 is described in Example 1 below. A method for synthesizing the building block 2 is described in Example 2 below. Building blocks 1 and 2 are used to generate a disaccharide building block of Formula 3:

3

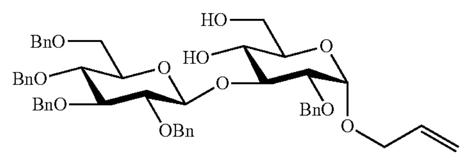

Disaccharide building block 3 may be combined with the monosaccharide building block of Formula 2 to produce a tetrasaccharide of Formula 4 reflecting a core structure present in all *M. catarrhalis* LOS structures:

4

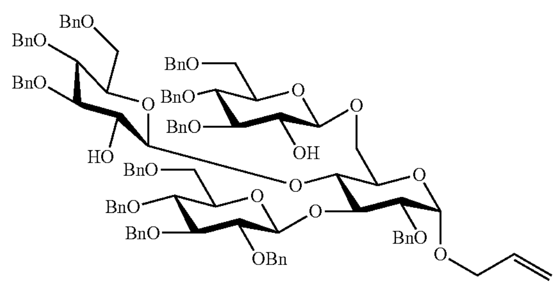

Other common building blocks are shown in FIG. 3 and an be used to synthesize core structures 4 and 15. For example, mono and disaccharide building blocks 1, 6, 16, 33, 51, 54, 55, 56, and 59 can be used in combination with the trisaccharide core 15 and the tetrasaccharide core 4 can enable production of virtually any *M. catarrhalis* LOS structure.

The tetrasaccharide core 4 may be elaborated to larger fragments of or complete oligosaccharides from *M. catarrhalis* using an assembly strategy such as that shown in FIG. 3. The alpha- and beta chains may be added sequentially or in tandem, and may be the same or different, depending on the desired target molecule. Elaboration may be accomplished using monosaccharide building blocks or di-, tri- or tetrasaccharide building blocks, such as those disclosed in steps A and B of FIG. 3.

Compositions and methods for synthesis of the above described LOS-oligosaccharides and conjugates thereof, including others described in Table 1 or FIG. 2 are described in Examples 1 to 9 below. Protecting groups employed in the synthesis of LOS-oligosaccharides may include those customarily considered in sugar chemistry, for example those mentioned in "Protective Groups in Organic Synthesis", $3^{rd}$ edition, T. W. Greene and P. G. M. Wuts (Ed.), John Wiley and Sons, New York, 1999.

In one embodiment, the present invention provides A method of synthezing a compound of the formula 90:

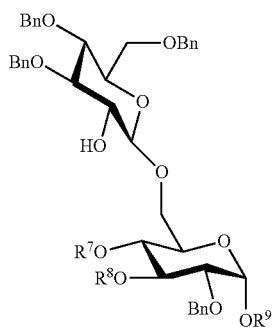

comprising contacting a first intermediate of the formula:

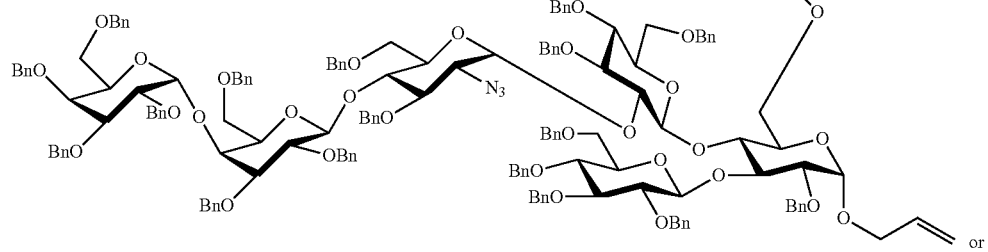

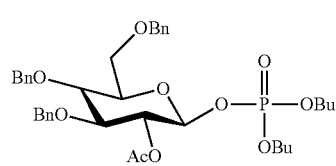

with a second intermediate of the formula:

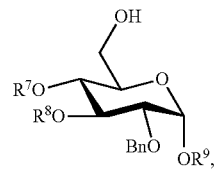

where $R^7$ is a Bn or is a monosaccharide or oligosaccharide; $R^8$ is a Bn or is a monosaccharide or oligosaccharide; and $R^9$ is a protecting group or linker consisting of —$CH_2CH$=$CH_2$, —$CH_2CCH$, pentenyl, alkenylene, oligoalkyl thiol.

In some embodiments the compound 90 is either

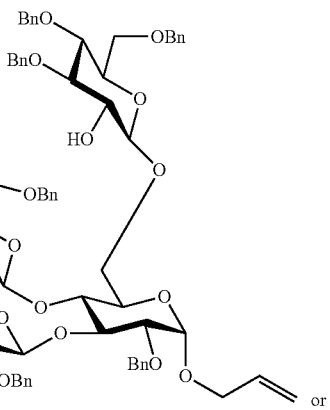

or

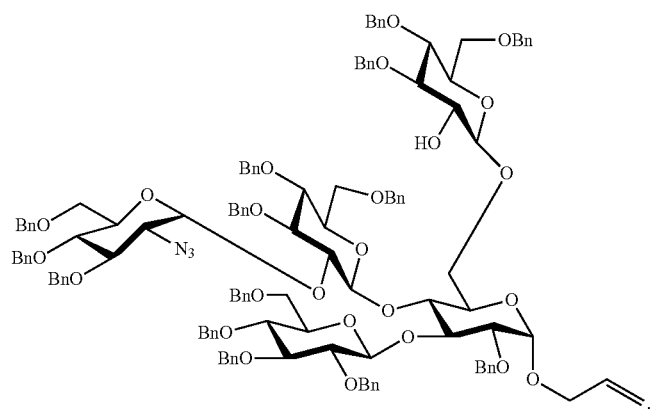

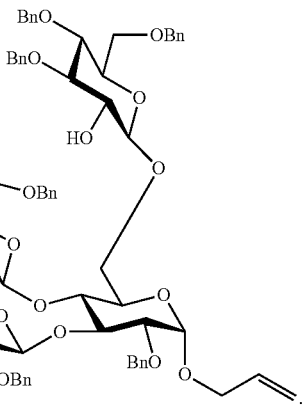

Immunogenic and Immunoprotective Compositions and Methods of their Use

In another aspect, the present invention provides immunogenic and immunoprotective compositions containing LOS oligosaccharides or LOS oligosaccharide-protein carrier conjugates for inducing an immune response to LOS antigens. The immunogenic compositions may include one or more adjuvants, as well as pharmaceutically acceptable vehicles suitable for administration to an animal or individual. An immunogenic or immunoprotective composition will include a "sufficient amount" or "an immunologically effective amount" of a oligosaccharide-protein carrier conjugate according to the present invention, as well as any of the above mentioned components, for purposes of generating an immune response or providing protective immunity, as further defined herein.

In one embodiment, the invention provides an immunogenic composition comprising one or more LOS oligosaccharide(s) 1a or LOS oligosaccharide-protein carrier conjugate(s) 1b suitable for inducing an immune response against M. catarrhalis.

In another embodiment, the invention provides a pharmaceutical composition comprising a LOS oligosaccharide(s) 1a or LOS oligosaccharide-protein carrier conjugate 1b formulated as a vaccine for protection against M. catarrhalis infections.

In another embodiment, the invention provides a pharmaceutical composition comprising an oligosaccharide-protein carrier conjugate 1b formulated as a vaccine for protecting against one or more M. catarrhalis serotypes as described herein.

In a further embodiment, the invention provides a pharmaceutical composition comprising an antibody and a physiologically acceptable vehicle for use in a method for providing passive immunity or treatment against one or more M. catarrhalis serotypes. More particularly, the invention provides an antibody preparation against one or more LOS-oligosaccharide conjugate 1b compositions in accordance with the present invention. The antibody preparation may include any member from the group consisting of polyclonal antibody, monoclonal antibody, mouse monoclonal IgG antibody, humanized antibody, chimeric antibody, fragment thereof, or combination thereof. The invention further contemplates a hybridoma cell producing a monoclonal antibody directed against any of the LOS-oligosaccharide described herein.

Administration of oligosaccharides or oligosaccharide-protein carrier conjugates or antibodies thereto may be carried out by any suitable means, including by parenteral administration (e.g., intravenously, subcutaneously, intradermally, or intramuscularly); by topical administration, of for example, antibodies to an airway surface; by oral administration; by in ovo injection in birds, for example, and the like.

In specific embodiments, each immunogenic or immunoprotective composition includes one or more oligosaccharide(s) according to Formula 1a or 1b or conjugates thereof in a pharmaceutically acceptable vehicle or diluent forming a substantially aqueous mixture. In preferred embodiments, the immunogenic or immunoprotective compositions includes one or more oligosaccharide-protein carrier conjugates(s) in conjunction with one or more pharmaceutically acceptable adjuvant(s), vehicles and/or protein carriers suitable for administration to an animal or individual.

Adjuvants

An oligosaccharide-protein carrier conjugate composition may further include one or more immunologic adjuvant(s). An immunologic adjuvant is a compound that, when combined with an antigen, increases the immune response to the antigen as compared to the response induced by the antigen alone so that less antigen can be used to achieve a similar response. For example, an adjuvant may augment humoral immune responses, cell-mediated immune responses, or both.

Those of skill in the art will appreciate that the terms "adjuvant," and "carrier," can overlap to a significant extent. For example, a substance which acts as an "adjuvant" may also be a "carrier," and certain other substances normally thought of as "carriers," for example, may also function as an "adjuvant." Accordingly, a substance which may increase the immunogenicity of the synthetic oligosaccharide or carrier associated therewith is a potential adjuvant. As used herein, a carrier is generally used in the context of a more directed site-specific conjugation to an oligosaccharide of the present invention, whereby an adjuvant is generally used in a less specific or more generalized structural association therewith.

Exemplary adjuvants and/or adjuvant combinations may be selected from the group consisting of mineral salts, including aluminum salts, such as aluminum phosphate and aluminum hydroxide (alum) (e.g., Alhydrogel™, Superfos, Denmark) and calcium phosphate; RIBI, which contains three components extracted from bacteria, monophosphoryl lipid A, trehalose dimycolate, and cell wall skeleton (MPL+TDM+CWS) in a 2% squalene/Tween 80 emulsion, whereby any of the 3 components MPL, TDM or CWS may also be used alone or combined 2 by 2; toll-like receptor (TLR) agonists, including, for example, agonists of TLR-1 (e.g. tri-acyl lipopeptides); agonists of TLR-2 [e.g. peptidoglycan of gram-positive bacteria like streptococci and staphylococci; lipoteichoic acid]; agonists of TLR-3 (e.g. double-stranded RNA and their analogs such as poly 1:C); agonists of TLR-4 (e.g. lipopolysaccharide (endotoxin) of gram-negative bacteria like Salmonella and E. coli); agonists of TLR-5 (e.g. flagellin of motile bacteria like Listeria); agonists of TLR-6 (e.g. with TLR-2 peptidoglycan and certain lipids (diacyl lipopeptides)); agonists of TLR-7 (e.g. single-stranded RNA (ssRNA) genomes of such viruses as influenza, measles, and mumps; and small synthetic guanosine-base antiviral molecules like loxoribine and ssRNA and their analogs); agonists of TLR-8 (e.g. binds ssRNA); agonists of TLR-9 (e.g. unmethylated CpG of the DNA of the pathogen and their analogs; agonists of TLR-10 (function not defined) and TLR-11-(e.g. binds proteins expressed by several infectious protozoans (Apicomplexa), specific toll-like receptor agonists include monophosphoryl lipid A (MPL®), 3 De-O-acylated monophosphoryl lipid A (3 D-MPL), OM-174 (E. coli lipid A derivative); OM triacyl lipid A derivative, and other MPL- or lipid A-based formulations and combinations thereof, including MPL®-SE, RC-529 (Dynavax Technologies), AS01(liposomes+MPL+QS21), AS02 (oil-in-water PL+QS-21), and AS0 4 (Alum+MPL) (GlaxoSmith Kline, Pa.), CpG-oligodeoxynucleotides (ODNs) containing immunostimulatory CpG motifs, double-stranded RNA, polyinosinic:polycytidylic acid (poly I:C), and other oligonucleotides or polynucleotides optionally encapsulated in liposomes; oil-in-water emulsions, including AS03 (GlaxoSmith Kline, Pa.), MF-59(microfluidized detergent stabilized squalene oil-in-water emulsion; Novartis), and Montanide ISA-51 VG (stabilized water-in-oil emulsion) and Montanide ISA-720 (stabilized water/squalene; Seppic Pharmaceuticals, Fairfield, N.J.); cholera toxin B subunit; saponins, such as QuilA or QS21, an HPLC purified non-toxic fraction derived from the bark of Quillaja Saponaria Molina (STIMULON™ (Antigenics, Inc., Lexington, Mass.) and saponin-based adjuvants, including immunostimulating complexes (ISCOMs; structured complex of saponins and lipids) and other ISCOM-based adjuvants, such as ISCOMATRIX™ and AbISCO®-100 and -300 series adjuvants (Isconova AB, Uppsala, Sweden); QS21 and 3 D-MPL together with an oil in water emulsion as disclosed in U.S. Pat. Appl. No. 2006/0073171; stearyl tyrosine (ST) and amide analogs thereof; virus-like particles (VLPs) and reconstituted influenza virosomes (IRIVs); complete Freund's adjuvant (CFA); incomplete Freund's adjuvant (IFA); E. coli heat-labile enterotoxin (LT); immune-adjuvants, including cytokines, such as IL-2, IL-12, GM-CSF, Flt3, accessory molecules, such as B7.1, and mast cell (MC) activators, such as mast cell activator compound 48/80(C48/80); water-insoluble inorganic salts; liposomes, including those made from DNPC/Chol and DC Chol; micelles; squalene; squalane; muramyl dipeptides, such as N-acetyl-muramyl-L-threonyl-D-isoglutamine (thr-MDP) as found in U.S. Pat. No. 4,606,918, N-acetyl-normuramyl-L-alanyl-D-isoglutamine (nor-MDP), and N-acetylmuramyl-L-alanyl-D-isoglutaminyl-L-alanine-2-(1'2'-dipalmitoyl-n-glycero-3-hydroxyphosphoryl; SAF-1 (Syntex); AS05 (GlaxoSmith Kline, Pa.); and combinations thereof.

In preferred embodiments, adjuvant potency may be enhanced by combining multiple adjuvants as described above, including combining various delivery systems with immunopotentiating substances to form multi-component adjuvants with the potential to act synergistically to enhance antigen-specific immune responses in vivo. Exemplary immunopotentiating substances include the above-described adjuvants, including, for example, MPL and synthetic derivatives, MDP and derivatives, oligonucleotides (CpG etc), ds RNAs, alternative pathogen-associated molecular patterns (PAMPs) (*E. coli* heat labile enterotoxin; flagellin, saponins (QS-21 etc), small molecule immune potentiators (SMIPs, e.g., resiquimod [R848]), cytokines, and chemokines.

Pharmaceutically-Acceptable Delivery Vehicles

Pharmaceutically-acceptable delivery vehicles, including those described above may be employed to enhance the delivery and/or control the duration of action. Control release preparations may be achieved through the use of polymers to complex or absorb the oligosaccharides, oligosaccharide conjugates, and/or adjuvants. Controlled delivery may be effected by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly(methylmethacylate)-microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences, supra.

The oligosaccharide compositions of the present invention, including oligosaccharide-protein carrier conjugate compositions, can be formulated according to known methods to prepare pharmaceutically useful compositions, whereby these materials, or their functional derivatives, are combined in admixture with a pharmaceutically acceptable vehicle (or diluents). Suitable vehicles and their formulation, inclusive of other human proteins, e.g., human serum albumin, are described, for example, in Remington's Pharmaceutical Sciences, supra. In order to form a pharmaceutically acceptable composition suitable for effective administration, such compositions will contain an effective amount of the above-described compounds together with a suitable amount of protein carrier and/or vehicle.

Typically, the immunogenic or immunoprotective compositions may be prepared as injectables, either as liquid solutions or suspensions; solid forms suitable for solution in, or suspension in, liquid vehicles prior to injection. An aqueous composition for parenteral administration, for example, may include a solution of the immunogenic component(s) dissolved or suspended in a pharmaceutically acceptable vehicle or diluent, preferably a primarily aqueous vehicle. Pharmaceutically acceptable vehicles or diluents may include water, saline, including neutral saline solutions buffered with phosphate, Tris, glycerol, ethanol, and the like. An aqueous composition may be formulated as a sterile, pyrogen-free buffered saline or phosphate-containing solution, which may include a preservative or may be preservative free. Suitable preservatives include benzyl alcohol, parabens, thimerosal, chlorobutanol, and benzalkonium chloride, for example. Aqueous solutions are preferably approximately isotonic, and its tonicity may be adjusted with agents such as sodium tartrate, sodium chloride, propylene glycol, and sodium phosphate. Additionally, auxiliary substances required to approximate physiological conditions, including pH adjusting and buffering agents, tonicity adjusting agents, wetting or emulsifying agents, pH buffering substances, and the like, including sodium acetate, sodium lactate, sodium chloride, potassium chloride, calcium chloride, sorbitan monolaurate, triethanolamine oleate, etc. may be included with the vehicles described herein.

These compositions may be sterilized by conventional sterilization techniques, or may be sterile filtered. The resulting aqueous solutions may be packaged for use as is, or lyophilized, the lyophilized preparation being combined with a sterile solution prior to administration. The preparation of such pharmaceutical compositions is within the ordinary skill in the art, and may be guided by standard reference books such as Remington's Pharmaceutical Science, supra, which is incorporated herein by reference.

Compositions may be formulated in a solid or liquid form for oral delivery. For solid compositions, nontoxic and/or pharmaceutically acceptable solid protein carriers may include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition may be formed by incorporating any of the normally employed excipients, including those protein carriers previously listed, and a unit dosage of an active ingredient, that is, one or more compounds of the invention, whether conjugated to a protein carrier or not.

Topical application of antibodies to an airway surface, for example, can be carried out by intranasal administration (e.g., by use of dropper, swab, or inhaler which deposits a pharmaceutical formulation intranasally). Topical application of the antibodies to an airway surface can also be carried out by inhalation administration, such as by creating respirable particles of a pharmaceutical formulation (including both solid particles and liquid particles) containing the antibodies as an aerosol suspension, and then causing the subject to inhale the respirable particles. Methods and apparatuses for administering respirable particles of pharmaceutical formulations are well known, and any conventional technique can be employed. Oral administration may be in the form of an ingestable liquid or solid formulation.

Further, compositions may be formulated in an aerosol for nasal administration. For aerosol administration, the immunogenic compounds are preferably supplied in finely divided form along with one or more surfactant(s) and/or propellant(s). The surfactant will be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A protein carrier can also be included, as desired, as with, e.g., lecithin for intranasal delivery.

The concentration of the immunogenic oligosaccharides of the invention in the pharmaceutical formulations can vary widely, i.e., from less than about 0.1%, usually at or at least about 0.1% to as much as 20% to 50% or more by weight, and will be selected primarily by fluid volumes, viscosities, etc., and in accordance with the particular mode of administration selected. A human unit dose form of the compounds and composition is typically included in a pharmaceutical composition that comprises a human unit dose of an acceptable protein carrier, preferably an aqueous protein carrier, and is administered in a volume of fluid that is known by those of skill in the art to be used for administration of such compositions to humans, and is adjusted according to commonly understood principles for a particular subject to be treated. Thus in one embodiment, the invention provides a unit dosage of the vaccine components of the invention in a suitable amount of an aqueous solution, such as 0.1-3 ml, preferably 0.2-2 mL.

Methods of Treatment

The immunogenic and immunoprotective compositions of the present invention may be administered to any animal species at risk for developing an infection by *M. catarrhalis*.

The treatment may be given in a single dose schedule, or preferably a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

The amounts effective for inducing an immune response or providing protective immunity will depend on a variety of factors, including the oligosaccharide composition, conjugation to a protein carrier, inclusion and nature of adjuvant(s), the manner of administration, the weight and general state of health of the patient, and the judgment of the prescribing physician. By way of example, the amounts may generally range for the initial immunization (that is for a prophylactic administration) from about 1.0 µg to about 5,000 µg of carbohydrate antigen for a 70 kg patient, (e.g., 1.0 µg, 2.0 µg, 2.5 µg, 3.0 µg, 3.5 µg, 4.0 µg, 4.5 µg, 5.0 µg, 7.5 µg, 10 µg, 12.5 µg, 15 µg, 17.5 µg, 20 µg, 25 µg, 30 µg, 35 µg, 40 µg, 45 µg, 50 µg, 75 µg, 100 µg, 250 µg, 500 µg, 750 µg, 1,000 µg, 1,500 µg, 2,000 µg, 2,500 µg, 3,000 µg, 3,500 µg, 4,000 µg, 4,500 µg or 5,000 µg). The actual dose administered to a subject is often determined according to an appropriate amount per kg of the subject's body weight. For example, an effective amount may be about 0.1 µg to 5 µg/kg body weight.

A primary dose may optionally be followed by boosting dosages of from about 1.0 to about 1,000 of carbohydrate antigen (e.g., 1.0 µg, 2.0 µg, 2.5 µg, 3.0 µg, 3.5 µg, 4.0 µg, 4.5 µg, 5.0 µg, 7.5 µg, 10 µg, 12.5 µg, 15 µg, 17.5 µg, 20 µg, 25 µg, 30 µg, 35 µg, 40 µg, 45 µg, 50 µg, 75 µg, 100 µg, 250 µg, 500 µg, 750 µg, 1,000 µg, 1,500 µg, 2,000 µg, 2,500 µg, 3,000 µg, 3,500 µg, 4,000 µg, 4,500 µg or 5,000 µg) pursuant to a boosting regimen over weeks to months depending upon the patient's response and condition by measuring specific T cell activity in the patient's blood.

The present invention contemplates the use of single- and multi-valent glycoconjugate vaccines comprising any of the synthetic oligosaccharides described herein. The identification of a single oligosaccharide antigen eliciting a cross-reactive immune response can facilitate development of a single-antigen vaccine candidate active against all common *M. catarrhalis* bacterial serotypes and/or strains.

The present invention further contemplates multi-antigen glycoconjugate vaccines comprising a plurality of any of the synthetic oligosaccharides described herein so as to provide protection against a single serotype or serotype subtype of *M. catarrhalis* or against a plurality of serotypes or serotype subtypes of *M. catarrhalis*. Thus, in one embodiment, for example, the invention provides a composition containing two, three, four or more different oligosaccharide antigens according to Formula 1b.

The immunogenic compositions comprising a compound of the invention may be suitable for use in adult humans or in children, including young children or others at risk for contracting an infection caused by a LOS-expressing bacterial species. Optionally such a composition may be administered in combination with other pharmaceutically active substances, and frequently it will be administered in combination with other vaccines as part of a childhood vaccination program.

Compositions for administration may beneficially include multiple oligosaccharide- or oligosaccharide conjugates that elicit an immune response to a plurality of different epitopes so as to provide increased protection against a single strain or serotype of *M. catarrhalis* or against a plurality of strains or serotypes of *M. catarrhalis*. Moreover, compositions may be administered whereby a prime immunization with one or multiple antigen conjugates is followed by boosting events with one or more cross-reactive core conjugates according to the present invention.

Antibody Compositions

In another embodiment, the invention provides diagnostic antibodies, as well as pharmaceutical compositions comprising one or more anti-LOS antibody(ies) or a functional fragment(s) thereof, and a physiologically acceptable vehicle. Methods for generating these antibodies are further described below.

Pharmaceutical antibody compositions may be used in a method for providing passive immunity against *M. catarrhalis* infections. A pharmaceutical antibody composition may be administered to an animal subject, preferably a human, in an amount sufficient to prevent or attenuate the severity, extent of duration of the infection by one or more strains or serotypes of *M. catarrhalis*.

The administration of one or more antibodies may be either prophylactic (prior to anticipated exposure to a bacterial infection) or therapeutic (after the initiation of the infection, at or shortly after the onset of the symptoms). The dosage of the one or more antibodies will vary depending upon factors as the subject's age, weight and species. In general, the dosage of the antibody may be in a range from about 1-10 mg/kg body weight. In a preferred embodiment, the antibody is a humanized antibody of the IgG or the IgA class. The route of administration of the one or more antibodies may be oral or systemic, for example, subcutaneous, intramuscular or intravenous.

The use of antibodies as diagnostic agents is further described below and in U.S. Pat. No. 7,595,307 and U.S. Pat.

Appl. Publ. No. 2009/0155299, the discolosures of which are incorporated by reference herein.

The present invention also provides one or more kits useful for diagnosing, treating, and/or preventing an *M. catarrhalis* infection. For example, the kits may include one or more containers holding the diagnostic or pharmaceutical compositions of the invention. The kits may also include other container(s) containing, for example, one or more solutions necessary or convenient for the particular diagnostic or pharmaceutical use. The container means can be made of glass, plastic or foil and can be a vial, bottle, pouch, tube, bag, etc. The kit may also contain written information, such as procedures for carrying out the present invention or analytical information, such as the amount of reagent contained in the container(s).

Generation of Antibodies and their Use in Assay Development

In a further aspect, the present invention provides compositions and methods for inducing production of antibodies for use in assay development, including their use as detection agents and serum screening tools.

Antisera to LOS-conjugates may be generated in New Zealand white rabbits by 3-4 subcutaneous injections over 13 weeks. A pre-immune bleed may generate about 5 mL of baseline serum from each rabbit. A prime injection (10 μg antigen equivalent) may be administered as an emulsion in complete Freund's adjuvant (CFA). Subsequent injections (5 μg antigen equivalent) may be given at three week intervals in incomplete Freund's adjuvant (IFA). Rabbits may be bled every two weeks commencing one week after the third immunization. Approximately 25-30 mL of serum per rabbit may be generated from each bleeding event and frozen at −80° C. Serum may be analyzed by ELISA against the corresponding LOS-conjugate as described below. In addition, antisera from later bleeds may be affinity purified as further described below.

The oligosaccharides and antibodies of the present invention can be used as diagnostic reagents for detecting *M. catarrhalis* LOS antigens or antibodies thereagainst, which are present in biological samples. The detection reagents may be used in a variety of immunodiagnostic techniques, known to those of skill in the art, including ELISA- and microarray-related technologies. In addition, these reagents may be used to evaluate antibody responses, including serum antibody levels, to immunogenic oligosaccharide conjugates. The assay methodologies of the invention typically involve the use of labels such as fluorescent, chemiluminescent, radioactive, enzymatic labels or dye molecules, and/or secondary immunologic reagents for direct or indirect detection of a complex between an antigen or antibody in a biological sample and a corresponding antibody or antigen bound to a solid support.

Such assays typically involve separation of unbound antibody in a liquid phase from a solid phase support to which antibody-antigen complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Typically, a solid support is first reacted with a first binding component (e.g., an antigen or antibody in accordance with the present invention) under suitable binding conditions such that the first binding component is sufficiently immobilized to the support. In some cases, mobilization to the support can be enhanced by first coupling the antibody or oligosaccharide to a protein with better binding properties, or that provides for immobilization of the antibody or antigen on the support without significant loss of antibody binding activity or specificity. Suitable coupling proteins include, but are not limited to, macromolecules such as serum albumins including bovine serum albumin (BSA), keyhole limpet hemocyanin (KLH), immunoglobulin molecules, thyroglobulin, ovalbumin, and other proteins well known to those skilled in the art. Other molecules that can be used to bind antibodies the support include polysaccharides, polylactic acids, polyglycolic acids, polymeric amino acids, amino acid copolymers, and the like. Such molecules and methods of coupling these molecules are well known to those of ordinary skill in the art and are described in, e.g., U.S. Pat. No. 7,595,307 and U.S. Pat. Appl. No. US 2009/0155299.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 1

Synthesis of Monosaccharide Building Blocks

Figure 4A:
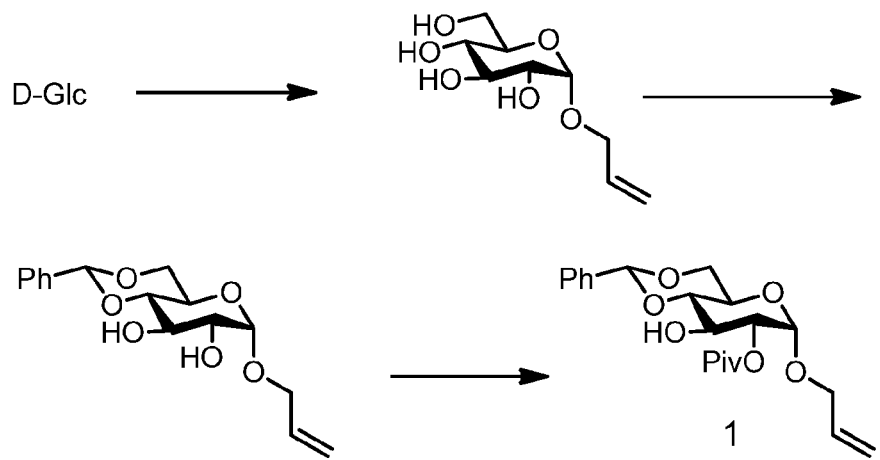
FIGS. 4A and 4B depict reaction schemes for forming monosaccharide building blocks as described in Example 1, including allyl 4,6-O-benzylidene-2-O-pivaloyl-α-D-glucopyranoside 1 (FIG. 4A); and 2-pivaloyl,3,4,6-tri-O-benzyl-6-D-glucopyranosyl trichloroacetimidate 2 (FIG. 4B).

Synthesis of allyl 4,6-O-benzylidene-2-O-pivaloyl-α-D-glucopyranoside 1 (FIG. 4A).

Allyl alcohol (500 mL, 7.35 mol) was cooled to 0° C. and acetyl chloride (72 mL, 1.0 mol) was added slowly, keeping the reaction mixture below 5° C. D-Glucose monohydrate (200 g, 1.0 mol) was added and the reaction mixture was stirred overnight at room temperature, then overnight at 40° C. The solvent was evaporated to provide a thick syrup, which was co-evaporated with toluene (500 mL) and used without further purification.

Crude allyl-D-glucopyranoside was dissolved in acetonitrile (1000 mL). To this stirred solution were added benzaldehyde dimethylacetal (250 mL, 1.7 mol) and (+/−)-camphor-10-sulfonic acid (12 g, 0.05 mol) and the solution was stirred at room temperature overnight. The solids were filtered off, the solvent was removed in vacuo and the residue was taken up in ethyl acetate (1000 mL), washed with saturated NaHCO$_3$ (3×200 mL) and water (3×200 mL) then evaporated to a thick syrup. The syrup was dissolved in hot ethanol (500 mL) and cooled to −20° C. for 2.5 days. The solid product was filtered and washed with cold ethanol, and dried under vacuum to give allyl-4,6-O-benzylidene-α-D-glucopyranoside (150 g, 48%).

Allyl-4,6-O-benzylidene-α-D-glucopyranoside (51 g, 165 mmol) was dissolved in pyridine (200 mL) and cooled to −20° C. Pivaloyl chloride (22 mL, 180 mmol) was added dropwise to the stirred solution over 20 minutes. After 1 hour at −20° C. another aliquot of pivaloyl chloride (22 mL, 180 mmol) was added over 20 minutes. After another 1 hour at −20° C. a final aliquot of pivaloyl chloride (22 mL, 180 mmol) was added over 20 minutes and stirring continued at −20° C. for an additional 1 hour. The reaction was quenched with methanol (40 mL) and allowed to warm to room temperature. The reaction mixture was diluted with ethyl acetate (600 mL) and washed with water (2×400 mL), brine (300 mL), 1 m NaOH (2×300 mL) and brine (300 mL), dried over Na$_2$SO$_4$, filtered and concentrated to give allyl 4,6-O-benzylidene-2-O-pivaloyl-α-D-glucopyranoside 1 as a crude product as a yellow oil (60 g, 92%).

Figure 4B:
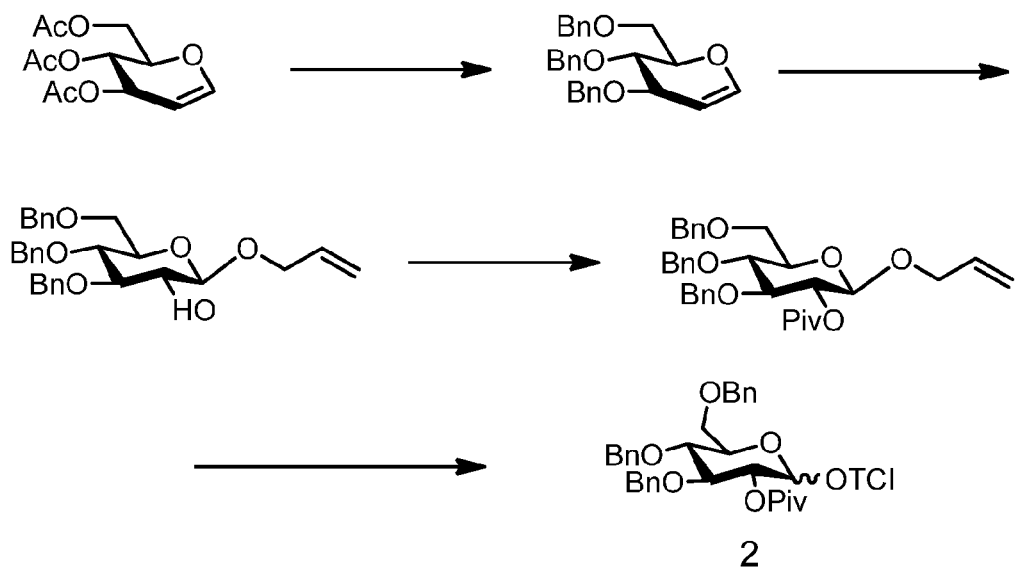

Synthesis of 2-pivaloyl,3,4,6-tri-O-benzyl-β-D-glucopyranosyl trichloroacetimidate 2 (FIG. 4B).

3,4,6-Tri-O-acetyl-D-glucal (5.0 g, 18.4 mmol) was dissolved in methanol (100 mL) and a solution of sodium methoxide in methanol (0.25 mL, 25% solution by weight, 1.1 mmol). The solution was stirred at room temperature for 3 hours. The solvent was removed and the resulting residue was co-evaporated with toluene (3×10 mL) before being taken up in a 4:1 solution of NMP:THF and cooled to 0° C. Solid NaH (3.3 g of 60% suspension, 82.5 mmol) was added and the mixture was stirred for 30 minutes before the addition of BnBr. The reaction mixture was stirred at room temperature overnight, quenched with methanol and the solvent removed. The residue was suspended in ethyl acetate, washed with 1 N HCl, brine, and saturated NaHCO$_3$ (100 mL each). The ethyl acetate solution was dried over MgSO$_4$, filtered and concentrated in vacuo. The crude material was purified on a silica gel column (80 g) using an ISCO automated chromatography system, eluting with a 0→50% gradient of ethyl acetate in heptane, to give 3,4,6-tri-O-benzyl-D-glucal (7.2 g, 94%).

3,4,6-tri-O-benzyl-D-glucal (7.2 g, 17.3 mmol) in CH$_2$Cl$_2$/acetone (2:1, 105 mL) and a saturated solution of NaHCO$_3$ (100 mL) was added. The mixture was stirred vigorously while a solution of Oxone (21.2 g, 34.6 mmol) in water (150 mL) was added dropwise over 30 minutes. After 1.5 hours of vigorous stirring the layers were separated, and the aqueous layer was extracted with CH$_2$Cl$_2$ (2×150 mL). The organic solutions were combined, dried over MgSO$_4$, filtered and concentrated. The residue was co-evaporated with toluene (3×10 mL), dissolved in allyl alcohol (25 mL) and stirred at room temperature overnight. The reaction mixture was purified on a silica gel column (80 g) using an ISCO automated chromatography system, eluting with a 0→60% gradient of ethyl acetate in heptane, to give allyl 3,4,6-tri-O-benzyl-β-D-glucopyranoside (4.2 g, 50%).

Allyl 3,4,6-tri-O-benzyl-β-D-glucopyranoside (4.2 g, 8.6 mmol) was dissolved in CH$_2$Cl$_2$ (100 mL) and pivaloyl chloride (1.7 mL, 12.9 mmol) and DMAP (1.6 g, 13.1 mmol) were added. The reaction mixture was stirred at room temperature for 18 hours, quenched with methanol, diluted with CH$_2$Cl$_2$, washed with saturated NH$_4$Cl solution, brine, saturated NaHCO$_3$ (100 mL each), dried over MgSO$_4$, filtered and concentrated to give crude allyl 2-pivaloyl,3,4,6-tri-O-benzyl-β-D-glucopyranoside (4.7 g, 95%).

Allyl 2-pivaloyl,3,4,6-tri-O-benzyl-β-D-glucopyranoside (3.2 g, 5.6 mmol) was dissolved in dry THF (20 mL) under an inert atmosphere. In a separate flask 1,5-cyclooctadienebis(methyldiphenylphosphine)-iridium(I) hexafluorophosphate (100 mg, 0.12 mmol) was suspended in dry THF (10 mL) under an inert atmosphere. H$_2$ gas was bubbled through the catalyst solution for 10 minutes during which the red suspension turned into a clear pale yellow solution. The solution was purged by N$_2$ gas bubbling for 10 minutes. The catalyst solution was then added to the allyl glycoside solution and stirred for 15 minutes. Next NMO (50% aqueous, 5 mL) and OsO$_4$ (25 mg, XX mmol) were added and the dark mixture was stirred for 2 hours. The reaction mixture was diluted with ethyl acetate, washed twice with brine and saturated NaHCO$_3$ (100 mL each), dried over Na$_2$SO$_4$, filtered and concentrated. The crude material was purified on a silica gel column (40 g) using an ISCO automated chromatography system, eluting with a 0→100% gradient of ethyl acetate in heptane, to give 2-pivaloyl,3,4,6-tri-O-benzyl-β-D-glucopyranose (2.65 g, 89%).

2-Pivaloyl,3,4,6-tri-O-benzyl-β-D-glucopyranose (8.2 g, 15.3 mmol) was dissolved in CH$_2$Cl$_2$ (50 mL) and trichloroacetonitrile (15 mL) was added followed by K$_2$CO$_3$ (10 g, 72 mmol). The mixture was stirred at room temperature for 8 hours, filtered and concentrated. The residue was passed through a plug of silica gel (washed previously with 1% Et$_3$N in heptanes) by elution with 3:1 heptane:ethyl acetate. Removal of the solvent gave the desired trichloroacetimidate product, 2-pivaloyl,3,4,6-tri-O-benzyl-β-D-glucopyranosyl trichloroacetimidate 2 (10.17 g, 97%).

Example 2

Synthesis of Tetramer Core and Conjugates thereof

Figure 5A:
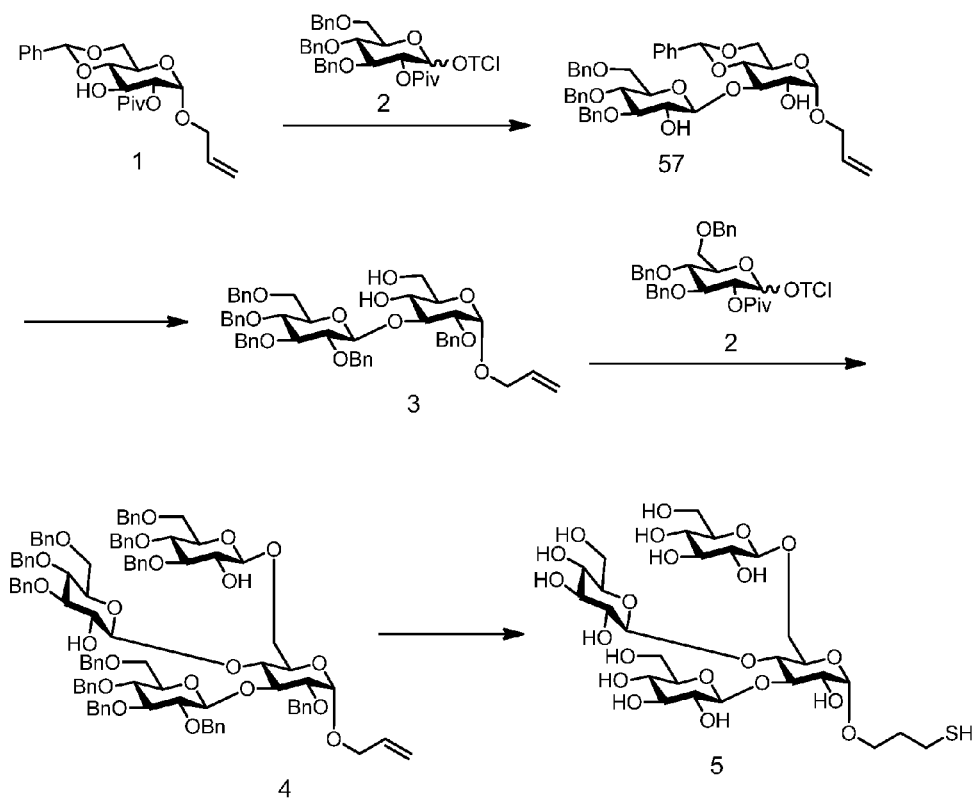
FIGS. 5A and 5B depict reactions schemes for synthesizing a tetramer core 5 (FIG. 5A); and conjugates 49, 50 thereof (FIG. 5B) as described in Example 2.

Synthesis of Tetramer Core 5 (FIG. 5A)

As shown in FIG. 5A, allyl 4,6-O-benzylidene-2-O-pivaloyl-α-D-glucopyranoside 1 (2.0 g, 5.1 mmol) and 2-pivaloyl,3,4,6-tri-O-benzyl-β-D -glucopyranosyl trichloroacetimidate 2 (4.1 g, 6.1 mmol) were combined, co-evaporated with toluene (3×10 mL) and dissolved in dry CH$_2$Cl$_2$ (50 mL). Freshly activated AW-300 molecular sieves (3 g) were added and the reaction mixture was stirred for 10 minutes and cooled to 0° C. A solution of trimethylsilyl trifluoromethanesulfonate (TMSOTf, 0.09 mL, 0.5 mmol) in CH$_2$Cl$_2$ (0.9 mL) was added and the reaction stirred for 30 minutes. The reaction mixture was filtered, quenched with Et$_3$N (1 mL) and the solvent removed to give the crude coupling product, which was used without further purification.

The crude coupling product was dissolved in methanol:tetrahydrofuran (1:1, 100 mL) and sodium methoxide solution (10 mL, 25% by weight, 44 mmol) was added. The solution was stirred at room temperature for 18 hours, then diluted with ethyl acetate (200 mL), washed with 1N HCl (100 mL), brine (100 mL), and saturated NaHCO$_3$ (100 mL), dried over MgSO$_4$, filtered and concentrated. The crude material was purified on a silica gel column (300 mL), eluting with 40:60 ethyl acetate: heptane, to give the desired disaccharide diol 57 (2.63 g, 70%).

The disaccharide diol 57 (2.63 g, 3.55 mmol) was dissolved in dry DMF (40 mL) and cooled to 0° C. Solid NaH (0.57 g of 60% suspension, 14.2 mmol) was added and the mixture was stirred for 10 minutes before the addition of BnBr (1.25 mL, 10.6 mmol). The reaction mixture was stirred at room temperature for 18 hours and quenched with methanol. The solution was diluted with ethyl acetate, washed with 1 N HCl, brine, and saturated NaHCO$_3$ (100 mL each). The ethyl acetate solution was dried over MgSO$_4$, filtered and concentrated in vacuo to give crude product, which was used without further purification.

The crude benzylation product was taken up in 80% acetic acid (50 mL) and heated at 50° C. for 4 hours. The reaction volume was reduced by 70% under vacuum then diluted with ethyl acetate (100 mL) and washed with water (3×100 mL) and saturated NaHCO$_3$ (2×100 mL), dried over MgSO$_4$, filtered and concentrated. The crude material was purified on a silica gel column (80 g) using an ISCO automated chromatography system, eluting with a 0→100% gradient of ethyl acetate in heptane, to give allyl 2-O-benzyl-3-O-(2,3,4,6-tetra-O-benzyl-β-D-glucopyranosyl)-α-D-glucopyranoside 3 (2.07 g, 70%).

The trichloroacetimidate donor 2 (257 mg, 0.378 mmol) and the diol acceptor 3 (105 mg, 0.126 mmol) were combined and co-evaporated with toluene (2×5 mL) then dissolve in dry CH$_2$Cl$_2$ (3 mL). Freshly activated AW-300 molecular sieves (0.5 g) were added and the reaction mixture was stirred for 10 minutes. A solution of trimethylsilyl trifluoromethanesulfonate (TMSOTf, 4.9 μL, 0.027 mmol) in $CH_2Cl_2$ (45 μL) was added and the reaction stirred for 30 minutes. The reaction mixture was quenched with $Et_3N$ (0.25 mL), filtered and the solvent removed to give the crude coupling product, which was purified on a silica gel column (40 g) using an ISCO automated chromatography system, eluting with a 0→70% gradient of ethyl acetate in heptane, to give the desired tetrasaccharide coupling product (45 mg, 19%). Trisaccharide product resulting from single coupling to the 6-OH position of the acceptor was also recovered as a by-product.

Tetrasaccharide was dissolved in methanol:tetrahydrofuran (1:1, 2 mL) and sodium methoxide solution (0.2 mL, 25% by weight, 0.88 mmol) was added. The solution was stirred at room temperature overnight, then diluted with ethyl acetate (50 mL), washed with 1N HCl (50 mL), brine (50 mL), and saturated $NaHCO_3$ (50 mL), dried over $MgSO_4$, filtered and concentrated. The crude coupling product was purified on a silica gel column (12 g) using an ISCO automated chromatography system, eluting with a 0→70% gradient of ethyl acetate in heptane, to give the desired tetrasaccharide product 4 (25 mg, 61%).

Tetrasaccharide 4 (375 mg, 0.221 mmol) was dissolved in dioxane (6 mL) under $N_2$ and AIBN (20 mg, 0.122 mmol) and thioacetic acid (0.50 mL, 7.1 mmol) were added. The reaction mixture was heated to 75° C. under an inert atmosphere for 2 hours, at which point another aliquot of AIBN (50 mg, 0.30 mmol) was added and stirring continued for 2 hours. The reaction was quenched by the addition of cyclohexene (1 mL) and after 15 minutes at 75° C. the reaction was cooled and the solvent was removed. The crude product was purified on a silica gel column (40 g) using an ISCO automated chromatography system, eluting with a 0→75% gradient of ethyl acetate in heptane, to give the desired tetrasaccharide thiol product (310 mg, 79%).

Tetrasaccharide thiol (310 mg, 0.175 mmol) was coevaporated with toluene (3×10 mL) and dissolved in dry THF (5 mL). In a jacketed flask equipped with a dry ice condenser and cooled to −78° C., $NH_3$ gas was condensed into the flask under an Ar atmosphere until the liquid volume reached approximately 20 mL. The tetrasaccharide thiol solution was transferred by cannula into the liquid $NH_3$. Sodium metal (250 mg, 10.9 mmol) was added under positive Ar gas flow and once a permanent blue color was established the reaction was stirred for another 20 minutes. The reaction was quenched at −78° C. by the addition of saturated $NH_4Cl$ solution (10 mL) and warmed to room temperature. $N_2$ was bubbled through the reaction mixture to remove excess $NH_3$, and then the solution was concentrated to 2 mL. The crude material was purified by size exclusion chromatography on a bed of BioGel P4 by elution with water. The fractions containing product were concentrated to yield the desired *Moraxella* tetrasaccharide core 5 (75 mg, 58%).

Figure 5B:
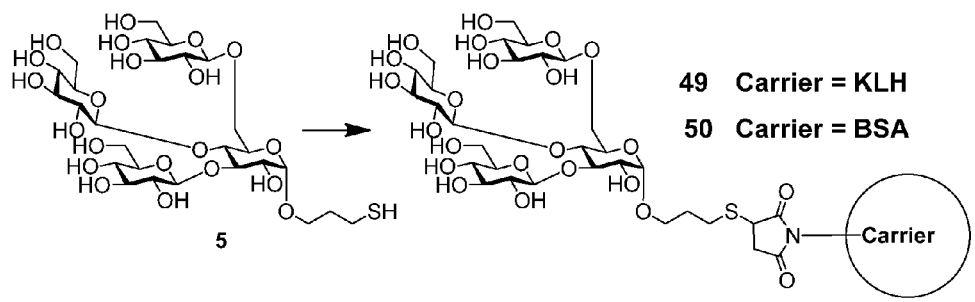

Synthesis of Tetramer Core Conjugates 49, 50 (FIG. 5B)

A solution of tris(2-carboxyethyl)phosphine (TCEP) in water (8.6 μL, 0.05 M, 0.43 μmol) was added to a solution of tetrasaccharide thiol 5 in water (8.3 mg/mL, 72 μL, 0.86 μmol), and the resulting solution was stirred for 1 hour. A solution of maleimide-activated keyhole limpet hemocyanin (Imject® KLH, Pierce, Rockford, Ill.) (0.5 mL, 5 mg, ~0.43 μmol maleimide) was added and the resulting solution stirred overnight at room temperature. The reaction mixture was purified by de-salting on D-Salt P-6000 10 mL column (Pierce, Rockford, Ill.). The column was pre-equilibrated with 30 mL of purification buffer (Pierce, Prod. No. 77159 which contains sodium chloride, sodium phosphate monobasic, sodium phosphate dibasic), the crude material loaded onto the column and eluted with purification buffer. 1-mL fractions were collected and analyzed for protein content by absorbance at 280 nm ($A_{280}$). Fractions containing protein were combined and lyophilized to give the desired tetramer-KLH conjugate 49 (4.61 mg).

A solution of tris(2-carboxyethyl)phosphine (TCEP) in water (30 μL, 0.05 M, 1.5 μmol) was added to a solution of tetrasaccharide thiol 5 in water (8.3 mg/mL, 265 μL, 3.0 μmol), and the resulting solution was stirred for 1 hour. A solution of maleimide-activated bovine serum albumin (Imject® BSA, Pierce, Rockford, Ill.) (0.5 mL, 5 mg, ~1.5 μmol maleimide) was added and the resulting solution stirred overnight at room temperature. The reaction mixture was purified by de-salting on D-Salt P-6000 10 mL column (Pierce, Rockford, Ill.). The column was pre-equilibrated with 30 mL of purification buffer (Pierce, Prod. No. 77159), the crude material loaded onto the column and eluted with purification buffer. 1-mL fractions were collected and analyzed for protein content by absorbance at 280 nm ($A_{280}$). Fractions containing protein were combined and lyophilized to give the desired tetramer-BSA conjugate 50 (4.07 mg).

Example 3

Synthesis of Heptamer Core and Conjugates thereof

Figure 6A:
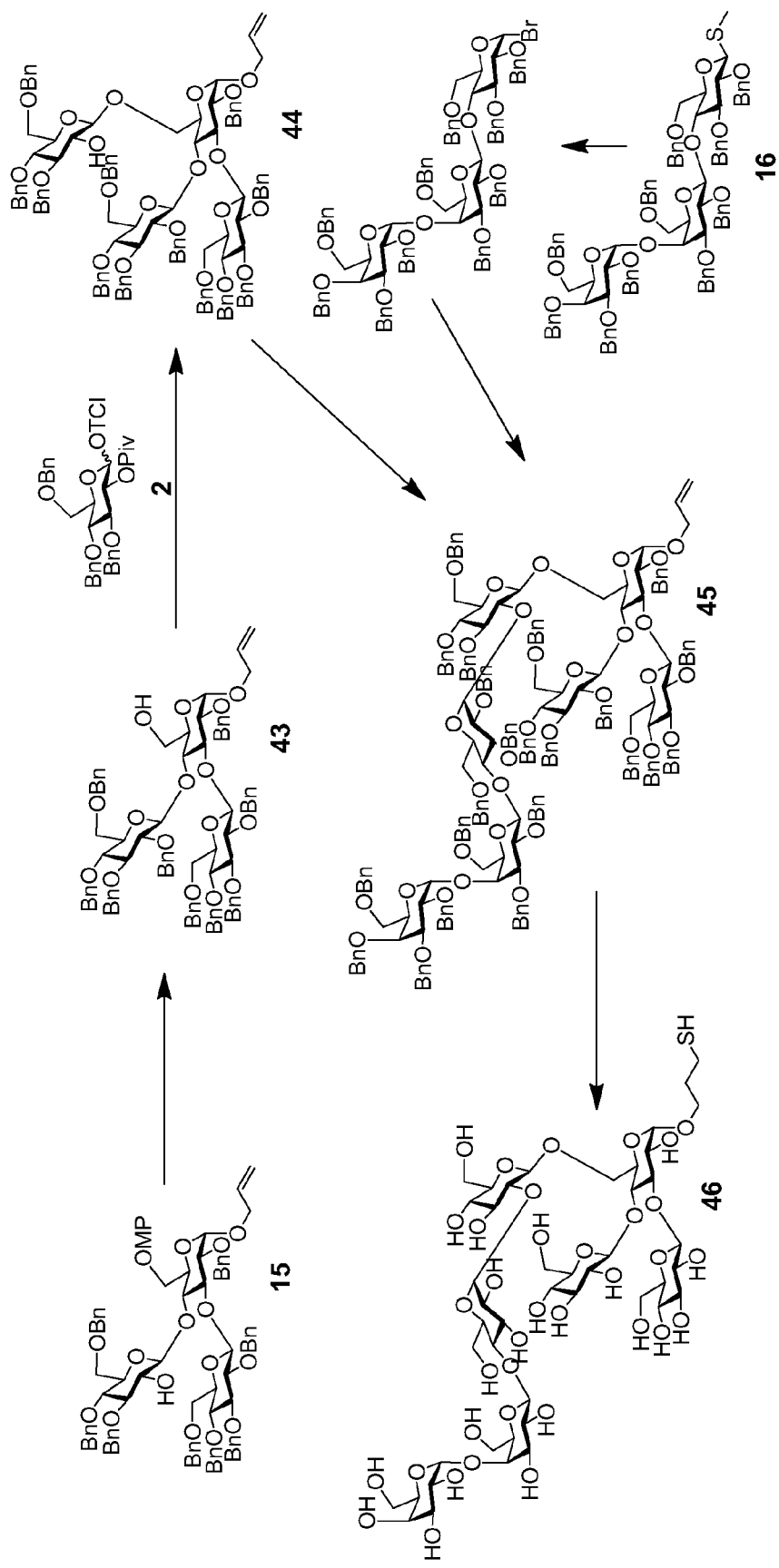
FIGS. 6A and 6B depict reaction schemes for synthesizing a heptamer core 46 (FIG. 6A); and conjugates 47, 48 thereof (FIG. 6B) as described in Example 3.

Synthesis of Heptamer Core 46 (FIG. 6A).

As shown in FIG. 6A, allyl 2-O-benzyl-3-O-(2,3,4,6-tetra-O-benzyl-β-D-glucopyranosyl)-4-O-(3,4,6-tri-O-benzyl-β-D-glucopyanosyl)-6-O-(4-methoxyphenyl)-α-D-glucopyranoside 15 (2.09 g, 1.52 mmol; the synthesis which is described in Example 7 below) was dissolved in a 4:1 solution of THF:NMP (15 mL) and cooled to 0° C. Solid NaH (305 mg of 60% suspension, 7.62 mmol) was added and the mixture was stirred for 10 minutes before the addition of benzyl bromide (300 μL, 6.09 mmol). The reaction mixture was stirred at room temperature for 18 hours, quenched with methanol, stirred for 30 minutes, diluted with ethyl acetate (100 mL), and washed with water and brine (100 mL each). The ethyl acetate solution was dried over $Na_2SO_4$, filtered and concentrated in vacuo. The crude material was purified by silica gel chromatography using toluene/ethyl acetate as the eluent to give the desired trisaccharide (1.62 g, 73%).

The benzylated trisaccharide (721 mg, 0.493 mmol) was taken up in acetonitrile and water (95:5, 18.9 mL) and cooled to 0° C. Ammonium cerium(IV) nitrate (CAN, 811 mg, 1.48 mmol) was added and the reaction mixture was stirred for 4 hours. Ethyl acetate (50 mL) was added and the mixture was washed twice with water, then with brine, dried over $Na_2SO_4$, filtered and concentrated. The crude residue was purified by silica gel chromatography eluting with ethyl acetate in heptane to give the desired trisaccharide alcohol 43 (568 mg, 85%).

Allyl 2-O-benzyl-3-O-(2,3,4,6-tetra-O-benzyl-β-D-glucopyranosyl)-4-O-(2,3,4,6-tetra-O-benzyl-β-D-glucopyanosyl)-α-D-glucopyranoside 43 (502 mg, 0.370 mmol) and 2-pivaloyl,3,4,6-tri-O-benzyl-β-D-glucopyranosyl trichloroacetimidate 2 (501 mg, 0.740 mmol) were dissolved in dry $CH_2Cl_2$ (5.5 mL). Freshly activated AW-300 molecular sieves (0.5 g) were added and the reaction mixture was stirred for 30 minutes and cooled to 0° C. Trimethylsilyl trifluoromethanesulfonate (TMSOTf, 7 μL, 0.0.038 mmol) was added and the reaction stirred for 40 minutes. The reaction mixture was quenched with $Et_3N$ (52 μL), and diluted with $CH_2Cl_2$, filtered through celite and the solvent removed. The crude residue was purified by silica gel chromatography, eluting with heptane:ethyl acetate to give the desired tetrasaccharide coupling product (620 mg, 90%).

The tetrasaccharide coupling product (620 mg, 0.33 mmol) was dissolved in methanol:tetrahydrofuran (1:1, 10 mL) and sodium methoxide solution (1.0 mL, 25% by weight, 4.4 mmol) was added. The solution was stirred at room temperature for 18 hours, then heated to 45° C. for 6 hours, quenched with 1N HCl, diluted with ethyl acetate (100 mL), washed with brine (100 mL), and saturated NaHCO$_3$ (100 mL), dried over Na$_2$SO$_4$, filtered and concentrated. The crude material was purified by silica gel chromatography using ethyl acetate in heptane, to give the desired tetrasaccharide alcohol 44 (447 mg, 67%).

Thiomethyl 4-O-(2,3,6-tri-O-benzyl-4-O-(2,3,4,6-tetra-O-benzyl-α-D-glucopyranosyl)-β-D-galactopyranosyl)-2,3,6-tri-O-benzyl-β-D-glucopyranoside 16(750 mg, 0.522 mmol) (*J. Org. Chem.*, 1996, 61:7711) was dissolved in dry CH$_2$Cl$_2$ (8 mL) under nitrogen and cooled to 0° C. Bromine (66 µL, 1.29 mmol) was added and the reaction mixture stirred for 20 minutes. The reaction was quenched with saturated Na$_2$S$_2$O$_3$ solution (50 mL), and the aqueous layer was extracted with CH$_2$Cl$_2$ (3×50 mL). The combined organic extracts were washed with saturated NaHCO$_3$ and brine, dried over Na$_2$SO$_4$, filtered and concentrated to give the crude glycosyl bromide, which was used without further purification.

The glycosyl bromide and the tetrsaccharide acceptor 44 (825 mg, 0.60 mmol) were combined, 4 Å molecular sieves (700 mg) were added, and the mixture taken up in anhydrous diethyl ether (8 mL) under nitrogen and cooled to −40° C. After stirring for 30 minutes, silver triflate (140 mg, 0.547 mmol) was added and the reaction mixture was stirred for 1 hour. The reaction was quenched at −20° C. by pouring into saturated sodium ascorbate solution (50 mL) and stirring for 30 minutes. The mixture was filtered through celite and the filtrate washed with ethyl acetate (3×50 mL). The organic layer was washed with saturated NaHCO$_3$, brine, dried over Na$_2$SO$_4$, filtered and concentrated. The crude residue was purified by silica gel chromatography using a gradient of ethyl acetate in toluene, to give the desired heptasaccharide 45 (488 mg, 89%).

Heptasaccharide 45 (475 mg, 0.150 mmol) was dissolved in dioxane (6 mL), thioacetic acid (0.5 mL, 7.1 mmol) was added, and the solution purged with argon gas for 10 minutes. The solution was purged with nitrogen gas for 15 minutes before AIBN (50 mg, 0.30 mmol) was added and the reaction mixture heated to 85° C. under an inert atmosphere overnight. The solvent was removed and the crude product was co-evaporated with toluene (2×10 mL). The crude residue was purified by size exclusion chromatography using BioRad SX-1 Bio-Beads (2.5 cm×25 cm column) and toluene as the eluent. Appropriate fractions were combined to give the desired octasaccharide thioacetate product (400 mg, 82%).

Heptasaccharide thioacetate (400 mg, 0.123 mmol) was co-evaporated with toluene (2×10 mL) and dissolved in dry THF (10 mL). In a flame-dried jacketed flask equipped with a dry ice condenser and cooled to −78° C., NH$_3$ gas was condensed into the flask under an Ar atmosphere until the liquid volume reached approximately 30 mL. The heptasaccharide thioacetate solution was transferred by cannula into the liquid NH$_3$. Sodium metal (250 mg, 10.9 mmol) was added under positive Ar gas flow and once a permanent blue color was established the reaction was stirred for another 20 minutes. The reaction was quenched at −78° C. by the addition of saturated NH$_4$Cl solution (10 mL) and warmed to room temperature. N$_2$ was bubbled through the reaction mixture to remove excess NH$_3$, and then the solution was concentrated to dryness. The crude material was purified by size exclusion chromatography on a bed of BioGel P4 (2.5 cm×60 cm column) by elution with water. The fractions containing product were concentrated to yield the desired *Moraxella* heptasaccharide core 46 (45 mg, 30%).

Figure 6B:
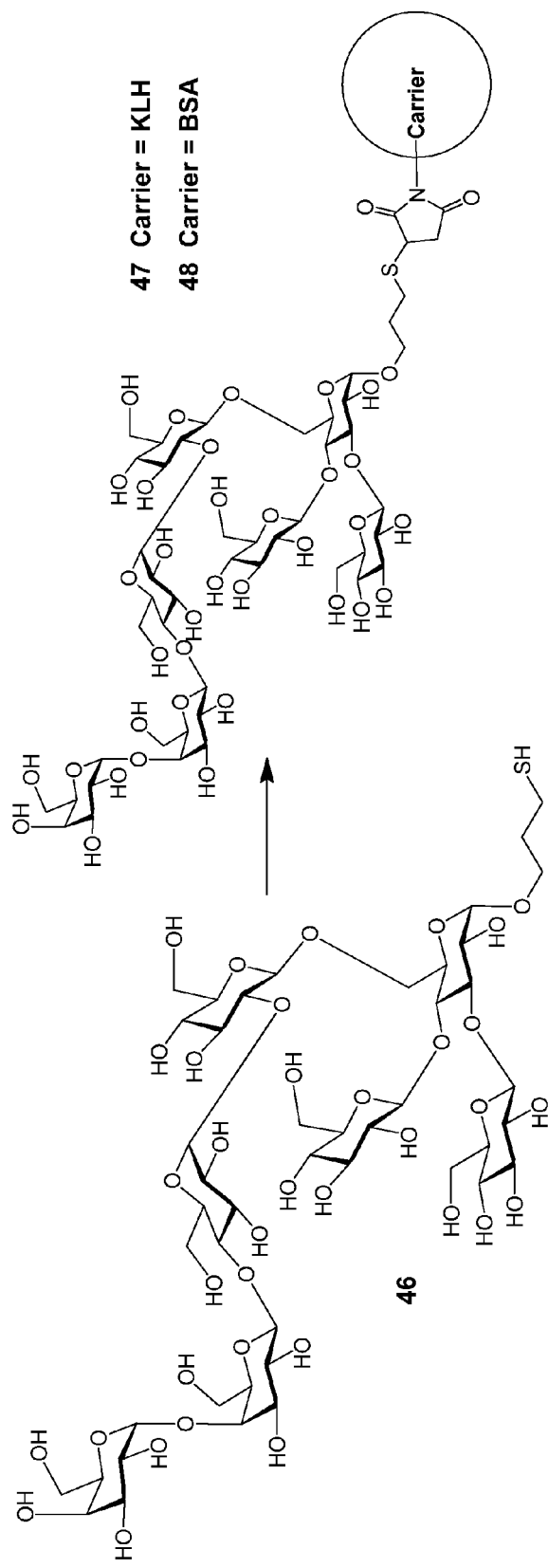

Synthesis of Heptamer Core Conjugates 47, 48 (FIG. 6B).

A solution of tris(2-carboxyethyl)phosphine (TCEP) in water (8.6 µL, 0.05 M, 0.43 µmol) was added to a solution of heptasaccharide thiol 46 in water (12.6 mg/mL, 87 µL, 0.86 µmol), and the resulting solution was stirred for 1 hour. A solution of maleimide-activated keyhole limpet hemocyanin (Imject® KLH, Pierce, Rockford, Ill.) (0.5 mL, 5 mg, ~0.43 µmol maleimide) was added and the resulting solution stirred overnight at room temperature. The reaction mixture was purified by de-salting on D-Salt P-6000 10 mL column (Pierce, Rockford, Ill.). The column was pre-equilibrated with 30 mL of purification buffer (Pierce, Prod. No. 77159), the crude material loaded onto the column and eluted with purification buffer. 1-mL fractions were collected and analyzed for protein content by absorbance at 280 nm (A$_{280}$). Fractions containing protein were combined and lyophilized to give the desired heptasaccharide core-KLH conjugate 47.

A solution of tris(2-carboxyethyl)phosphine (TCEP) in water (30 µL, 0.05 M, 1.5 µmol) was added to a solution of heptasaccharide thiol 46 in water (12.6 mg/mL, 294 µL, 3.0 µmol), and the resulting solution was stirred for 1 hour. A solution of maleimide-activated bovine serum albumin (Imject® BSA, Pierce, 5 mg, ~1.5 µmol maleimide) in Imject® Conjugation Buffer (Pierce, 250 µL diluted with water, 250 µL) was added and the resulting solution stirred overnight at room temperature. The reaction mixture was purified by de-salting on D-Salt P-6000 10 mL column (Pierce, Rockford, Ill.). The column was pre-equilibrated with 30 mL of purification buffer (Pierce, Prod. No. 77159), the crude material loaded onto the column and eluted with purification buffer. 1-mL fractions were collected and analyzed for protein content by absorbance at 280 nm (A$_{280}$). Fractions containing protein were combined and lyophilized to give the desired heptasaccharide core-BSA conjugate 48.

Example 4

Synthesis of Serotype A Octamer and Conjugates thereof

Figure 7A:
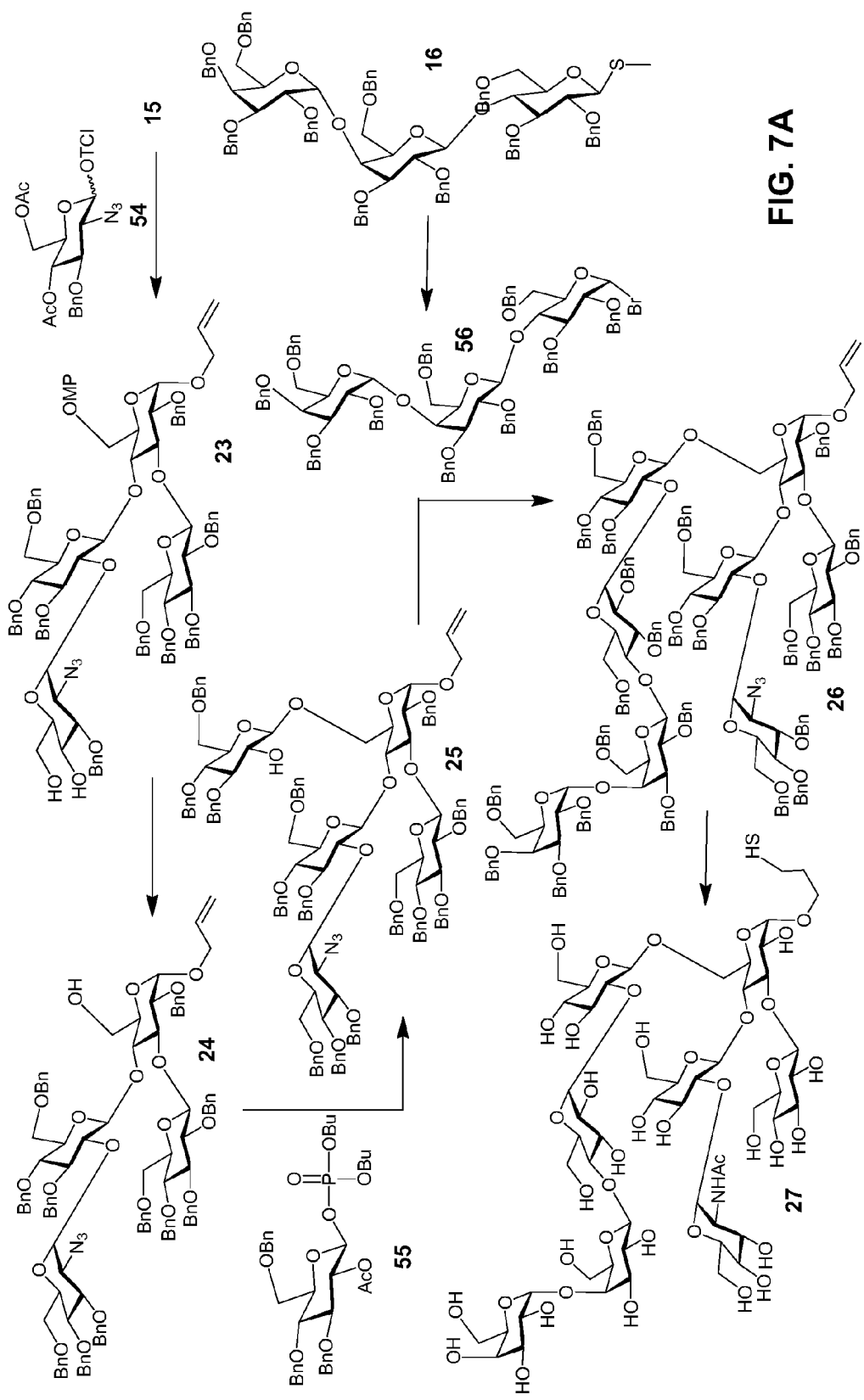
FIGS. 7A and 7B depict reaction schemes for synthesizing a Serotype A octasaccharide 27 (FIG. 7A); and conjugates 28, 29 thereof (FIG. 7B) as described in Example 4.

Synthesis of Serotype A Octamer 27 (FIG. 7A)

Allyl 2-O-benzyl-3-O-(2,3,4,6-tetra-O-benzyl-β-D-glucopyranosyl)-4-O-(3,4,6-tri-O-benzyl-β-D-glucopyranosyl)-6-O-(4-methoxyphenyl)-α-D-glucopyranoside 15 (680 mg, 0.50 mmol) and 2-deoxy-2-azido-3-O-benzyl-4,6-di-O-acetyl-D-glucopyranosyl trichloroacetimidate (525 mg, 1.0 mmol) were combined, co-evaporated with toluene (2×10 mL) and dissolved in dry ether (10 mL). The synthesis of 15 is further described in Example 7 below. Freshly activated AW-300 molecular sieves (1 g) were added and the reaction mixture was stirred for 10 minutes and cooled to 0° C. A solution of trimethylsilyl trifluoromethanesulfonate (TMSOTf, 9 µL, 0.05 mmol) in CH$_2$Cl$_2$ (0.08 mL) was added and the reaction stirred for 45 minutes, at which point the reaction mixture was quenched with Et$_3$N (1 mL), filtered and the solvent removed. The crude coupling product was used without further purification.

The crude tetrasaccharide coupling product was dissolved in methanol:tetrahydrofuran (1:1, 10 mL) and sodium methoxide solution (1.0 mL, 25% by weight, 4.4 mmol) was added. The solution was stirred at room temperature for 18 hours, diluted with ethyl acetate (100 mL), quenched with 1N HCl, washed with brine (100 mL), and saturated NaHCO$_3$ (100 mL), dried over MgSO$_4$, filtered and concentrated. The crude material was purified on a silica gel column (80 g) using an ISCO automated chromatography system, eluting with a 0→40% gradient of ethyl acetate in toluene, to give the desired tetrasaccharide diol 23 (470 mg, 57%) plus, separately, the corresponding β-anomer (100 mg, 12%).

Tetrasaccharide diol 23 (635 mg, 0.385 mmol) was co-evaporated with toluene (2×5 mL) before being taken up in a 4:1 solution of NMP:THF (10 mL) and cooled to 0° C. Solid NaH (46 mg of 60% suspension, 1.16 mmol) was added and the mixture was stirred for 10 minutes before the benzyl bromide (114 µL, 0.96 mmol) was added. The reaction mixture was stirred at room temperature for 18 hours, quenched with methanol, diluted with ethyl acetate (50 mL), washed with 1 N HCl, brine, and saturated NaHCO$_3$ (50 mL each). The ethyl acetate solution was dried over Na$_2$SO$_4$, filtered and concentrated in vacuo. The crude material was purified on a silica gel column (40 g) using an ISCO automated chromatography system, eluting with a 0→60% gradient of ethyl acetate in heptane, to give the desired tetrasaccharide (600 mg, 85%).

The tetrasaccharide (600 mg, 0.328 mmol) was taken up in acetonitrile and water (4:1, 15 mL) and cooled to 0° C. Ammonium cerium(IV) nitrate (CAN, 540 mg, 0.984 mmol) was added and the reaction mixture was stirred for 2 hours. The reaction was quenched with Et$_3$N (2 mL), filtered through a small pad of celite, and washed twice with CH$_2$Cl$_2$ (50 mL). The organics were combined, dried over Na$_2$SO$_4$, filtered and concentrated. The crude material was purified on a silica gel column (40 g) using an ISCO automated chromatography system, eluting with a 0→75% gradient of ethyl acetate in heptane, to give the desired tetrasaccharide alcohol 24 (410 mg, 73%).

Tetrasaccharide acceptor 24 (410 mg, 0.24 mmol) and di-n-butylphosphoryl 2-O-acetyl-3,4,6-tri-O-benzyl-β-D-glucopyranoside X (210 mg, 0.29 mmol) were combined, co-evaporated with toluene (3×5 mL), dissolved in dry CH$_2$Cl$_2$ (5 mL) and cooled under nitrogen to −30° C. The reaction mixture was stirred for 10 minutes before trimethylsilyl trifluoromethanesulfonate (TMSOTf, 53 µL, 0.29 mmol) was added. The reaction mixture was stirred for 30 minutes then quenched with Et$_3$N (2 mL), and the solvent removed to give the crude coupling product, which was used without further purification.

The crude coupling product was dissolved in methanol:tetrahydrofuran (2:1, 15 mL) and sodium methoxide solution (5.0 mL, 25% by weight, 22 mmol) was added. The solution was stirred at room temperature for 18 hours and concentrated in vacuo. The residue was partitioned between ethyl acetate (150 mL) and saturated NH$_4$Cl (100 mL), washed with brine (2×100 mL), dried over MgSO$_4$, filtered and concentrated. The crude material was purified on a silica gel column (80 g) using an ISCO automated chromatography system, eluting with a 0→60% gradient of ethyl acetate in heptane, to give the desired pentasaccharide alcohol 25 (375 mg, 73%).

Thiomethyl 4-O-(2,3,6-tri-O-benzyl-4-O-(2,3,4,6-tetra-O-benzyl-α-D-glucopyranosyl)-β-D-galactopyranosyl)-2,3,6-tri-O-benzyl-β-D-glucopyranoside 16(800 mg, 0.557 mmol) (*J. Org. Chem.* 61 (1996) 7711) was co-evaporated with toluene (3×5 mL) then dissolved in dry CH$_2$Cl$_2$ (5 mL) under nitrogen and cooled to 0° C. Bromine (30 µL, 0.585 mmol) was added and the reaction mixture was stirred for 10 minutes. Dry toluene (10 mL) was added and removed in vacuo. The toluene azeotrope was repeated three times to give the crude glycosyl bromide, which was used without further purification.

The glycosyl bromide and the pentasaccharide acceptor 25 (336 mg, 0.156 mmol) were combined and co-evaporated with toluene (3×5 mL). Freshly activated 4 Å molecular sieves (1 g, Linde 600 mesh) were added followed by anhydrous diethyl ether (10 mL) under nitrogen. The mixture was cooled to −40° C. and after 30 minutes silver triflate (143 mg, 0.557 mmol) was added and the reaction mixture was stirred for 30 minutes. The reaction was quenched at −20° C. with Et$_3$N (0.4 mL), diluted with CH$_2$Cl$_2$ (50 mL) and filtered through celite and the filtrate washed with CH$_2$Cl$_2$ (50 mL). The filtrate was stirred with saturated sodium ascorbate solution for 1 hour then filtered through celite. The filtrate was washed with saturated NaHCO$_3$ (100 mL), brine (100 mL), dried over Na$_2$SO$_4$, filtered and concentrated. The crude residue was purified by silica gel chromatography using toluene:ethyl acetate as the eluent to give the desired Serotype A octasaccharide 26(335 mg, 60%).

Octasaccharide 26 (280 mg, 0.079 mmol) was dissolved in dioxane (10 mL), thioacetic acid (1.0 mL, 14 mmol) and AIBN (60 mg, 0.36 mmol) were added, and the solution purged with nitrogen gas for 15 minutes. The reaction mixture heated to 75° C. under an inert atmosphere for 18 hours, cooled to room temperature and quenched with cyclohexene (0.1 mL). The solvent was removed and the crude product was purified by size exclusion chromatography using BioRad SX-1 Bio-Beads (2.5 cm×60 cm column) and toluene as the eluent to give the desired octaccharide thioacetate (221 mg, 77%).

The octasaccharide thioacetate (26.1 mg, 7.2 µmol) was dissolved in DMF (3 mL) and ethanol (1.5 mL), and the solution was purged with nitrogen for 5 minutes. Benzyl chloride (30 µL, 0.26 mmol) and 1.0 M NaOH (0.1 mL) were added, and the reaction mixture was stirred for 1 hour. The mixture was diluted with ethyl acetate (50 mL), washed with water (2×50 mL) and brine (2×50 mL), dried over Na$_2$SO$_4$, filtered and concentrated to a yellow oil (26 mg, 98%), which was used without further purification.

Octasaccharide benzyl thioether (26 mg, 7.1 µmol) was dissolved in dry THF (2 mL). In a flame-dried jacketed flask equipped with a dry ice condenser and cooled to −78° C., NH$_3$ gas was condensed into the flask under an Ar atmosphere until the liquid volume reached approximately 15 mL. The octasaccharide benzyl thioether solution was transferred into the liquid NH$_3$. Sodium metal (20 mg, 0.87 mmol) was added under positive Ar gas flow and stirred for 10 minutes. The reaction was quenched at −78° C. by the addition of saturated NH$_4$Cl solution (0.1 mL) and warmed to room temperature. N$_2$ was bubbled through the reaction mixture to remove excess NH$_3$, and then the solution was concentrated to dryness. The crude material was purified by size exclusion chromatography on a bed of Sephadex G-10(2.5 cm×8 cm column) by elution with water. The fractions containing product were concentrated to yield the crude octasaccharide (10 mg, quantitative).

The crude octasaccharide (10 mg) was dissolved in water (0.6 mL) and methanol (0.3 mL), solid NaHCO$_3$ (20 mg), and acetic anhydride (20 µL) were added. The reaction mixture was stirred for 2 hours then loaded directly onto a Sephadex G-10 column (2.5 cm×8 cm) and eluted with water. Lyophilization of the appropriate fractions gave the desired *Moraxella* serotype A octasaccharide 27 (5.2 mg, 50%).

Figure 7B:
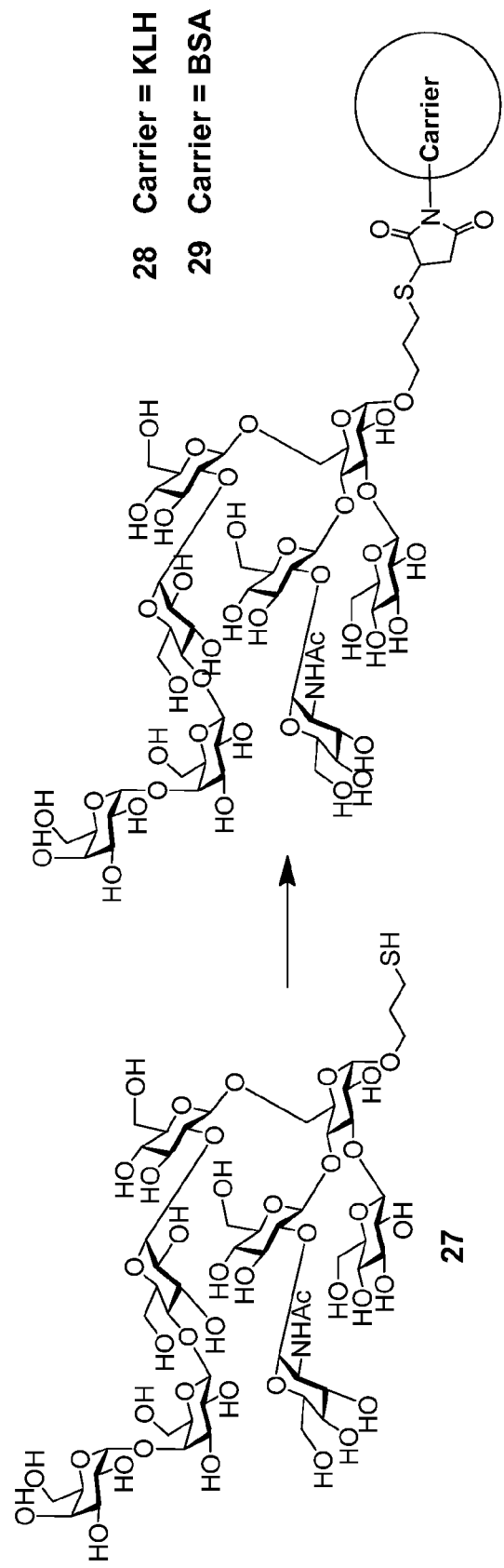

Synthesis of Serotype A Octamer Conjugates 28, 29 (FIG. 7B)

First, a conjugation stock solution of octasaccharide 27 was prepared as follows. The octasaccharide 27 (5.5 mg, 3.85 μmol) was dissolved in water (0.5 mL). Hydrazine in water (520 μL, 0.05 M, 60 μL) was added to the reaction mixture, was stirred at room temperature for 1 hour and concentrated in vacuo. The residue was co-evaporated with water (3×1 mL) and redissolved in water (300 μL). A solution of tris(2-carboxyethyl)phosphine (TCEP) in water (39 μL, 0.05 M, 1.95 μmol) was added and stirred for 1 hour. Imject® Conjugation Buffer (Pierce, 300 μL) was added to provide a stock solution for conjugation to KLH and BSA.

To synthesize the KLH conjugate 28, conjugation stock solution of octasaccharide thiol 27 (140 μL, 0.86 μmol) was added to a solution of maleimide-activated keyhole limpet hemocyanin (Imject® KLH, Pierce, Rockford, Ill.) (5 mg, ~0.43 μmol maleimide) in water (0.5 mL) was added and the resulting solution stirred overnight at room temperature. The reaction mixture was purified by de-salting on D-Salt P-6000 10 mL column (Pierce, Rockford, IL). The column was pre-equilibrated with 30 mL of purification buffer (Pierce, Prod. No. 77159), the crude material loaded onto the column and eluted with purification buffer. 1-mL fractions were collected and analyzed for protein content by absorbance at 280 nm ($A_{280}$). Fractions containing protein were combined and lyophilized to give the desired serotype A octamer-KLH conjugate 28.

To synthesize the BSA conjugate 29, conjugation stock solution of octasaccharide thiol 37 (500 μL, 3.0 μmol) was added to a solution of maleimide-activated bovine serum albumin (Imject® BSA, Pierce, Rockford, Ill.) (5 mg, ~1.5 μmol maleimide) in Imject® Conjugation Buffer (Pierce, 300 μL diluted with water, 300 μL) and the resulting solution stirred for 18 hours at room temperature. The reaction mixture was purified by de-salting on D-Salt P-6000 10 mL column (Pierce, Rockford, Ill.). The column was pre-equilibrated with 30 mL of purification buffer (Pierce, Prod. No. 77159), the crude material loaded onto the column and eluted with purification buffer. 1-mL fractions were collected and analyzed for protein content by absorbance at 280 nm ($A_{280}$). Fractions containing protein were combined and lyophilized to give the desired serotype A octamer-BSA conjugate 29.

Example 5

Synthesis of Serotype B7 Hexasaccharide Core and Conjugates thereof

Figure 8A:
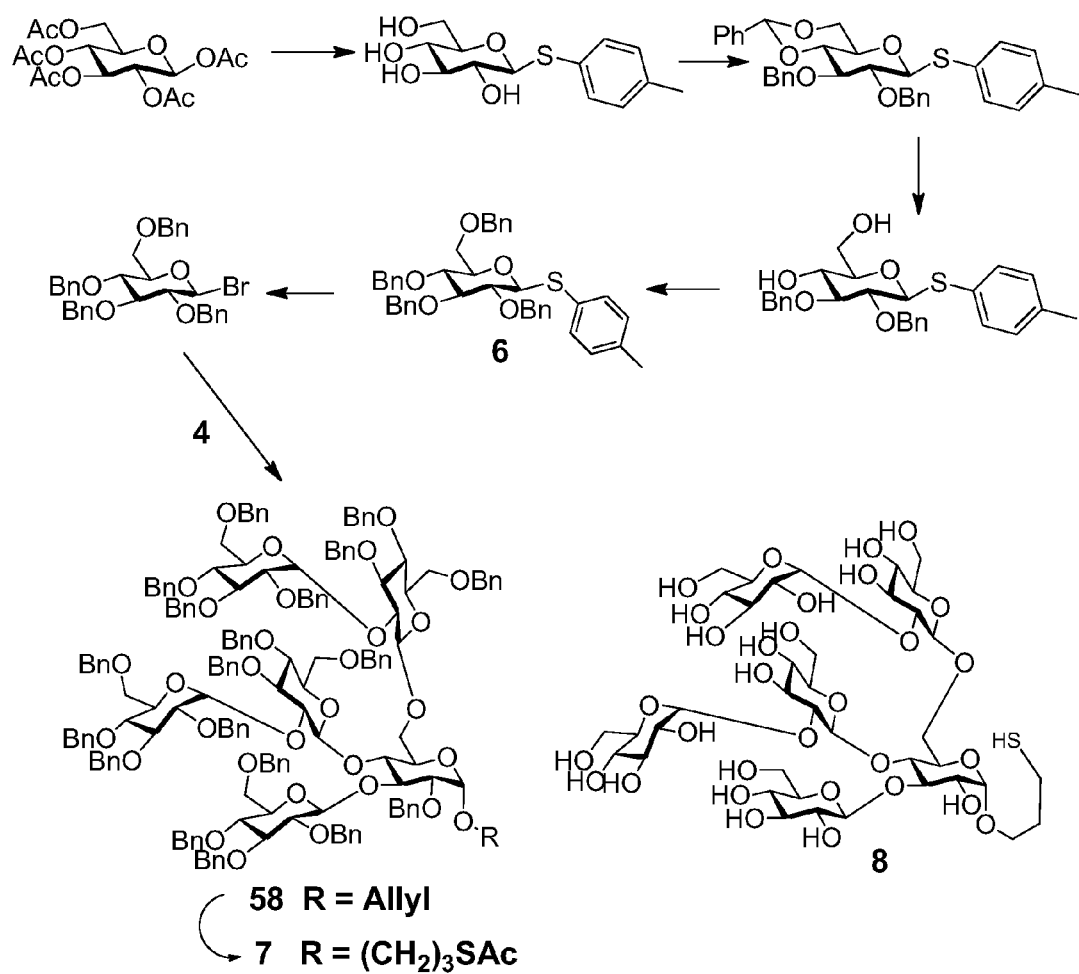
FIGS. 8A and 8B depict reaction schemes for synthesizing a Serotype B7 hexasaccharide 8 (FIG. 8A); and conjugates 9, 41 thereof (FIG. 8B) as described in Example 5.

Synthesis of Serotype 87 Hexasaccharide Core 8 (FIG. 8A)

In a jacketed 4-L flask D-Glucose-penta-O-acetate (1.0 kg, 2.56 mol) was dissolved in $CH_2Cl_2$ (3 L) and p-thiocresol (350.2 g, 2.82 mol) was added. The stirred solution was brought to 5° C. and tin(IV) chloride (500 g, 1.9 mol) was added slowly while maintaining an internal temperature of <10° C. The reaction mixture was stirred overnight at 20° C. The reaction was quenched by transferring the mixture into ice water (4 L). The $CH_2Cl_2$ layer was washed with saturated $NaHCO_3$ (2 L), which was back-extracted with $CH_2Cl_2$ (0.5 L). The combined organic layers were washed with water (3×2 L) then evaporated to a thick syrup. 2-Propanol (4 L) was added and the suspension heated to 70° C. until a clear solution resulted. The solution was allowed to cool with stirring over 2 days. The solids were filtered, washed with 2-propanol and dried in vacuo to give p-thiophenyl 2,3,4,6-tetra-O-acetyl-β-D-glucopyranoside (595 g, 51%).

p-Thiophenyl 2,3,4,6-tetra-O-acetyl-β-D-glucopyranoside (100 g, 0.22 mol) was dissolved in anhydrous methanol (500 mL) and sodium methoxide in methanol (5 mL, 25% solution by weight, 22 mmol) was added. The solution was stirred at room temperature for 2 hours then was quenched with A-15 ($H^+$) resin (10 g), filtered and concentrated to give the desired product as a crude syrup (56 g), which was used without further purification p-Thiophenyl β-D-glucopyranoside (56 g, 0.2 mol) was dissolved in acetonitrile (250 mL). to this stirred solution were added benzaldehyde dimethylacetal (60 mL, 0.41 mol) and (+/−)-camphor-10-sulfonic acid (12 g, 0.05 mol) and the solution was stirred at room temperature overnight. The solvent was removed and the crude product crystallized from hot ethanol to give p-thiophenyl 4,6-O-benzylidene-β-D-glucopyranoside (38 g, 52%).

p-Thiophenyl 4,6-O-benzylidene-β-D-glucopyranoside (85 g, 0.23 mol) was dissolved in dry NMP:THF (3:7, 500 mL) and cooled to 0° C. with stirring. Solid NaH (24 g of 60% suspension, 0.6 mol) was added slowly and the mixture was stirred for 15 minutes. Benzyl bromide (68 mL, 0.57 mol) was added slowly to keep the internal temperature below 20° C. The reaction mixture was stirred at room temperature overnight, quenched with methanol (10 mL) before diluting with ethyl acetate (1 L) and water (500 mL). The organic layer was washed with water (3×500 mL) and concentrated to a solid. The solid was recrystallized from hot tert-butyl methyl ether (300 mL) to give p-thiophenyl 2,3-di-O-benzyl-4,6-O-benzylidene-β-D-glucopyranoside (86g).

p-Thiophenyl 2,3-di-O-benzyl-4,6-O-benzylidene-β-D-glucopyranoside (8.4 g, 15 mmol) was dissolved in $CH_2Cl_2$ (300 mL), a solution of trifluoroacetic acid (8.4 mL) in water (5.6 mL) was added, and the resulting mixture was stirred at room temperature for 4 hours. The reaction was quenched with saturated $NaHCO_3$ solution (150 mL), and the organic layer was dried over $Na_2SO_4$, filtered and concentrated. The crude residue was purified by dissolving in a minimum volume of $CH_2Cl_2$ and passing it through a silica plug, eluting with ethyl acetate:heptane (1:9) then ethyl acetate:heptane (3:2) to give p-thiophenyl 2,3-di-O-benzyl-β-D-glucopyranoside (5.3 g, 75%).

p-Thiophenyl 2,3-di-O-benzyl-β-D-glucopyranoside (6.0 g, 13 mmol) was dissolved in dry NMP:THF (1:4, 100 mL) and cooled to 0° C. with stirring. Solid NaH (1.55 g of 60% suspension, 39 mmol) was added slowly and the mixture was stirred for 15 minutes. Benzyl bromide (3.8 mL, 32 mmol) was added slowly to keep the internal temperature below 20° C. The reaction mixture was stirred at room temperature overnight, quenched with methanol (10 mL) before diluting with ethyl acetate (150 mL). The organic layer was washed with 1 N HCl (100 mL), brine (100 mL) and saturated $NaHCO_3$ solution (100 mL), dried over $MgSO_4$, filtered and concentrated. The solid was purified on a silica gel column (120 g) using an ISCO automated chromatography system, eluting with a 0→40% gradient of ethyl acetate in heptane, to give the desired p-thiophenyl 2,3,4,6-tetra-O-benzyl-β-D-glucopyranoside 6 (4.66 g, 55%).

p-Thiophenyl 2,3,4,6-tetra-O-benzyl-β-D-glucopyranoside 6 (4.66 g, 7.2 mmol) was co-evaporated with toluene (2×10 mL) then dissolved in dry $CH_2Cl_2$ (50 mL) under nitrogen and cooled to 0° C. Bromine (465 μL, 18 mmol) was added and the reaction mixture stirred for 15 minutes. The reaction was quenched with saturated $Na_2S_2O_3$ solution (50 mL), and the aqueous layer was extracted with $CH_2Cl_2$ (3×50 mL). The combined organic extracts were dried over $Na_2SO_4$, filtered and concentrated to give the crude glucosyl bromide, which was used without further purification.

The glucosyl bromide and the tetrasaccharide diol acceptor 4 (2.0 g, 1.2 mmol) were combined and co-evaporated with toluene (2×10 mL), taken up in anhydrous diethyl ether (50 mL) under nitrogen and cooled to −50° C. Silver triflate (1.85 g, 7.2 mmol) was added and the reaction mixture was stirred for 1 hour. The reaction was quenched by the addition of saturated sodium ascorbate solution (25 mL) and stirring for 1 hour. The mixture was filtered through celite and concentrated to dryness. The crude residue was purified by size exclusion chromatography using BioRad SX-1 Bio-Beads (4 cm×40 cm column) and toluene as the eluent. The fractions containing hexasaccharide were further purified on a silica gel column (40 g) using an ISCO automated chromatography system, eluting with a 0→80% gradient of ethyl acetate in heptane, to give the desired hexasaccharide 7 (2.6 g, 79%).

Hexasaccharide 7 (1.05 g, 0.383 mmol) was co-evaporated with toluene (10 mL), dissolved in dioxane (12 mL) under $N_2$, and thioacetic acid (1.0 mL, 14.2 mmol) was added. The solution was purged with nitrogen gas for 15 minutes before AIBN (100 mg, 0.61 mmol) was added and the reaction mixture heated to 80° C. under an inert atmosphere for 3 hours then overnight at room temperature. The solvent was removed and the crude product was co-evaporated with toluene. The crude residue was purified by size exclusion chromatography using BioRad SX-1 Bio-Beads (2.5 cm×25 cm column) and toluene as the eluent. The fractions containing purified hexasaccharide were further purified on a silica gel column (40 g) using an ISCO automated chromatography system, eluting with a 0→75% gradient of ethyl acetate in heptane, to give the desired hexasaccharide (350 mg, 32%). Mixed fractions were reprocessed through Bio-Beads and silica gel chromatography to yield more of the desired hexasaccharide thioacetate product.

Hexasaccharide thioacetate (330 mg, 0.117 mmol) was coevaporated with toluene (2×10 mL) and dissolved in dry THF (5 mL). In a jacketed flask equipped with a dry ice condenser and cooled to −78° C., $NH_3$ gas was condensed into the flask under an Ar atmosphere until the liquid volume reached approximately 20 mL. The hexasaccharide thioacetate solution was transferred by cannula into the liquid $NH_3$. Sodium metal (250 mg, 10.9 mmol) was added under positive Ar gas flow and once a permanent blue color was established the reaction was stirred for another 20 minutes. The reaction was quenched at −78° C. by the addition of saturated $NH_4Cl$ solution (10 mL) and warmed to room temperature. $N_2$ was bubbled through the reaction mixture to remove excess $NH_3$, and then the solution was concentrated to 2 mL. The crude material was purified by size exclusion chromatography on a bed of BioGel P4 (2.5 cm×50 cm column) by elution with water. The fractions containing product were concentrated to yield the desired *Moraxella* Serotype B7 hexasaccharide core 8 (104 mg, 83%).

Figure 8B:
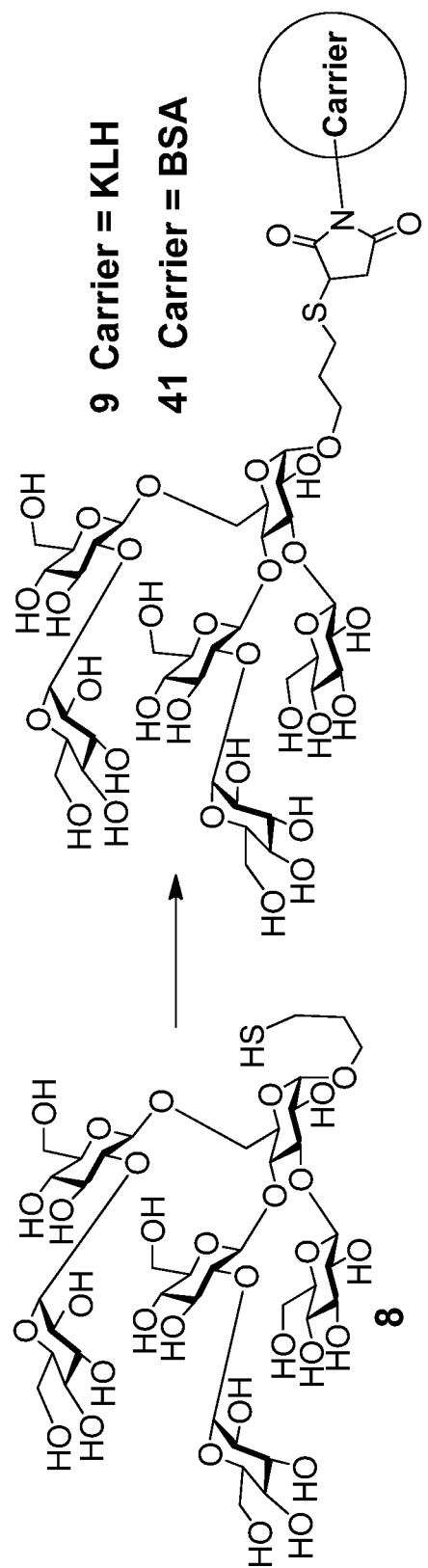

Synthesis of Serotype 87 Hexasaccharide Core Conjugates 9, 41 (FIG. 8B)

To synthesize the KLH conjugate 9, a solution of tris(2-carboxyethyl)phosphine (TCEP) in water (8.6 µL, 0.05 M, 0.43 µmol) was added to a solution of hexasaccharide thiol 8 in water (15.6 mg/mL, 58 µL, 0.86 µmol), and the resulting solution was stirred for 1 hour. A solution of maleimide-activated keyhole limpet hemocyanin (Imject® KLH, Pierce, Rockford, Ill.) (0.5 mL, 5 mg, ~0.43 µmol maleimide) was added and the resulting solution stirred overnight at room temperature. The reaction mixture was purified by de-salting on D-Salt P-6000 10 mL column (Pierce, Rockford, Ill.). The column was pre-equilibrated with 30 mL of purification buffer (Pierce, Prod. No. 77159), the crude material loaded onto the column and eluted with purification buffer. 1-mL fractions were collected and analyzed for protein content by absorbance at 280 nm ($A_{280}$). Fractions containing protein were combined and lyophilized to give the desired serotype B7 hexamer-KLH conjugate 9.

To synthesize the BSA conjugate 41, a solution of tris(2-carboxyethyl)phosphine (TCEP) in water (30 µL, 0.05 M, 1.5 µmol) was added to a solution of hexasaccharide thiol 8 in water (15.6 mg/mL, 205 µL, 3.0 µmol), and the resulting solution was stirred for 1 hour. A solution of maleimide-activated bovine serum albumin (Imject® BSA, Pierce, 5 mg, ~1.5 µmol maleimide) in Imject® Conjugation Buffer (Pierce, 250 µL diluted with water, 250 µL) was added and the resulting solution stirred overnight at room temperature. The reaction mixture was purified by de-salting on D-Salt P-6000 10 mL column (Pierce, Rockford, Ill.). The column was pre-equilibrated with 30 mL of purification buffer (Pierce, Prod. No. 77159), the crude material loaded onto the column and eluted with purification buffer. 1-mL fractions were collected and analyzed for protein content by absorbance at 280 nm ($A_{280}$). Fractions containing protein were combined and lyophilized to give the desired serotype B7 hexamer-BSA conjugate 41.

Example 6

Synthesis of Serotype 89 Octamer and Conjugates thereof

Figure 9:
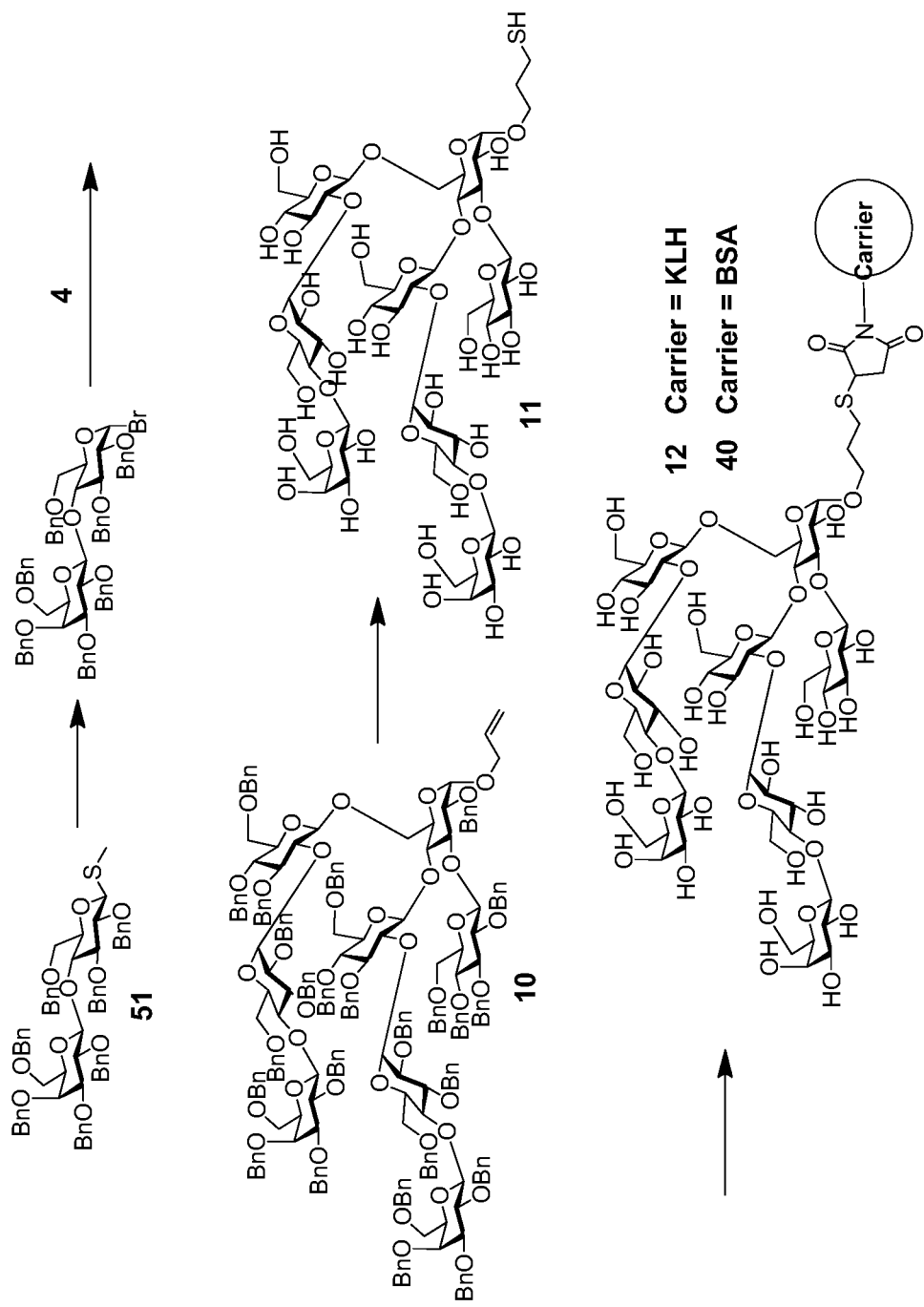
FIG. 9 depicts a reaction scheme for synthesizing a Serotype B9 octasaccharide 11 and conjugates 12, 40 thereof as described in Example 6.

Synthesis of Serotype 89 Octamer 10 (FIG. 9)

Thiomethyl 4-O-(2,3,4,6-tetra-O-benzyl-β-D-galactopyranosyl)-2,3,6-tri-O-benzyl-β-D-glucopyranoside 51 (2.76 g, 2.95 mmol) (*J. Org. Chem.* 61 (1996) 7711) was co-evaporated with toluene (2×10 mL) then dissolved in dry $CH_2Cl_2$ (30 mL) under nitrogen and cooled to 0° C. Bromine (191 µL, 7.4 mmol) was added and the reaction mixture stirred for 10 minutes. The reaction was quenched with saturated $Na_2S_2O_3$ solution (50 mL), and the aqueous layer was extracted with $CH_2Cl_2$ (3×50 mL). The combined organic extracts were dried over $Na_2SO_4$, filtered and concentrated to give the crude glucosyl bromide, which was used without further purification.

The glycosyl bromide and the tetrasaccharide diol acceptor 4 (0.50 g, 0.30 mmol) were combined and co-evaporated with toluene (2×10 mL), taken up in anhydrous diethyl ether (10 mL) under nitrogen and cooled to −40° C. Silver triflate (0.760 g, 2.95 mmol) was added and the reaction mixture was stirred for 1 hour. The reaction was quenched by pouring into saturated sodium ascorbate solution (25 mL) and stirring for 30 minutes. The mixture was filtered through celite and the filtrate washed with ethyl acetate (3×50 mL). The organic layer was washed with brine, dried over $Na_2SO_4$, filtered and concentrated. The crude residue was purified by size exclusion chromatography using BioRad SX-1 Bio-Beads (2.5 cm×50 cm column) and toluene as the eluent. The fractions containing octasaccharide were further purified twice on a silica gel column (80 g) using an ISCO automated chromatography system, eluting with a 0→20% gradient of ethyl acetate in heptane, to give the desired octasaccharide 10 (0.250 g, 24%).

Octasaccharide 10 (0.25 g, 0.069 mmol) was dissolved in dioxane (6 mL), thioacetic acid (0.5 mL, 7.1 mmol) was added, and the solution purged with argon gas for 10 minutes. The solution was purged with nitrogen gas for 15 minutes before AIBN (50 mg, 0.30 mmol) was added and the reaction mixture heated to 75° C. under an inert atmosphere overnight.

A second aliquot of AIBN (25 mg, 0.15 mmol) was added and the reaction mixture was heated until the reaction was complete.

The solvent was removed and the crude product was co-evaporated with toluene (2×10 mL). The crude residue was purified by size exclusion chromatography using BioRad SX-1 Bio-Beads (2.5 cm×25 cm column) and toluene as the eluent. Appropriate fractions were combined to give the desired octasaccharide thioacetate product (225 mg, 88%).

Octasaccharide thioacetate (220 mg, 0.060 mmol) was co-evaporated with toluene (2×10 mL) and dissolved in dry THF (5 mL). In a flame-dried jacketed flask equipped with a dry ice condenser and cooled to −78° C., $NH_3$ gas was condensed into the flask under an Ar atmosphere until the liquid volume reached approximately 10 mL. The octasaccharide thioacetate solution was transferred by cannula into the liquid $NH_3$. Sodium metal (250 mg, 10.9 mmol) was added under positive Ar gas flow and once a permanent blue color was established the reaction was stirred for another 20 minutes. The reaction was quenched at −78° C. by the addition of saturated $NH_4Cl$ solution (10 mL) and warmed to room temperature. $N_2$ was bubbled through the reaction mixture to remove excess $NH_3$, and then the solution was concentrated to dryness. The crude material was purified by size exclusion chromatography on a bed of BioGel P4 (2.5 cm×60 cm column) by elution with water. The fractions containing product were concentrated to yield the desired *Moraxella* serotype B9 octasaccharide 11 (20 mg, 24%).

Synthesis of Serotype 89 Octamer Conjugates 12, 40 (FIG. 9)

To synthesize the KLH conjugate 12, a solution of tris(2-carboxyethyl)phosphine (TCEP) in water (8.6 µL, 0.05 M, 0.43 µmol) was added to a solution of octasaccharide thiol 11 in water (15.4 mg/mL, 79 µL, 0.86 µmol), and the resulting solution was stirred for 1 hour. A solution of maleimide-activated keyhole limpet hemocyanin (Imject® KLH, Pierce, Rockford, Ill.) (0.5 mL, 5 mg, ~0.43 µmol maleimide) was added and the resulting solution stirred overnight at room temperature. The reaction mixture was purified by de-salting on D-Salt P-6000 10 mL column (Pierce, Rockford, Ill.). The column was pre-equilibrated with 30 mL of purification buffer (Pierce, Prod. No. 77159), the crude material loaded onto the column and eluted with purification buffer. 1-mL fractions were collected and analyzed for protein content by absorbance at 280 nm ($A_{280}$). Fractions containing protein were combined and lyophilized to give the desired serotype B9 octamer-KLH conjugate 12.

To synthesize the BSA conjugate 40, a solution of tris(2-carboxyethyl)phosphine (TCEP) in water (30 µL, 0.05 M, 1.5 µmol) was added to a solution of octasaccharide thiol 11 in water (15.4 mg/mL, 276 µL, 3.0 µmol), and the resulting solution was stirred for 1 hour. A solution of maleimide-activated bovine serum albumin (Imject® BSA, Pierce, 5 mg, ~1.5 µmol maleimide) in Imject® Conjugation Buffer (Pierce, 250 µL diluted with water, 250 µL) was added and the resulting solution stirred overnight at room temperature. The reaction mixture was purified by de-salting on D-Salt P-6000 10 mL column (Pierce, Rockford, Ill.). The column was pre-equilibrated with 30 mL of purification buffer (Pierce, Prod. No. 77159), the crude material loaded onto the column and eluted with purification buffer. 1-mL fractions were collected and analyzed for protein content by absorbance at 280 nm ($A_{280}$). Fractions containing protein were combined and lyophilized to give the desired serotype B9 octamer-BSA conjugate 40.

Example 7

Synthesis of Serotype B11 Decamer and Conjugates thereof

Figure 10A:
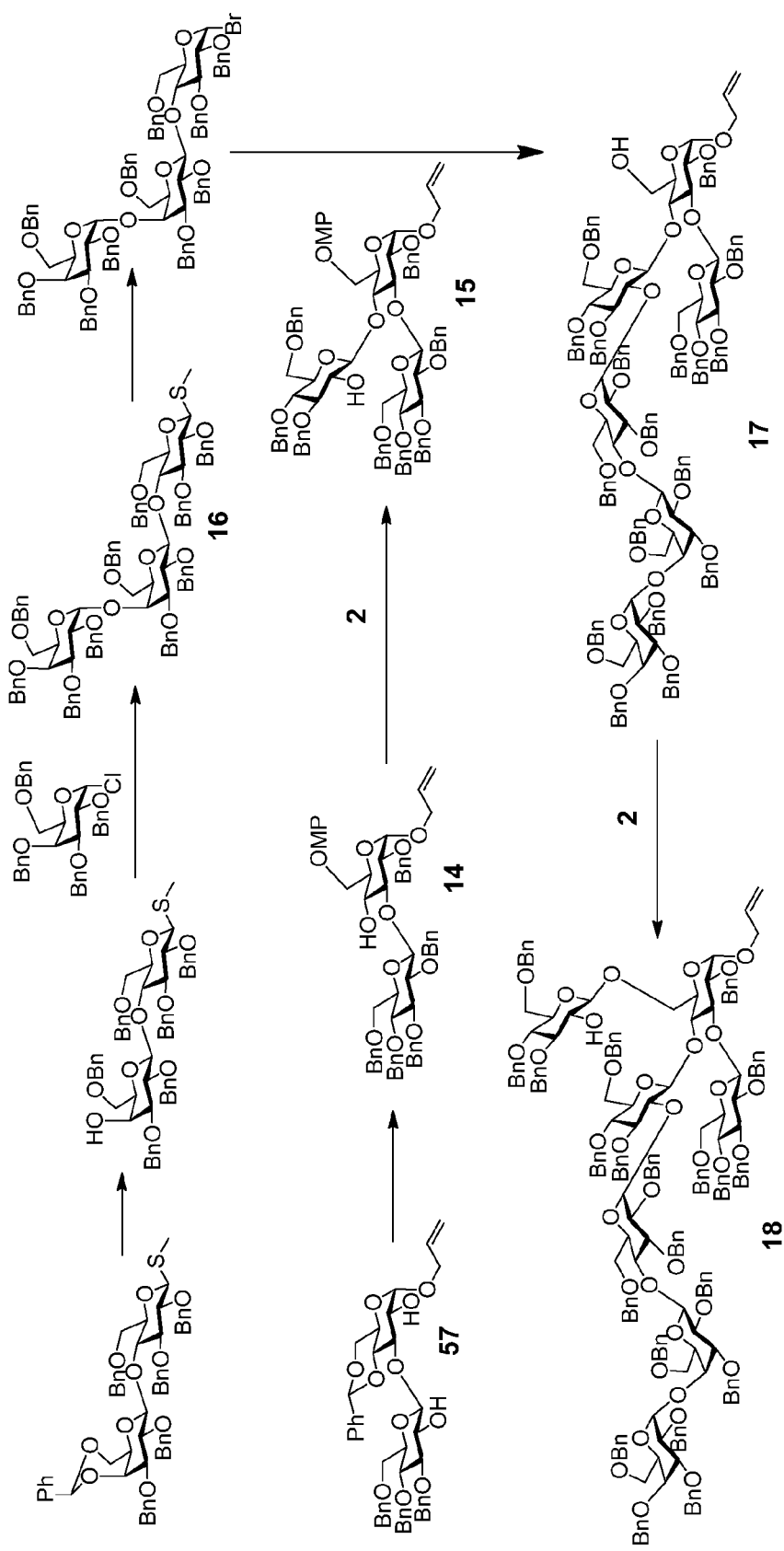
FIGS. 10A and 10B depict a reaction scheme for synthesizing a Serotype B11 decasaccharide 20 and conjugates 21, 22 thereof as described in Example 7.
Figure 10B:
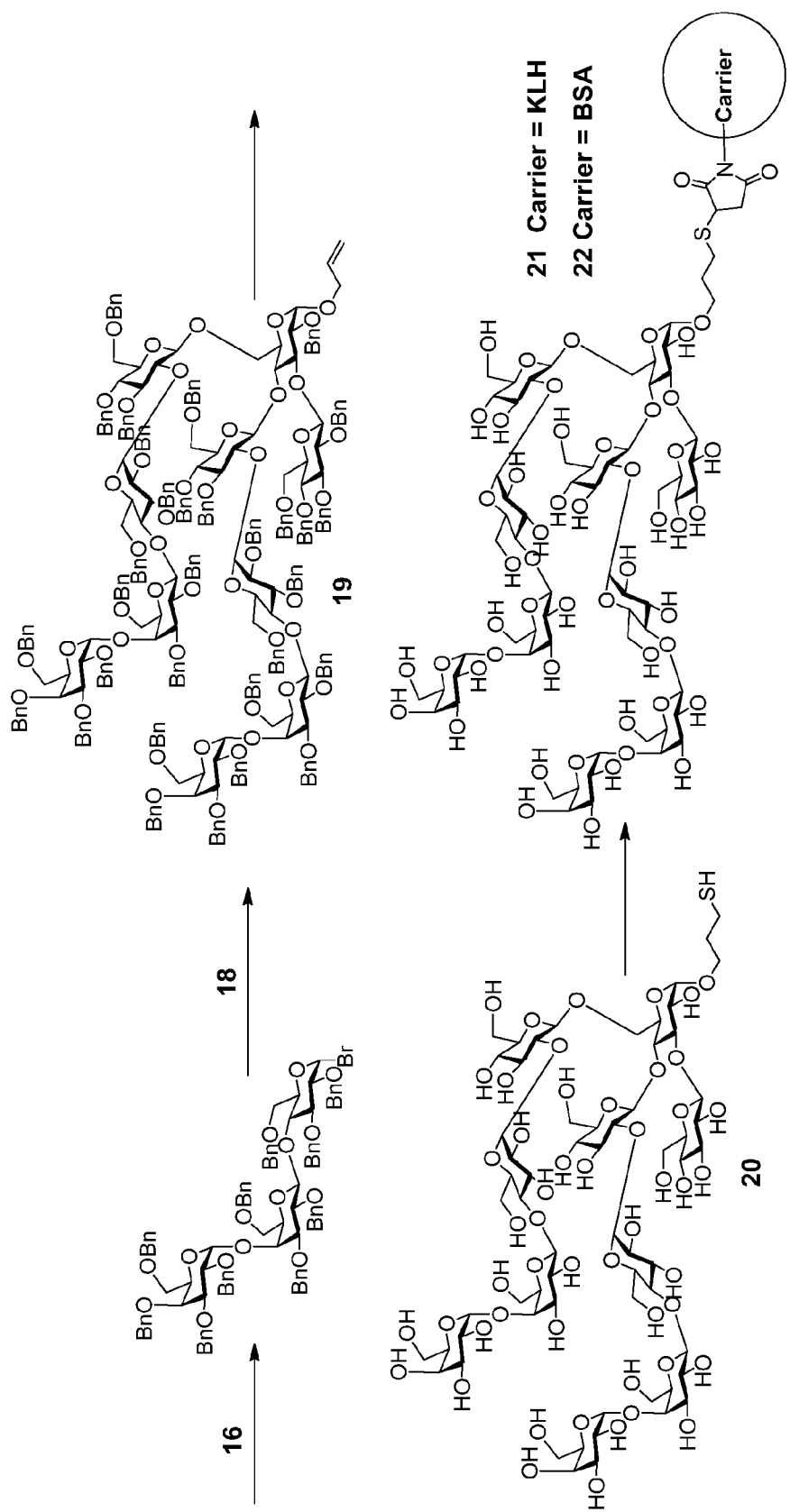

Synthesis of Serotype B11 Decamer 20 (FIGS. 10A, 10B)

With reference to FIG. 10A, allyl 3-O-(3,4,6-tri-O-benzyl-β-D-glucopyranosyl)-4,6-O-benzylidene-α-D-glucopyranoside 57 (33.5 g, 45.2 mmol) was co-evaporated with toluene (2×25 mL) before being taken up in a 4:1 solution of NMP: THF (400 mL) and cooled to 0° C. Solid NaH (4.52 g of 60% suspension, 113 mmol) was added and the mixture was stirred for 10 minutes before the slow addition of benzyl bromide (12.9 mL, 146 mmol) over 20 minutes. The reaction mixture was stirred at room temperature for 18 hours, quenched with methanol, stirred for 1 hour and the solvent removed. The residue was suspended in ethyl acetate (1 L), washed with 1 N HCl, brine, and saturated $NaHCO_3$ (250 mL each). The ethyl acetate solution was dried over $MgSO_4$, filtered and concentrated in vacuo. The crude material was used without further purification.

The crude benzylation product was taken up in $CH_2Cl_2$ (200 mL) and a solution of trifluoroacetic acid in water (3:2, 10 mL) was added. The reaction mixture was stirred for 16 hours then quenched with solid $NaHCO_3$ and stirred until bubbling ceased. The layers were separated and the aqueous phase was extracted with $CH_2Cl_2$ (200 mL). The combined organic extracts were dried over $MgSO_4$, filtered and concentrated in vacuo. The crude residue was passed through a silica plug, eluting with 9:1 heptane:ethyl acetate to remove benzaldehyde-related material, then with 1:1 ethyl acetate: $CH_2Cl_2$. The residue was crystallized from ethanol to give allyl 3-O-(2,3,4,6-tetra-O-benzyl-β-D-glucopyranosyl)-2-O-benzyl-α-D-glucopyranoside 14 (22.2 g, 67%).

Allyl 3-O-(2,3,4,6-tetra-O-benzyl-β-D-glucopyranosyl)-2-O-benzyl-α-D-glucopyranoside 14 (10.1 g, 12.1 mmol), 4-methoxyphenol (3.76 g, 30.3 mmol), and triphenylphosphine (4,77 g, 18.2 mmol) were combined in a flask, cooled to 0° C. before adding anhydrous $CH_2Cl_2$ (100 mL). This solution was stirred for 40 minutes and then a solution of diethylazodicarboxylate (DEAD) in toluene (40% by weight, 8.84 mL, 19.4 mmol) was added. The reaction mixture was stirred at 0° C. for 45 minutes, and then allowed to warm to room temperature overnight. The reaction mixture was diluted with $CH_2Cl_2$, washed with 1N NaOH (200 mL, 100 mL), 1 N HCl (200 mL), saturated $NaHCO_3$ (200 mL), and brine, dried over $Na_2SO_4$, filtered and concentrated. The residue was purified on a silica gel column eluted using an ethyl acetate:heptane step gradient (1:10→1:5→1:3) to give allyl 3-O-(2,3,4,6-tetra-O-benzyl-β-D-glucopyranosyl)-2-O-benzyl-6-O-(4-methoxyphenyl)-α-D-glucopyranoside 14 (7.81 g, 69%).

Allyl 3-O-(2,3,4,6-tetra-O-benzyl-β-D-glucopyranosyl)-2-O-benzyl-6-O-(4-methoxyphenyl)-α-D-glucopyranoside 14 (2.62 g, 2.79 mmol) and 2-pivaloyl,3,4,6-tri-O-benzyl-β-D-glucopyranosyl trichloroacetimidate 2 (2.85 g, 4.20 mmol) were combined, co-evaporated with toluene (3×10 mL) and dissolved in dry $CH_2Cl_2$ (25 mL). Freshly activated AW-300 molecular sieves (3 g) were added and the reaction mixture was stirred for 10 minutes and cooled to 0° C. A solution of trimethylsilyl trifluoromethanesulfonate (TMSOTf, 0.05 mL, 0.28 mmol) in $CH_2Cl_2$ (0.45 mL) was added and the reaction stirred for 30 minutes, at which point another aliquot of 2 (0.95 g, 1.4 mmol) was added. After another 30 minutes the reaction mixture was quenched with $Et_3N$ (1 mL), filtered and the solvent removed to give the crude coupling product, which was purified by silica gel chromatography (500 mL column), eluting with 3:1 heptane:ethyl acetate to give the desired trisaccharide (3.5 g, 86%).

The trisaccharide coupling product (1.75 g, 1.20 mmol) was dissolved in methanol:tetrahydrofuran (2:1, 15 mL) and sodium methoxide solution (1.0 mL, 25% by weight, 4.4 mmol) was added. The solution was stirred at room temperature for 42 hours, quenched with 1N HCl, diluted with ethyl acetate (200 mL), washed with brine (100 mL), and saturated NaHCO$_3$ (100 mL), dried over Na$_2$SO$_4$, filtered and concentrated. The crude material was purified on a silica gel column (40 g) using an ISCO automated chromatography system, eluting with a 0→70% gradient of ethyl acetate in heptane, to give the desired trisaccharide 15 (0.870 g, 50%).

Thiomethyl 4-O-(2,3,6-tri-O-benzyl-4-O-(2,3,4,6-tetra-O-benzyl-α-D-glucopyranosyl)-β-D-galactopyranosyl)-2,3,6-tri-O-benzyl-β-D-glucopyranoside 16(2.50 g, 1.75 mmol) (*J. Org. Chem.* 61 (1996) 7711) was co-evaporated with toluene (2×10 mL) then dissolved in dry CH$_2$Cl$_2$ (20 mL) under nitrogen and cooled to 0° C. Bromine (115 µL, 4.5 mmol) was added and the reaction mixture stirred for 20 minutes. The reaction was quenched with saturated Na$_2$S$_2$O$_3$ solution (50 mL), and the aqueous layer was extracted with CH$_2$Cl$_2$ (3×50 mL). The combined organic extracts were dried over Na$_2$SO$_4$, filtered and concentrated to give the crude glycosyl bromide, which was used without further purification.

The glycosyl bromide and the trisaccharide acceptor 15 (825 mg, 0.60 mmol) were combined and co-evaporated with toluene (2×10 mL), taken up in anhydrous diethyl ether (10 mL) under nitrogen and cooled to −40° C. Silver triflate (450 mg, 1.75 mmol) was added and the reaction mixture was stirred for 1 hour. The reaction was quenched by pouring into saturated sodium ascorbate solution (25 mL) and stirring for 30 minutes. The mixture was filtered through celite and the filtrate washed with ethyl acetate (3×50 mL). The organic layer was washed with brine, dried over Na$_2$SO$_4$, filtered and concentrated. The crude residue was passed through a silica plug, eluting with heptane:ethyl acetate, the solvent was removed and the crude hexasaccharide was used without further purification.

The crude hexasaccharide (~0.6 mmol) was taken up in acetonitrile and water (4:1, 20 mL) and cooled to 0° C. Ammonium cerium(IV) nitrate (CAN, 1.15 g, 2.1 mmol) was added and the reaction mixture was stirred for 2 hours. Ethyl acetate (50 mL) was added and the mixture was washed with brine and saturated NaHCO$_3$, (2×50 mL), dried over Na$_2$SO$_4$, filtered and concentrated. The crude residue was purified by silica gel chromatography eluting with 15% ethyl acetate in toluene to give the desired hexasaccharide 17 (280 mg, 18%).

Hexasaccharide acceptor 17 (333 mg, 0.126 mmol) and 2-pivaloyl-3,4,6-tri-O-benzyl-β-D-glucopyranosyl trichloroacetimidate 2 (171 mg, 0.251 mmol) were combined and dissolved in dry CH$_2$Cl$_2$ (5 mL). Freshly activated AW-300 molecular sieves (300 mg) were added and the reaction mixture was stirred for 20 minutes and cooled to 0° C. Trimethylsilyl trifluoromethanesulfonate (TMSOTf, 5 µL, 0.0125 mmol) was added and the reaction stirred for 30 minutes, at which point another aliquot of 2 (0.95 g, 1.4 mmol) was added. After another 30 minutes the reaction mixture was quenched with Et$_3$N (1 mL), diluted with CH$_2$Cl$_2$ (5 mL), filtered and concentrated. The crude coupling product was purified by silica gel chromatography, eluting with a heptane: ethyl acetate step gradient (5:1→4:1→3:1) to give the desired intermediate heptasaccharide (298 mg, 75%).

The heptasaccharide (620 mg, 0.200 mmol) was dissolved in methanol: tetrahydrofuran (1:1, 20 mL) and sodium methoxide solution (2.0 mL, 25% by weight, 8.8 mmol) was added. The solution was stirred at 45° C. for 43 hours, cooled to room temperature and concentrated to ~5 mL. The residue was dissolved in ethyl acetate (50 mL), washed with 1N HCl (50 mL), saturated NaHCO$_3$ (50 mL) and brine (50 mL), dried over Na$_2$SO$_4$, filtered and concentrated. The crude material was purified by silica gel chromatography, eluting with a heptane:ethyl acetate step gradient to give the desired heptasaccharide 18 (570 mg, 94%).

Turning to FIG. 10B, thiomethyl 4-O-(2,3,6-tri-O-benzyl-4-O-(2,3,4,6-tetra-O-benzyl-α-D-glucopyranosyl)-β-D-galactopyranosyl)-2,3,6-tri-O-benzyl-β-D-glucopyranoside 16 (745 mg, 0.519 mmol) (*J. Org. Chem.* 61 (1996) 7711) was dissolved in dry CH$_2$Cl$_2$ (8.5 mL) under nitrogen and cooled to 0° C. Bromine (66 µL, 1.28 mmol) was added and the reaction mixture stirred for 20 minutes. The reaction was quenched with saturated Na$_2$S$_2$O$_3$ solution (25 mL), and stirred until the color faded, then was diluted with CH$_2$Cl$_2$ (50 mL). The organic layer was washed with saturated NaHCO$_3$ (50 mL) and brine (50 mL), dried over Na$_2$SO$_4$, filtered and concentrated to give the crude glycosyl bromide, which was used without further purification.

The glycosyl bromide and the heptasaccharide acceptor 18 (525 mg, 0.170 mmol) were combined and dried under vacuum, 4 Å molecular sieves (700 mg) were added and anhydrous diethyl ether (10 mL) was added under nitrogen. The mixture was cooled to −40° C. before silver triflate (140 mg, 0.545 mmol) was added and the reaction mixture was stirred for 1 hour. The reaction was warmed to −20° C. over 30 minutes then quenched by pouring into saturated sodium ascorbate solution (25 mL) and stirring for 30 minutes. The mixture was filtered through celite and the filtrate washed with saturated NaHCO$_3$ (50 mL) and brine (50 mL), dried over Na$_2$SO$_4$, filtered and concentrated. The crude residue was purified by silica gel chromatography, eluting with a toluene:ethyl acetate step gradient (20:1→18:1→15:1) to give enriched decasaccharide. The partially purified decasaccharide was purified to homogeneity by size exclusion chromatography using BioRad SX-1 BioBeads eluting with toluene (two 2.5×50 cm columns) followed by another silica gel column eluting with heptane:ethyl acetate 2:1 to give the desired decasaccharide 19 (567 mg, 74%).

Decasaccharide 19 (400 mg, 0.089 mmol) was dissolved in dioxane (6 mL), thioacetic acid (0.5 mL, 7.1 mmol) was added, and the solution purged with argon gas for 10 minutes. The solution was purged with nitrogen gas for 15 minutes before AIBN (50 mg, 0.30 mmol) was added and the reaction mixture heated to 75° C. under an inert atmosphere for 18 hours. The solvent was removed and the crude product was co-evaporated with toluene (2×10 mL). The crude residue was purified by size exclusion chromatography using BioRad SX-1 Bio-Beads (2.5 cm×25 cm column) and toluene as the eluent. Appropriate fractions were combined to give the desired octasaccharide thioacetate product (370 mg, 91%).

Decasaccharide thioacetate (370 mg, 0.081 mmol) was co-evaporated with toluene (2×10 mL) and dissolved in dry THF (5 mL). In a flame-dried jacketed flask equipped with a dry ice condenser and cooled to −78° C., NH$_3$ gas was condensed into the flask under an Ar atmosphere until the liquid volume reached approximately 10 mL. The decasaccharide thioacetate solution was transferred by cannula into the liquid NH$_3$. Sodium metal (200 mg, 8.7 mmol) was added under positive Ar gas flow and once a permanent blue color was established the reaction was stirred for another 20 minutes. The reaction was quenched at −78° C. by the addition of saturated NH$_4$Cl solution (10 mL) and warmed to room temperature. N$_2$ was bubbled through the reaction mixture to remove excess NH$_3$, and then the solution was concentrated to dryness. The crude material was purified by size exclusion chromatography on a bed of BioGel P4 (2.5 cm×60 cm column) by elution with water. The fractions containing product were concentrated to yield the desired *Moraxella* serotype B11 decasaccharide 20 (92 mg, 30%).

Synthesis of Serotype B11 Decamer Conjugates 21, 22 (FIG. 10B)

To synthesize the KLH conjugate 21, a solution of tris(2-carboxyethyl)phosphine (TCEP) in water (8.6 µL, 0.05 M, 0.43 µmol) was added to a solution of decasaccharide thiol 20 in water (12.8 mg/mL, 110 µL, 0.86 µmol), and the resulting solution was stirred for 1 hour. A solution of maleimide-activated keyhole limpet hemocyanin (Imject® KLH, Pierce, Rockford, Ill.) (0.5 mL, 5 mg, ~0.43 µmol maleimide) was added and the resulting solution stirred overnight at room temperature. The reaction mixture was purified by de-salting on D-Salt P-6000 10 mL column (Pierce, Rockford, Ill.). The column was pre-equilibrated with 30 mL of purification buffer (Pierce, Prod. No. 77159), the crude material loaded onto the column and eluted with purification buffer. 1-mL fractions were collected and analyzed for protein content by absorbance at 280 nm ($A_{280}$). Fractions containing protein were combined and lyophilized to give the desired serotype B11 decamer-KLH conjugate 21.

To synthesize the BSA conjugate 22, a solution of tris(2-carboxyethyl)phosphine (TCEP) in water (30 µL, 0.05 M, 1.5 µmol) was added to a solution of decasaccharide thiol 20 in water (12.8 mg/mL, 390 µL, 3.0 µmol), and the resulting solution was stirred for 1 hour. A solution of maleimide-activated bovine serum albumin (Imject® BSA, Pierce, 5 mg, ~1.5 µmol maleimide) in Imject® Conjugation Buffer (Pierce, 250 µL diluted with water, 250 µL) was added and the resulting solution stirred overnight at room temperature. The reaction mixture was purified by de-salting on D-Salt P-6000 10 mL column (Pierce, Rockford, Ill.). The column was pre-equilibrated with 30 mL of purification buffer (Pierce, Prod. No. 77159), the crude material loaded onto the column and eluted with purification buffer. 1-mL fractions were collected and analyzed for protein content by absorbance at 280 nm ($A_{280}$). Fractions containing protein were combined and lyophilized to give the desired serotype B11 decamer-BSA conjugate 22.

Example 8

Synthesis of Serotype C11 Decamer and Conjugates thereof

Figure 11A:
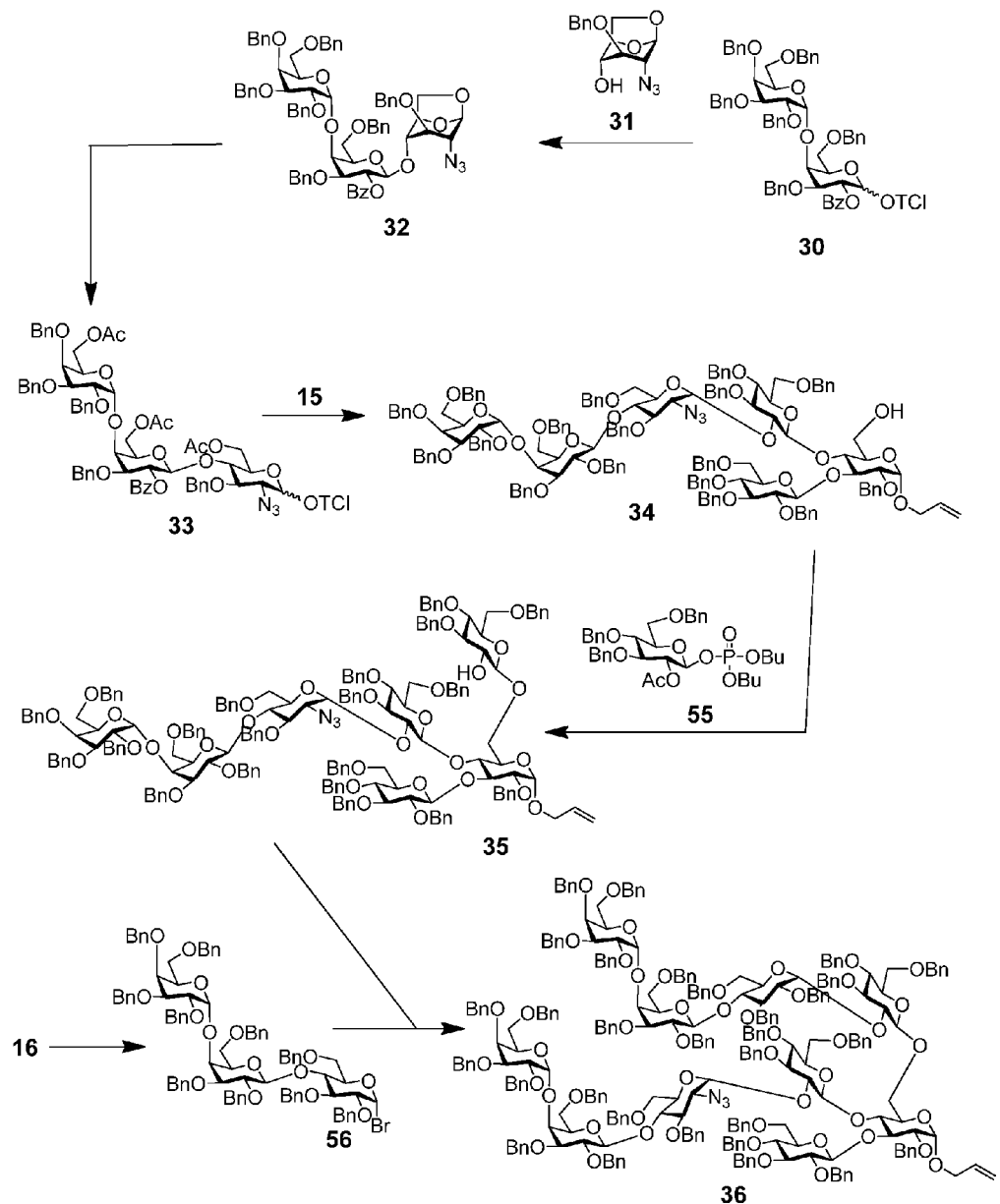
FIGS. 11A and 11B depict a reaction scheme for synthesizing a Serotype C11 decasaccharide 37 and conjugates 38, 39 thereof as described in Example 8.
Figure 11B:
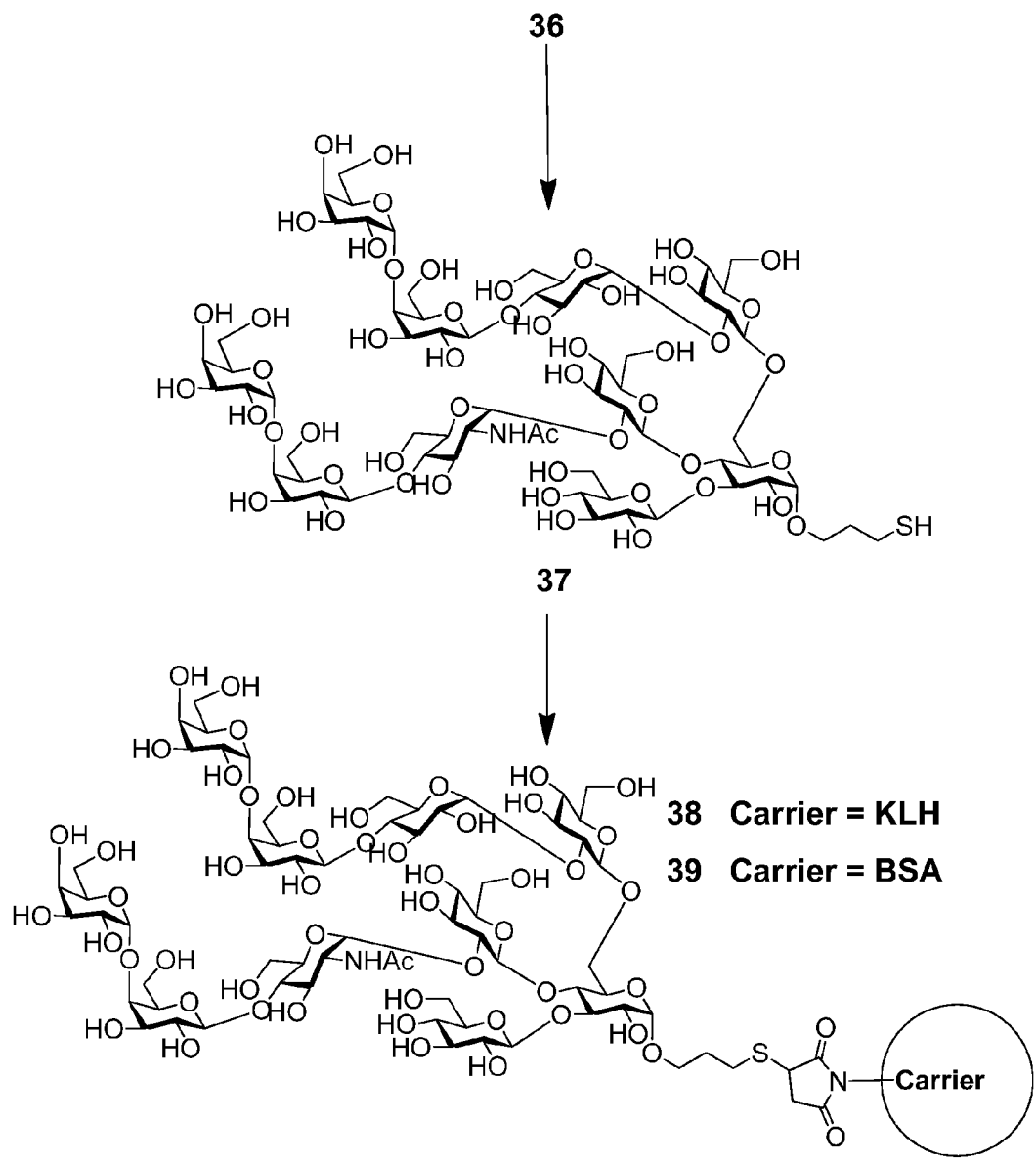

Synthesis of Serotype C11 decamer 37 (FIGS. 11A, 11B)

With reference to FIG. 11A, 1,6-anhydro-2-deoxy-2-azido-3-O-benzyl-β-D-glucopyranose 31 (765 mg, 2.75 mmol) and 2-benzoyl-4-(2,3,4,6-tetra-O-benzyl-α-D-galactopyranosyl)-3,6-di-O-benzyl-D-galactopyranosyl trichloroacetimidate 30 (2.3 mmol) were combined, co-evaporated with toluene (2×10 mL) and dissolved in dry $CH_2Cl_2$ (30 mL). Freshly activated AW-300 molecular sieves (2 g) were added and the reaction mixture was stirred for 10 minutes and cooled to 0° C. A solution of trimethylsilyl trifluoromethanesulfonate (TMSOTf, 0.042 mL, 0.23 mmol) in $CH_2Cl_2$ (0.38 mL) was added and the reaction stirred for 30 minutes. The reaction mixture was quenched with $Et_3N$ (0.5 mL), filtered and the solvent removed to give the crude coupling product, which was purified on a silica gel column (40 g) using an ISCO automated chromatography system, eluting with a 0→40% gradient of ethyl acetate in heptane, to give the desired trisaccharide 32 (1.9 g, 66%).

Acetic anhydride (15 mL) was added to trisaccharide 32 (1.8 g, 1.43 mmol), and $Sc(OTf)_3·H_2O$ (30 mg, 0.058 mmol) was added. After 5 hours a second aliquot of $Sc(OTf)_3·H_2O$ (30 mg, 0.058 mmol) was added and the reaction mixture was stirred overnight. The reaction mixture was cooled to 0° C. and methanol (10 mL) was added over 30 minutes, keeping the temperature below 10° C. The mixture was partitioned between ethyl acetate and water (100 mL each). The organic layer was washed with water (3×50 mL), saturated $NaHCO_3$ (50 mL) and brine (50 mL), dried over $Na_2SO_4$, filtered and concentrated. The crude material was purified on a silica gel column (80 g) using an ISCO automated chromatography system, eluting with a 0→70% gradient of ethyl acetate in heptane, to give a mixture of trisaccharides (1.8 g, >90%). The mixture was predominantly the desired 1,6-di-O-acetate containing product, but also included small amounts of similar compounds in which the other primary benzyl ethers had been exchanged for acetyl groups. The mixture was used without further purification.

The trisaccharide mixture (1.8 g, 1.3 mmol) was taken up in dry THF (20 mL) and purged with nitrogen for 10 minutes while cooling to 0° C. Ammonia gas was bubbled through the solution for 15 minutes and the reaction mixture was stirred for 2 hours, during which the temperature was allowed to return to room temperature. The solution was purged with nitrogen for 30 minutes and then concentrated in vacuo. The residue was purified on a silica plug, eluting with heptane:ethyl acetate (1:1) to give the lactol as a yellow oil (1.6 g, 92%).

The trisaccharide lactol mixture (1.6 g, 1.31 mmol) was dissolved in $CH_2Cl_2$ (25 mL) and trichloroacetonitrile (5 mL) was added. Solid $K_2CO_3$ (2 g) was added and the heterogeneous mixture was stirred at room temperature for 2 hours before filtering through celite. The filtrate was concentrated, redissolved in heptane:ethyl acetate (1:1) and filtered through a 30-mL silica plug that had been pre-washed with heptane:ethyl acetate:$Et_3N$ (1:1:0.01→1:1:0). The solvent was removed to the desired trisaccharide trichloroacetimidate 33 (1.5 g, 84%).

The trisaccharide trichloroacetimidate donor 33 (1.5 g, 1.1 mmol) and the trisaccharide acceptor 15 were combined, co-evaporated with toluene (3×10 mL) and dissolved in dry ether (20 mL). Freshly activated 4 Å AW-300 molecular sieves (2 g) were added and the reaction mixture was stirred for 1 hour and cooled to 0° C. A solution of trimethylsilyl trifluoromethanesulfonate (TMSOTf) in ether (0.1 M, 1.1 mL) was added over 5 minutes and the reaction stirred for 1 hour at 0° C., at which point another 0.1 equivalents of TMSOTf was added. After another 1 hour the reaction mixture was quenched with $Et_3N$ (0.2 mL), filtered through celite and the solvent removed to give the crude coupling product, which was purified on a silica gel column (40 g) using an ISCO automated chromatography system, eluting with a 0→70% gradient of ethyl acetate in heptane, to give a mixture of hexasaccharides, which included α- and β-anomers (2.2 g, 78%).

The hexasaccharide mixture (2.2 g, 0.85 mmol) was dissolved in methanol:tetrahydrofuran (1:1, 20 mL) and sodium methoxide solution (1.0 mL, 25% by weight, 4.4 mmol) was added. The solution was stirred at room temperature for 18 hours, at which point another aliquot of sodium methoxide solution (1.0 mL, 25% by weight, 4.4 mmol) was added. The solution was stirred at room temperature for an additional 2 hours, quenched with A-15($H^+$) resin and filtered through celite. Concentration of the filtrate gave the crude hexasaccharide polyol, which was used without further purification.

The crude hexasaccharide polyol (~0.85 mmol) was taken up in a 4:1 solution of NMP:THF (24 mL) and cooled to 0° C. Benzyl bromide (0.71 mL, 5.95 mmol) was added followed by solid NaH (0.27 g of 60% suspension, 6.8 mmol). The mixture was stirred for 4 hours, over which the mixture warmed to room temperature, and additional aliquots of NaH (0.27 g) and BnBr (0.71 mL) were added. After stirring for an additional 18 hours the reaction was quenched with methanol (5 mL) and the solvent removed. The residue was suspended in ethyl acetate (100 mL), washed with water and brine, dried over $Na_2SO_4$, filtered and concentrated in vacuo. The crude material was purified on a silica gel column (120 g) using an ISCO automated chromatography system, eluting with a 0→50% gradient of ethyl acetate in heptane, to give a mixture of hexasaccharides, which included α- and β-anomers. A second silica gel purification (80 g column) using an ISCO automated chromatography system, eluting with a 0→40% gradient of ethyl acetate in heptane, gave the desired hexasaccharide as pure a-anomer (1.2 g).

The crude hexasaccharide (1.14 g, ~0.42 mmol) was taken up in acetonitrile and water (4:1, 15 mL) and cooled to 0° C. Ammonium cerium(IV) nitrate (CAN, 700 mg, 1.27 mmol) was added and the reaction mixture was stirred for 2 hours. The reaction was quenched with $Et_3N$ (3 mL) and filtered through celite, washing with $CH_2Cl_2$ (75 mL). The solution was dried over $Na_2SO_4$, filtered and concentrated. The crude residue was purified by silica gel chromatography eluting with a heptane:ethyl acetate step gradient (4:1→3:1→2:1→1:1) to give the desired hexasaccharide 34 (752 mg, 69%) and recovered starting material (210 mg, 18%).

Hexasaccharide acceptor 34 (750 mg, 0.290 mmol) and di-n-butylphosphoryl 2-O-acetyl-3,4,6-tri-O-benzyl-β-D-glucopyranoside 55 (238 mg, 0.348 mmol) were combined, co-evaporated with toluene (3×5 mL), dissolved in dry $CH_2Cl_2$ (6 mL) and cooled under nitrogen to −30° C. The reaction mixture was stirred for 10 minutes before trimethylsilyl trifluoromethanesulfonate (TMSOTf, 63 μL, 0.348 mmol) was added. The reaction mixture was stirred for 20 minutes then quenched with $Et_3N$ (4 mL), and the solvent removed to give the crude coupling product, which was purified by silica gel chromatography (250 mL column), eluting using a heptane: ethyl acetate step gradient (6:1→4:1→3:1→2:1) to give the desired heptasaccharide coupling product (750 mg, 84%).

Heptasaccharide 35 (750 mg, 0.245 mmol) was dissolved in methanol: tetrahydrofuran (2:1, 15 mL) and sodium methoxide solution (2.0 mL, 25% by weight, 8.8 mmol) was added. The solution was stirred at room temperature for 4 hours and concentrated in vacuo. The residue was partitioned between ethyl acetate (150 mL) and saturated $NH_4Cl$ (100 mL), washed with brine (2×100 mL), dried over $Na_2SO_4$, filtered and concentrated. The crude material was purified by silica gel chromatography (250 mL column), eluting using a heptane:ethyl acetate step gradient (4:1→2:1) to give the desired heptasaccharide 35 (719 mg, 97%).

Thiomethyl 4-O-(2,3,6-tri-O-benzyl-4-O-(2,3,4,6-tetra-O-benzyl-α-D -glucopyranosyl)-β-D-galactopyranosyl)-2,3, 6-tri-O-benzyl-β-D-glucopyranoside 16 (779 mg, 0.541 mmol) (*J. Org. Chem.* 61 (1996) 7711) was co-evaporated with toluene (3×8 mL) then dissolved in dry $CH_2Cl_2$ (5 mL) under nitrogen and cooled to 0° C. Bromine (29 μL, 0.568 mmol) was added and the reaction mixture stirred for 10 minutes. Toluene (10 mL) was added, the mixture concentrated to dryness and the toluene azeotrope step was repeated twice more to give the crude glycosyl bromide, which was used without further purification.

The heptacchharide acceptor 35 (543 mg, 0.180 mmol) was co-evaporated with toluene (3×8 mL). Freshly activated 4 Å molecular sieves (1 g) were added under nitrogen. The glycosyl bromide was taken up in anhydrous diethyl ether (10 mL) under nitrogen, transferred to the acceptor/molecular sieves mixture and cooled to −40° C. Silver triflate (139 mg, 0.541 mmol) was added and the reaction mixture was stirred for 1 hour. The reaction was quenched at −20° C. with $Et_3N$ (0.4 mL), diluted with $CH_2Cl_2$ (50 mL) and filtered through celite. The filtrate was stirred with saturated sodium ascorbate solution (50 mL) for 20 minutes, filtered through celite and the organic layer of the filtrate was washed with saturated NaHCO3 (100 mL) and brine (100 mL), dried over $Na_2SO_4$, filtered and concentrated. The crude residue was purified by silica gel chromatography (250 mL column), eluting with a toluene:ethyl acetate solvent system, and then by size exclusion chromatography on BioRad SX-1 BioBeads, eluting with toluene to give the desired decasaccharide 36 (430 mg, 54%).

Turning now to FIG. 11B, the decasaccharide 36 (400 mg, 0.091 mmol) was dissolved in dioxane (3 mL), AIBN (40 mg, 0.24 mmol) was added and the solution purged with nitrogen gas. Thioacetic acid (0.3 mL, 4.3 mmol) was added, and the solution purged with nitrogen gas for 15 minutes and the reaction mixture heated to 80° C. under an inert atmosphere for 18 hours. The solution was cooled to room temperature, quenched with cyclohexene (0.2 mL) and concentrated in vacuo. The crude residue was purified by size exclusion chromatography using BioRad SX-1 Bio-Beads (2.5 cm×60 cm column) and toluene as the eluent. Appropriate fractions were combined to give the desired decasaccharide thioacetate product (260 mg, 64%) mixed with recovered starting material (20%). The mixture was re-subjected to the reaction conditions and purification scheme to convert the remaining starting material to the desired decasaccharide thioacetate (300 mg, 74% total yield).

The decasaccharide thioacetate (162 mg, 0.036 mmol) was dissolved in DMF (3 mL) and ethanol (1.5 mL), and the solution was purged with nitrogen for 5 minutes. Benzyl chloride (60 μL, 0.52 mmol) and 1.0 M NaOH (0.2 mL) were added, and the reaction mixture was stirred for 1 hour. The mixture was diluted with ethyl acetate (50 mL), washed with water (2×50 mL) and brine (2×50 mL), dried over $Na_2SO_4$, filtered and concentrated to a yellow oil (150 mg), which was used without further purification.

Decasaccharide benzyl thioether (150 mg, 0.033 mmol) was dissolved in dry THF (2 mL). In a flame-dried jacketed flask equipped with a dry ice condenser and cooled to −78° C., $NH_3$ gas was condensed into the flask under an Ar atmosphere until the liquid volume reached approximately 15 mL. The decasaccharide benzyl thioether solution was transferred into the liquid $NH_3$. Sodium metal (20 mg, 0.87 mmol) was added under positive Ar gas flow and stirred for 10 minutes. The reaction was quenched at −78° C. by the addition of saturated $NH_4Cl$ solution (0.1 mL) and warmed to room temperature. $N_2$ was bubbled through the reaction mixture to remove excess $NH_3$, and then the solution was concentrated to dryness. The crude material was purified by size exclusion chromatography on a bed of Sephadex G-10 (2.5 cm×8 cm column) by elution with water. The fractions containing product were concentrated to yield the crude decasaccharide with co-eluting salts (120 mg).

The crude decasaccharide/salt mixture (120 mg) was dissolved in water (0.8 mL) and methanol (0.4 mL), solid $NaHCO_3$ (40 mg), and acetic anhydride (40 μL) were added. The reaction mixture was stirred for 2 hours then loaded directly onto a Sephadex G-10 column (2.5 cm×8 cm) and eluted with water. Lyophilization of the appropriate fractions gave the desired Moraxella serotype C11 decasaccharide 37 (25 mg).

Synthesis of Serotype C11 Decamer Conjugates 38, 39 (FIG. 11B)

First, a conjugation stock solution of decasaccharide 37 was prepared by dissolving the decasaccharide 37 (6.7 mg, 3.82 µmol) in water (0.5 mL). Hydrazine in water (520 µL, 0.05 M, 60 µL) was added to the reaction mixture, was stirred at room temperature for 1 hour and concentrated in vacuo. The residue was co-evaporated with water (3×1 mL) and redissolved in water (300 µL). A solution of tris(2-carboxyethyl) phosphine (TCEP) in water (39 µL, 0.05 M, 1.95 µmol) was added and stirred for 1 hour. Imject® Conjugation Buffer (Pierce, 300 µL) was added to provide a stock solution for conjugation to KLH and BSA. To synthesize the KLH conjugate 38, the conjugation stock solution of decasaccharide thiol 37 (139 µL, 0.86 µmol) was added to a solution of maleimide-activated keyhole limpet hemocyanin (Imject® KLH, Pierce, Rockford, Ill.) (5 mg, ~0.43 µmol maleimide) in water (0.5 mL) was added and the resulting solution stirred overnight at room temperature. The reaction mixture was purified by de-salting on D-Salt P-6000 10 mL column (Pierce, Rockford, Ill.). The column was pre-equilibrated with 30 mL of purification buffer (Pierce, Prod. No. 77159), the crude material loaded onto the column and eluted with purification buffer. 1-mL fractions were collected and analyzed for protein content by absorbance at 280 nm ($A_{280}$). Fractions containing protein were combined and lyophilized to give the desired serotype C11 decamer-KLH conjugate 38.

To synthesize the BSA conjugate 39, the conjugation stock solution of decasaccharide thiol 37 (500 µL, 3.0 µmol) was added to a solution of maleimide-activated bovine serum albumin (Imject® BSA, Pierce, Rockford, Ill.) (5 mg, ~1.5 µmol maleimide) in Imject® Conjugation Buffer (Pierce, 300 µL diluted with water, 300 µL) and the resulting solution stirred for 18 hours at room temperature. The reaction mixture was purified by de-salting on D-Salt P-6000 10 mL column (Pierce, Rockford, Ill.). The column was pre-equilibrated with 30 mL of purification buffer (Pierce, Prod. No. 77159), the crude material loaded onto the column and eluted with purification buffer. 1-mL fractions were collected and analyzed for protein content by absorbance at 280 nm ($A_{280}$). Fractions containing protein were combined and lyophilized to give the desired serotype C11 decamer-BSA conjugate 39.

Example 9

Synthesis of Serotype C11 Heptamer and Conjugates thereof

Figure 12:
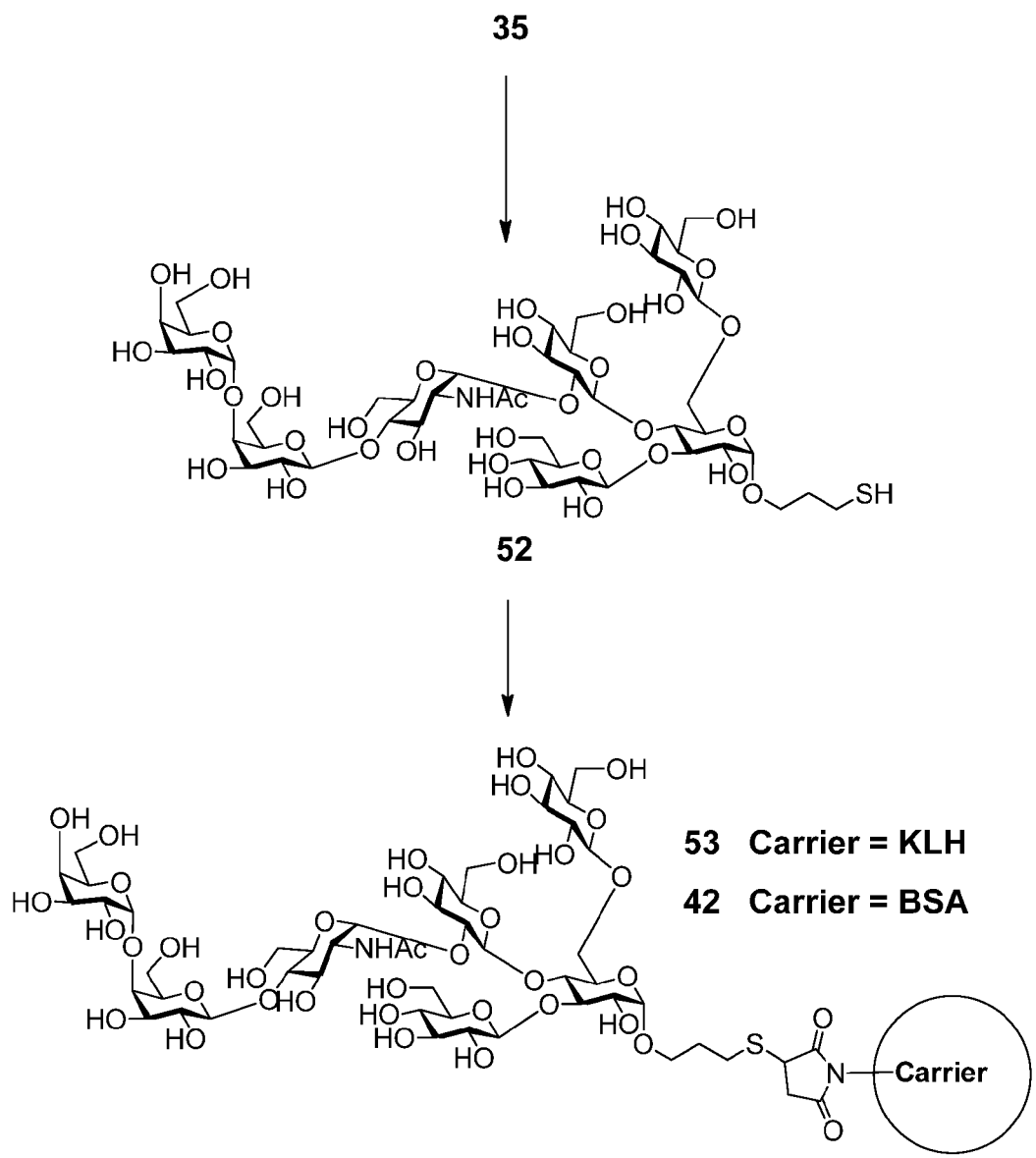
FIG. 12 depicts a reaction scheme for synthesizing a Serotype C11 heptamer substructure 52 and conjugates 42, 53 thereof as described in Example 9.
Figure 13A:
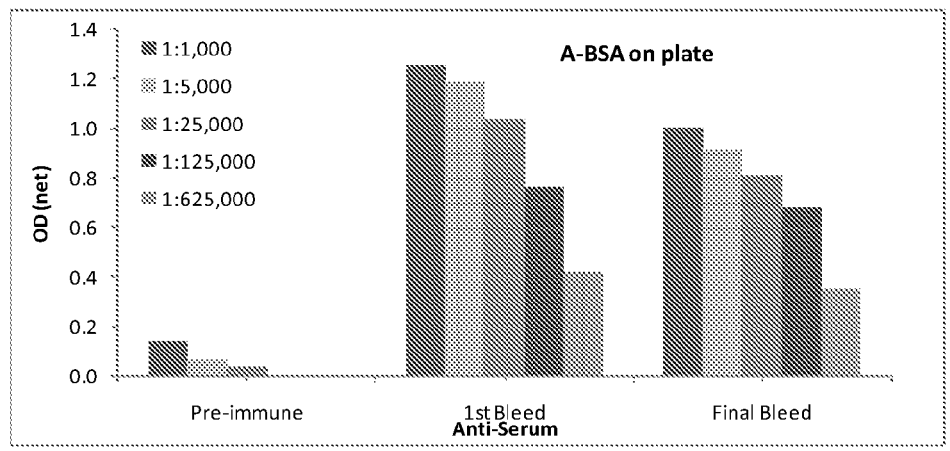
FIGS. 13A-13H depict ELISA results from Example 10, showing IgG antibody titers as a function of antibody-antigen complex absorption ($OD_{450}$) at 3 serum dilutions of immune sera obtained from 3 succesive bleeds (pre-immune 1$^{st}$ bleed, and final bleed) in rabbits (n=2) immunized with antigen-KLH conjugates corresponding to (A) Serotype A-KLH 28; (B) Serotype B7 hexasaccharide core-KLH 9; (C) Serotype B9-KLH 12; (D) Serotype B11-KLH 21; (E) Serotype C11 decamer-KLH 38; (F) Serotype C11-heptamer-KLH 53; (G) heptamer core-KLH 47; and (H) tetramer core-KLH 49. In each case, the antisera were incubated on ELISA plates adsorbed with their corresponding BSA conjugate, specifically: (A) Serotype A-BSA 29; (B) Serotype B7-BSA 41; (C) Serotype B9-BSA 40; (D) Serotype B11-BSA 22; (E) Serotype C11-decamer-BSA 39; (F) Serotype C11-heptamer-BSA 42; (G) heptamer core-BSA 48; and (H) tetramer core-BSA 50.
Figure 13B:
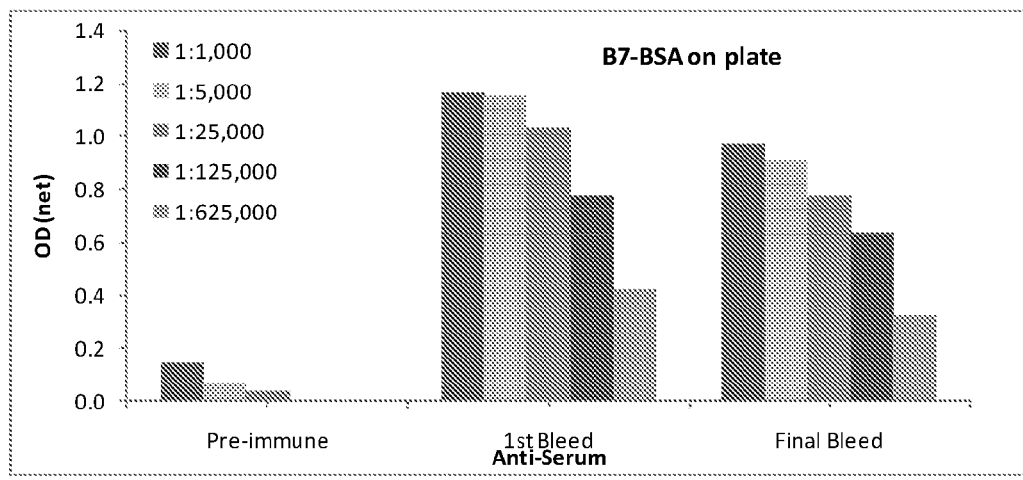
Figure 13C:
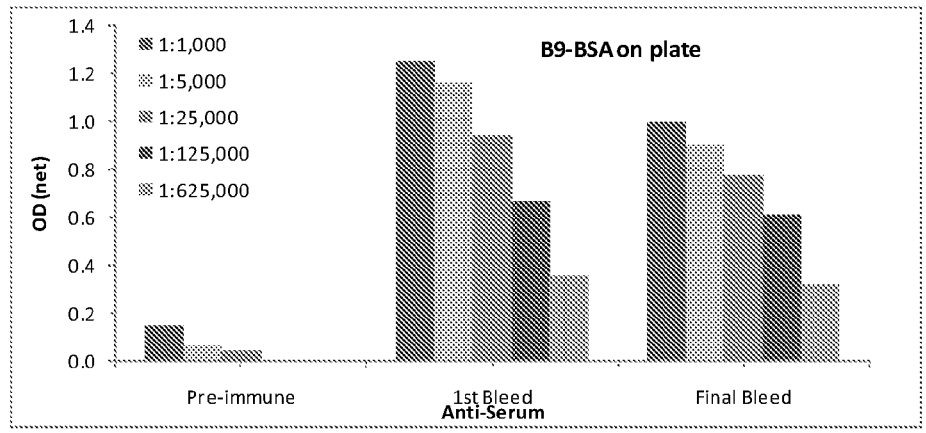
Figure 13D:
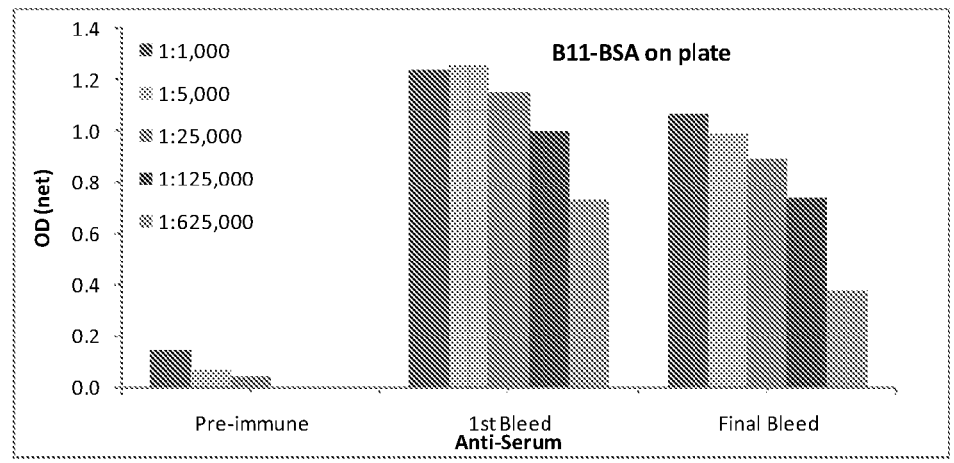
Figure 13E:
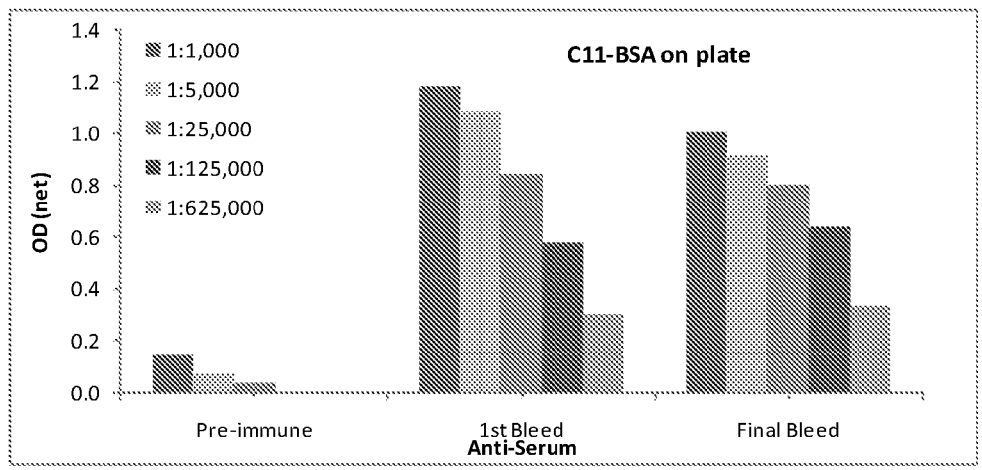
Figure 13F:
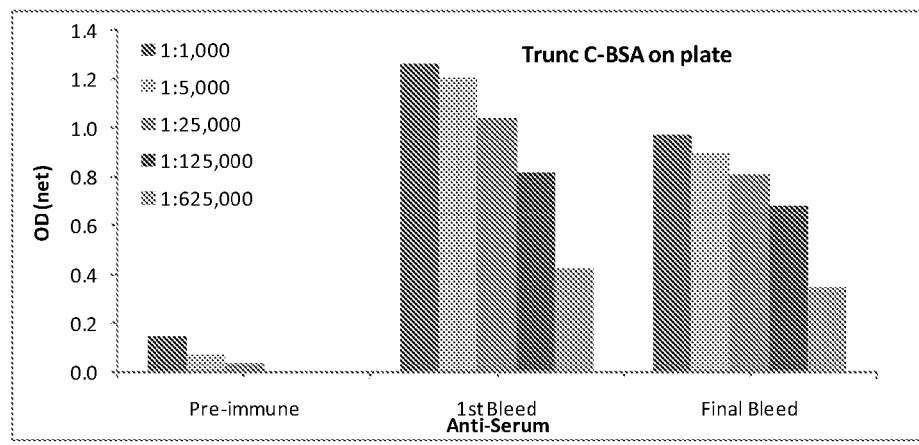
Figure 13G:
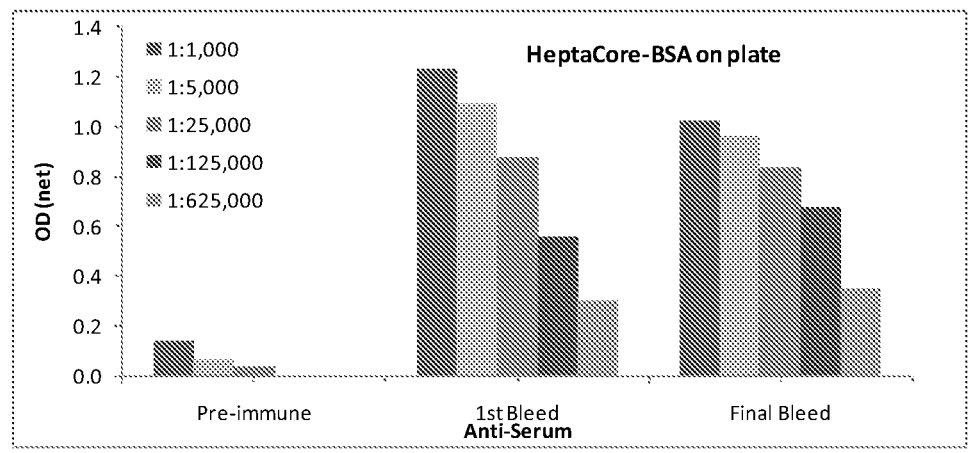
Figure 13H:
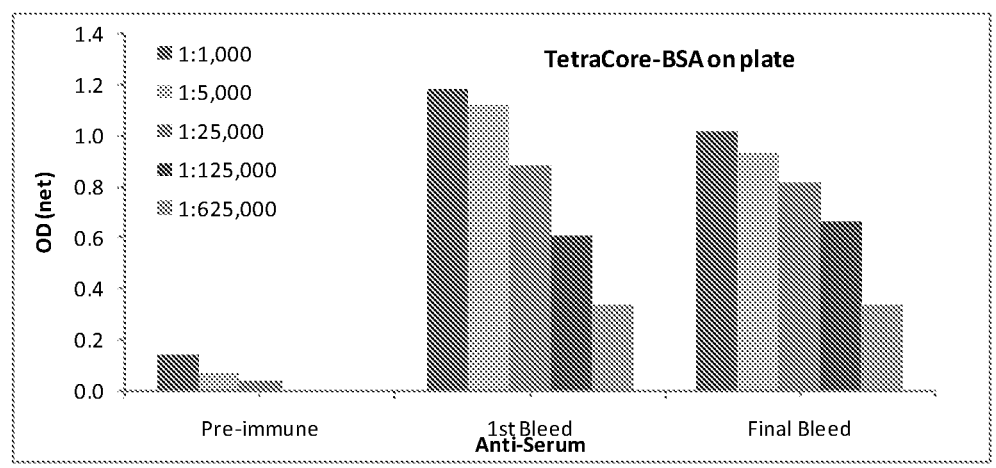
Figure 14A:
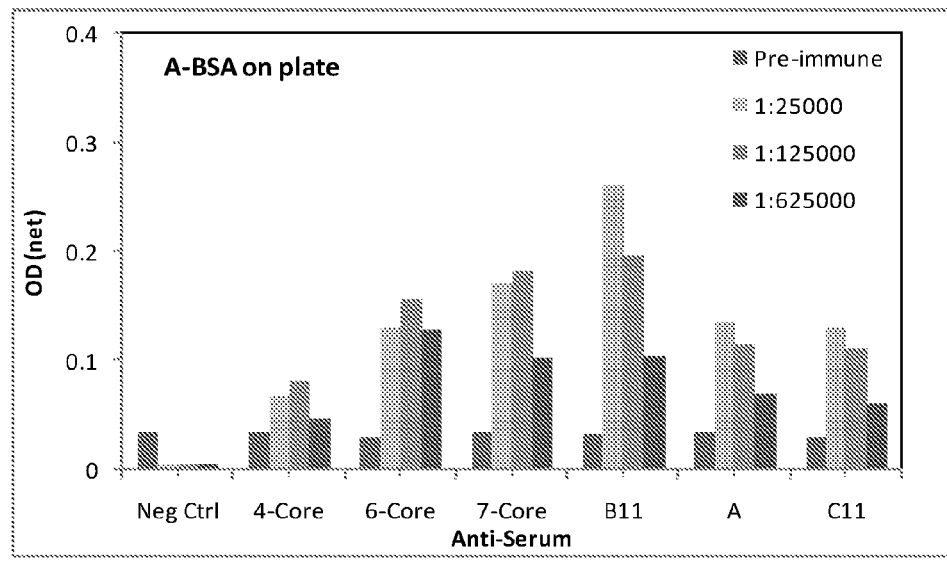
FIGS. 14A-14D depict specificity and cross-reactivity of antisera to different synthetic *Moraxella* LOS oligosaccharides by ELISA as described in Example1 1. Antisera from rabbits immunized with the indicated antigen-KLH conjugates corresponding to (left to right) KLH alone, tetramer core-KLH 49, hexamer core (B7)-KLH 9, heptamer core-KLH 47, Serotype B11-KLH 21, Serotype A-KLH 28, and Serotype C11-decamer-KLH 38 were incubated with ELISA plates adsorbed with antigen-BSA conjugates, including (A) Serotype A-BSA 29; (B) Serotype B11-BSA 22; (C) Serotype C11-decamer-BSA 39; and (D) Serotype C11-heptamer-BSA 42. Results are shown as a function of antibody-antigen complex absorption ($OD_{450}$) at the indicated serum dilutions.
Figure 14B:
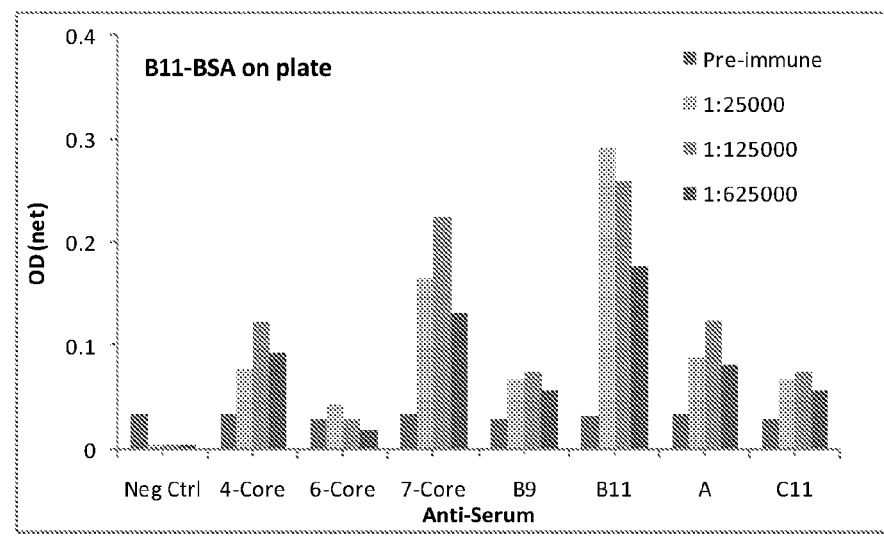
Figure 14C:
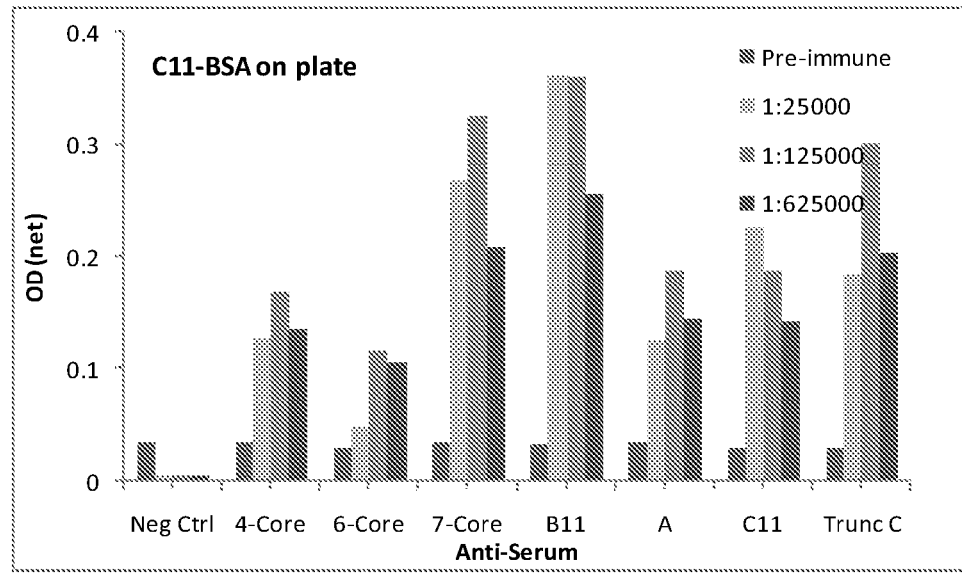
Figure 14D:
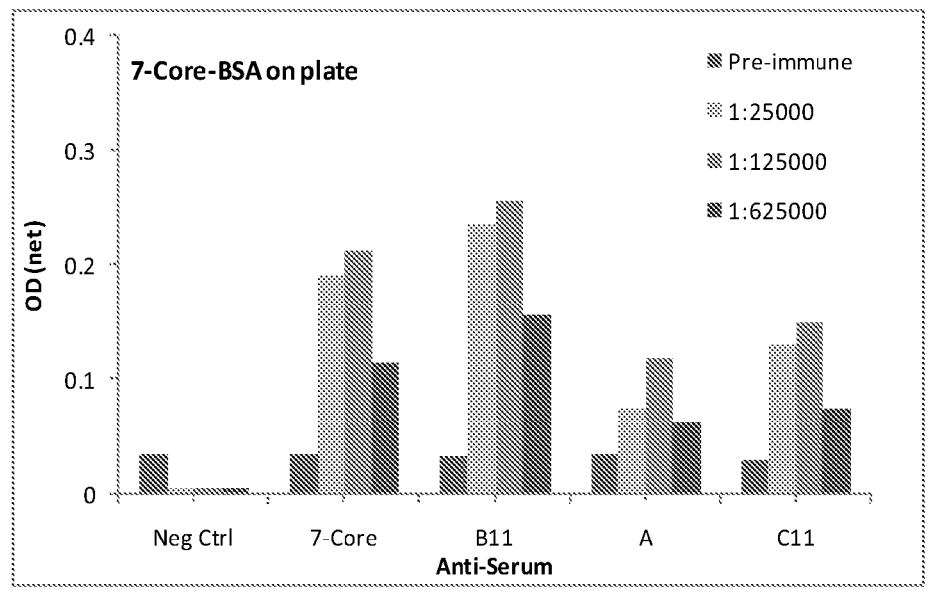

Synthesis of Serotype C11 Heptamer 52 (FIG. 12)

Heptasaccharide 35 (170 mg, 0.056 mmol; see Example 8) was dissolved in dioxane (10 mL). AIBN (40 mg, 0.24 mmol) and thioacetic acid (0.3 mL, 4.3 mmol) were added, and the solution purged with nitrogen gas for 15 minutes. The reaction mixture heated to 75° C. under an inert atmosphere for 18 hours, then cooled to room temperature, quenched with cyclohexene (0.1 mL) and concentrated in vacuo. The crude residue was purified by size exclusion chromatography using BioRad SX-1 Bio-Beads (2.5 cm×60 cm column) and toluene as the eluent. Appropriate fractions were combined to give the desired heptasaccharide thioacetate product (160 mg, 92%).

The heptasaccharide thioacetate (88 mg, 0.028 mmol) was dissolved in DMF (3 mL) and ethanol (1.5 mL), and the solution was purged with nitrogen for 5 minutes. Benzyl chloride (60 µL, 0.52 mmol) and 1.0 M NaOH (0.2 mL) were added, and the reaction mixture was stirred for 1 hour. The mixture was diluted with ethyl acetate (50 mL), washed with water (2×50 mL) and brine (2×50 mL), dried over $Na_2SO_4$, filtered and concentrated to a colorless oil (80 mg), which was used without further purification.

Heptasaccharide benzyl thioether (80 mg, 0.025 mmol) was dissolved in dry THF (2 mL). In a flame-dried jacketed flask equipped with a dry ice condenser and cooled to −78° C., $NH_3$ gas was condensed into the flask under an Ar atmosphere until the liquid volume reached approximately 15 mL. The heptasaccharide benzyl thioether solution was transferred into the liquid $NH_3$. Sodium metal (20 mg, 0.87 mmol) was added under positive Ar gas flow and stirred for 10 minutes. The reaction was quenched at −78° C. by the addition of saturated $NH_4Cl$ solution (0.1 mL) and warmed to room temperature. $N_2$ was bubbled through the reaction mixture to remove excess $NH_3$, and then the solution was concentrated to dryness. The crude material was purified by size exclusion chromatography on a bed of Sephadex G-10 (2.5 cm×8 cm column) by elution with water. The fractions containing product were concentrated to yield the crude heptasaccharide with co-eluting salts (80 mg).

The crude heptasaccharide/salt mixture (80 mg) was dissolved in water (0.8 mL) and methanol (0.4 mL), solid $NaHCO_3$ (40 mg), and acetic anhydride (40 µL) were added. The reaction mixture was stirred for 2 hours then loaded directly onto a Sephadex G-10 column (2.5 cm×8 cm) and eluted with water. Lyophilization of the appropriate fractions gave the desired Moraxella serotype C11 heptasaccharide fragment 52 (15.4 mg).

Synthesis of Serotype C11 Heptamer Conjugates 53, 42 (FIG. 12)

First, a conjugation stock solution of heptasaccharide 40 was prepared as follows. The heptasaccharide 40 (4.9 mg, 3.86 µmol) was dissolved in water (0.6 mL). Hydrazine in water (0.05 M, 60 µL) was added to the reaction mixture, was stirred at room temperature for 1 hour and concentrated in vacuo. The residue was co-evaporated with water (3×1 mL) and redissolved in water (300 µL). A solution of tris(2-carboxyethyl)phosphine (TCEP) in water (39 µL, 0.05 M, 1.95 µmol) was added and stirred for 1 hour. Imject® Conjugation Buffer (Pierce, 300 µL) was added to provide a stock solution for conjugation to KLH and BSA.

To synthesize the KLH conjugate 53, conjugation stock solution of heptasaccharide thiol 40 (140 µL, 0.87 µmol) was added to a solution of maleimide-activated keyhole limpet hemocyanin (Imject® KLH, Pierce, Rockford, Ill.) (5 mg, ~0.43 µmol maleimide) in water (0.5 mL) was added and the resulting solution stirred overnight at room temperature. The reaction mixture was purified by de-salting on D-Salt P-6000 10 mL column (Pierce, Rockford, Ill.). The column was pre-equilibrated with 30 mL of purification buffer (Pierce, Prod. No. 77159), the crude material loaded onto the column and eluted with purification buffer. 1-mL fractions were collected and analyzed for protein content by absorbance at 280 nm ($A_{280}$). Fractions containing protein were combined and lyophilized to give the desired serotype C11 heptamer fragment-KLH conjugate 53.

To synthesize the BSA conjugate 42, conjugation stock solution of heptasaccharide thiol 40 (500 µL, 3.0 µmol) was added to a solution of maleimide-activated bovine serum albumin (Imject® BSA, Pierce, Rockford, Ill.) (5 mg, ~1.5 µmol maleimide) in Imject® Conjugation Buffer (Pierce, 250

µL diluted with water, 250 µL) and the resulting solution stirred for 18 hours at room temperature. The reaction mixture was purified by de-salting on D-Salt P-6000 10 mL column (Pierce, Rockford, Ill.). The column was pre-equilibrated with 30 mL of purification buffer (Pierce, Prod. No. 77159), the crude material loaded onto the column and eluted with purification buffer. 1-mL fractions were collected and analyzed for protein content by absorbance at 280 nm ($A_{280}$). Fractions containing protein were combined and lyophilized to give the desired serotype C11 heptamer fragment-BSA conjugate 42.

Table 3 provides supporting characterization data for selected oligosaccharides and intermediates described in Examples 2-9.

TABLE 3

Characterization data

| Series | Description | compound # | NMR $^1$H | NMR $^{13}$C | Mass Spec Theo. | Mass Spec MALDI |
|---|---|---|---|---|---|---|
| 7mer Core | OBn/Allyl | 45 | ✓ | ✓ | 3175 | 3195 (M + Na$^+$) |
| | OBn/SAc | | | ✓ | 3251 | |
| | OH/SH | 46 | ✓ | ✓ | 1227 | 1251 (M + Na$^+$) |
| Tetra Core | OBn/Allyl | 4 | ✓ | ✓ | 1698 | 1721 (M + Na$^+$) |
| | OBn/SAc | | ✓ | ✓ | 1774 | 1796 (M + Na$^+$) |
| | OH/SH | 5 | ✓ | ✓ | 740 | 763 (M + Na$^+$) |
| A | OBn/Allyl/N$_3$ | 26 | ✓ | ✓ | 3543 | |
| | OBn/SAc/N$_3$ | | ✓ | | 3619 | |
| | OBn/SBn/N$_3$ | | ✓ | | 3664 | 3665 (M + H$^+$) |
| | OH/SH/NH$_2$ | | ✓ | ✓ | 1388 | 1411 (M + Na$^+$) |
| | OH/SH/NHAc | 27 | ✓ | | 1430 | 1496 (M + Ac) |

TABLE 3-continued

Characterization data

| Series | Description | compound # | NMR $^1$H | NMR $^{13}$C | Mass Spec Theo. | Mass Spec MALDI |
|---|---|---|---|---|---|---|
| B7 | OBn/Allyl | 7 | ✓ | ✓ | 2743 | 2764 (M + Na$^+$) |
| | OBn/SAc | | | ✓ | 2819 | 2841 (M + Na$^+$) |
| | OH/SH | 8 | ✓ | ✓ | 1065 | 1090 (M + Na$^+$) |
| B9 | OBn/Allyl | 10 | ✓ | | 3608 | |
| | OBn/SAc | | | ✓ | 3684 | |
| | OH/SH | 11 | ✓ | ✓ | 1389 | 1413 (M + Na$^+$) |
| B11 | OBn/Allyl | 19 | ✓ | ✓ | 4473 | |
| | OBn/SAc | | | ✓ | 4549 | |
| | OH/SH | 20 | ✓ | ✓ | 1713 | 1737 (M + Na$^+$) |
| C11 Hepta Fragment | OBn/Allyl/N$_3$ | 35 | ✓ | ✓ | 3020 | 3043 (M + Na$^+$) |
| | OBn/SAc/N$_3$ | | | ✓ | 3096 | |
| | OBn/SBn/N$_3$ | | | ✓ | 3144 | 3144 (M$^+$) |
| | OH/SH/NH$_2$ | | | ✓ | 1226 | 1249 (M + Na$^+$) |
| | OH/SH/NHAc | 40 | ✓ | | 1268 | 1334 (M + Ac) |
| C11 | OBn/Allyl/N$_3$ | 36 | ✓ | ✓ | 4408 | 4429 (M + Na$^+$) |
| | OBn/SAc/N$_3$ | | | ✓ | 4484 | |
| | OBn/SBn/N$_3$ | | | ✓ | 4532 | 4530 (M$^+$) |
| | OH/SH/NH$_2$ | | | ✓ | 1712 | 1735 (M + Na$^+$) |
| | OH/SH/NHAc | 37 | ✓ | | 1754 | 1819 (M + Ac) |

In Table 2, protein assays were performed according to the method of Bradford, M. *Anal. Biochem.* 1976, 72, 248. Carbohydrate analysis was performed according to the method of Dubois, M. et al *Anal. Chem.* 1956, 28, 350. Maldi analysis was performed using 2,5-dihydroxybenzoic acid as a matrix. Copy numbers were determined by the formula: copy number=[Maldi$_{(observed)}$−76,000$_{(Maldi\ of\ BSA\ alone)}$]/Antigen MW. Carbohydrate content in KLH sample extrapolated from BSA using the formula: KLH carbohydrate content=BSA carbohydrate content/2.65.

Table 4 provides supporting characterization data for the antigen conjugates described in Examples 2-9.

TABLE 4 characterization data

| Conjugate # | Description | Protein Assay BSA (mg/mL) | Protein Assay KLH (mg/mL) | Carb. Assay Hexose (mg/mL) | MALDI | Antigen MW | Avg. Copy No. | % Carbohydrate MALDI | % Carbohydrate Carb. Assay | % Carbohydrate Sample |
|---|---|---|---|---|---|---|---|---|---|---|
| 50 | Tetra Core-BSA | 1.11 | | 0.33 | 83,540 | 740 | 10.2 | 9% | 30% | |
| 49 | Tetra Core-KLH | | 1.34 | 0.12 | | 740 | | | 9% | 3% |
| 41 | B7-BSA | 0.91 | | 0.5 | 89,500 | 1065 | 12.7 | 15% | 55% | |
| 9 | B7-KLH | | 1.43 | 0.13 | | 1065 | | | 9% | 6% |
| 48 | 7mer Core-BSA | 1.16 | | 0.35 | 88,480 | 1226 | 10.2 | 14% | 30% | |
| 47 | 7mer Core-KLH | | 1.19 | 0.1 | | 1226 | | | 8% | 5% |
| 40 | B9-BSA | 0.98 | | 0.36 | 89,460 | 1389 | 9.7 | 15% | 37% | |
| 12 | B9-KLH | | 1.19 | 0.12 | | 1389 | | | 10% | 6% |
| 22 | B11-BSA | 1.09 | | 0.59 | 102,600 | 1715 | 15.5 | 26% | 54% | |
| 21 | B11-KLH | | 1.14 | 0.14 | | 1715 | | | 12% | 10% |
| 29 | A-BSA | 1.55 | | 0.6 | 94,309 | 1430 | 12.8 | 19% | 39% | |
| 28 | A-KLH | | 1.36 | 0.19 | | 1430 | | | 14% | 7% |
| 42 | C11 Hepta Core (Trunc C)-BSA | 1.4 | | 0.45 | 93,487 | 1267 | 13.8 | 19% | 32% | |
| 53 | C11 Hepta Core (Trunc C)-KLH | | 1.2 | 0.12 | | 1267 | | | 10% | 7% |
| 39 | C11-BSA | 1.52 | | 0.47 | 91,750 | 1753 | 9.0 | 17% | 31% | |
| 38 | C11-KLH | | 1.2 | 0.16 | | 1753 | | | 13% | 6% |

In Table 5, protein assays, Maldi analysis, copy numbers, and carbohydrate content were determined as described above with reference to Table 4.

Example 10

Serum Antibody Production and Purification

Antisera to each antigen-KLH conjugate were raised in New Zealand white rabbits by four subcutaneous injections of antigen-KLH conjugate over 13 weeks. A pre-immune bleed generated 5 mL of baseline serum from each rabbit. The prime injection (10 µg antigen equivalent) was given as an emulsion in complete Freund's adjuvant (CFA). Subsequent injections (5 µg antigen equivalent) were given at three week intervals in incomplete Freund's adjuvant (IFA). Rabbits were bled every two weeks commencing one week after the third immunization. Approximately 25-30 mL of serum per rabbit was generated for each bleeding event, and was aliquoted into 1-mL aliquots and frozen at −80° C. Serum was analyzed by ELISA against the corresponding antigen-BSA conjugate as described in Example 11. Affinity purification of antisera was conducted with serum from the third bleed from each rabbit.

Affinity purification of antisera was conducted with serum from the third bleed from each rabbit. Affinity purification was carried out by coupling of antigen-BSA conjugates to CNBr-activated Sepharose 4B. Briefly, CNBr-activated Sepharose 4B (0.8 g, 2.5 ml of final gel volume) was washed and re-swelled on a sintered glass filter with 1 mM HCl, then coupling buffer (0.1 M NaHCO$_3$, 0.25M NaCl, pH 8.5). Antigen-BSA conjugate (1 mg) was dissolved in coupling buffer, mixed with the gel suspension and incubated overnight at 40° C. Unreacted active groups were capped with glycine buffer (0.2M, pH 8.1) and excess adsorbed conjugated was washed away with coupling buffer, then acetate buffer (0.1 M containing 0.5M NaCl, pH 4.3). The column was equilibrated with phosphate buffered saline (PBS), pH7.7.

Antisera were affinity purified by diluting clear antiserum (5 mL) 1:1 with PBS pH7.7 and applying the diluted antisera to the affinity column at the rate of 0.3ml/min and absorbance of eluate was monitored at 280 nm. Unbound material (flow through) was collected and analyzed by ELISA using the general ELISA procedure. The column was washed with PBS until A280 reached baseline. Bound antibodies were eluted with 0.2M glycine (pH 1.85) into one fraction until the A280 returned to baseline. Fractions were neutralized with 1M Tris-HCl, pH 8.5 immediately after collection and the OD at 280 nm was determined. ELISA analysis was conducted using the corresponding antigen-BSA conjugate according to the general ELISA protocol in Example 11 to confirm the recovered antibody and the removal of all the antibodies from the original serum. Antibody quantification was determined by A280 reading of the antibody (a small amount was diluted to give an OD value of about 1.0) and this value was divided by the extinction coefficient of IgG, 1.4, to give mg/mL. The solutions were concentrated to ~1-2 mg/mL, dialyzed against PBS with 0.02% sodium azide, aliquoted and frozen at −80° C.

Example 11

ELISA Preparation and Protocol

An oligosaccharide-BSA conjugate solution was prepared by dissolving the conjugate in carbonate buffer (1.59 g Na$_2$CO$_3$, 2.93 g NaHCO$_3$, 0.20 g NaN$_3$, dissolved and diluted to 1 L in H$_2$O, final pH 9.5) at a concentration of 5-10 µg/mL. COSTAR flat bottom EIA 8-well strips were incubated with oligosaccharide-BSA conjugate solution (100 µL per well) for 24 hours in a humidity chamber to coat the well surfaces. Coating solution was removed, each well was rinsed twice with water, and dried on a paper towel. Blocking solution (0.1% BSA in PBS with 0.02% thimerosal, 200 µL) was added to each well and incubated for 2 hours in a humidity chamber. Blocking solution was removed; each well was rinsed with water and dried on a paper towel.

Serum samples were prepared by 1:5 serial dilutions starting from a 1:1,000 dilution of serum in 0.1% BSA in PBS with 0.02% thimerosal. Diluted serum (100 µL) was added to each well and incubated for 2 hours at room temperature in a humidity chamber. The serum solution was removed, the wells were rinsed twice with water and dried on a paper towel. Goat anti-rabbit-HRP conjugate solution (100 µL/well) was added and incubated for 2 hours at room temperature in a humidity chamber. The HRP-conjugate solution was removed, and wells were washed three times with PBS/0.02% thimerosal/0.05% tween-20, twice with water, and dried on a paper towel. TMB solution (100 µL/well) was added and developed at room temperature. The reaction was stopped by the addition of 1N HCl (100 µL/well) and the wells were read immediately at A450 (absorbance at 450 nm). The titer of the test serum was designated as the dilution which gave an optical density (OD$_{450}$) reading of 0.1 above background.

Example 12

Rabbit Immunogenicity of Synthetic Antigen-KLH Conjugates by ELISA

FIGS. 13A-13H depict ELISA results showing IgG IgG antibody titers as a function of antibody-antigen complex absorption (OD$_{450}$) at 3 serum dilutions of immune sera obtained from 3 succesive bleeds (pre-imune[1 st] bleed, and final bleed) in rabbits (n=2) immunized with antigen-KLH conjugates corresponding to (A) Serotype A-KLH 28; (B) Serotype B7-KLH 9; (C) Serotype B9-KLH 12; (D) Serotype B11-KLH 21; (E) Serotype C11-decamer-KLH 38; (F) Serotype C11-heptamer-KLH 53; (G) heptamer core-KLH 47; and (H) tetramer core-KLH 49. In each case, the antisera were incubated on ELISA plates adsorbed with their corresponding BSA conjugate, specifically (A) Serotype A-BSA 29; (B) Serotype B7-BSA 41; (C) Serotype B9-BSA 40; (D) Serotype B11-decamer-BSA 22; (E) Serotype C11-decamer-BSA 39; (F) Serotype C11-heptamer-BSA 42; (G) heptamer core-BSA 48; and (H) tetramer core-BSA 50 as described in the ELISA protocol above (Example 11).

FIGS. 13A-13H show that each antiserum was able to identify its corresponding BSA conjugate, thereby reflecting Ag-selective immune responses.

Example 13

Specificity and Cross-Reactivity of Antisera to Different Antigens by ELISA

FIGS. 14A-14D depict specificity and cross-reactivity of antisera to different synthetic *Moraxella* LOS oligosaccharides. Antisera from rabbits immunized with the indicated antigen-KLH conjugates corresponding to (left to right) KLH alone, tetramer core-KLH 49, hexamer core (B7)-KLH 9, heptamer core-KLH 47, Serotype B11-KLH 21, Serotype A-KLH 28, and Serotype C11-decamer-KLH 38 were incubated with ELISA plates adsorbed with antigen-BSA conjugates, including (A) Serotype A-BSA 29; (B) Serotype B11-BSA 22; (C) Serotype C11-decamer -BSA 39; and (D) Serotype C11-heptamer fragment-BSA 48. The IgG titers are measured a function of antibody-antigen complex absorption ($OD_{450}$) at the indicated serum dilutions. The data reflect average $OD_{450}$ values measured from sera from two rabbits, whereby total $OD_{450}$ is measured by subtracting the background $OD_{450}$ measured from KLH alone.

FIGS. 14A-14D show significant cross-reactivity for the core structures against the full length structures, indicating the potential for single valent vaccine(s) effective against all serotypes.

Example 14

Protocol Summary—*M. catarrhalis* Serum Bactericidal Assay (SBA)

The following procedure was performed to determine the neutralizing of activity of serum against *M.catarrhalis*. Serum was sterile filtered prior to assay and confirmed to be free of contaminates. Serum samples were serially diluted 1:5 by adding 20 ul serum to 80 µl PBS containing 0.1% gelatin. 50 µl of undiluted, 1:5 dilution, 1:25, and 1:125 dilution of immune serum was added to 96 well plates. 50 µl of undiluted and 1:5 dilution pre-immune serum was added to 96 well plates. 0.25 µg/ml Ciprofloxacin was used as a positive control.

Samples and controls were tested in quadruplicate. 20 µl Rabbit serum (Sigma) as a complement source at a 1:8 dilution in PBS was added to each well. A bacterial suspension of *M. catarrhalis* (Type A, ATCC 25238; Type B, CCUG 26937 or Type C, CCUG 26404) made so that the suspension equal to ~0.100 absorbance which is ~1.6 $10^8$ CFU/mL. The suspension was diluted 1:100 to equal $1.6 \times 10^6$ CFU/ml (add 20 µl bacteria to 1.980 mL BHI media). The suspension was diluted 1:100 again (add 100 µl 1:100 dilution to 9.9 mL BHI media), then add 30 µl per well for $5 \times 10^2$ CFU/well.

30 µl of *M. catarrhalis* was added to each well at a density of 500 CFU/well. 96 well plates were incubated at 37° C. with 5% $CO_2$ for 1 hour. 50 µl of each well of the 96 well plate was plated onto chocolate agar. Chocolate agar plates were incubated at 37° C. with 5% $CO_2$ overnight. Colonies were counted and recorded.

TABLE 6

Serotype A bactericidal activity data (ATCC 25238)

| Pre-immune Serum | Dilution | Average CFU/well | Immune Serum | Dilution | Average CFU/well | % Killing |
|---|---|---|---|---|---|---|
| KLH Carrier | no dilution | 211 | KLH Carrier | no dilution | 313.5 | 0.0 |
| | 1:5 | 216 | | 1:5 | 163.5 | 22.5 |
| | | | | 1:25 | 239.5 | 0.0 |
| | | | | 1:125 | 338.5 | 0.0 |
| TetraCore (49) | no dilution | 493 | TetraCore (49) | no dilution | 14 | 97.2 |
| | 1:5 | 310.5 | | 1:5 | 283 | 42.6 |
| | | | | 1:25 | 236 | 52.1 |
| | | | | 1:125 | 345 | 30.0 |
| 7mer Core (47) | no dilution | 394 | 7mer Core (47) | no dilution | 3.5 | 99.1 |
| | 1:5 | 486.5 | | 1:5 | 79.5 | 79.8 |
| | | | | 1:25 | 393 | 0.3 |
| | | | | 1:125 | 194.5 | 50.6 |
| ST A (28) | no dilution | 254.5 | ST A (28) | no dilution | 0 | 100.0 |
| | 1:5 | 270.5 | | 1:5 | 0 | 100.0 |
| | | | | 1:25 | 3.5 | 98.6 |
| | | | | 1:125 | 74 | 70.9 |

TABLE 6-continued

Serotype A bactericidal activity data (ATCC 25238)

| Pre-immune Serum | Dilution | Average CFU/well | Immune Serum | Dilution | Average CFU/well | % Killing |
|---|---|---|---|---|---|---|
| ST B11 (21) | no dilution | 501.5 | ST B11 (21) | no dilution | 0.5 | 99.9 |
| | 1:5 | 332 | | 1:5 | 13.5 | 97.3 |
| | | | | 1:25 | 214 | 57.3 |
| | | | | 1:125 | 249 | 50.3 |
| Cipro | 0.25 µg/ml | 79.5 | | | | |
| *M. catarrhalis* | no treatment | 368 | | | | |

TABLE 7

Serotype A bacteridical activity data- (ATCC 25238)

| Pre Immune Serum | Comparative Basis | Average CFU/well | Immune Serum | Dilution | Average CFU/well | % Killing |
|---|---|---|---|---|---|---|
| KLH Carrier | Neg Control | 298 | KLH Carrier | 1:5 | 220 | 26% |
| | | | | 1:20 | 268 | 10% |
| | | | | 1:80 | 295 | 1% |
| | | | | 1:160 | 294 | 1% |
| Tetra Core (49) | Neg Control | 287 | TetraCore (49) | 1:5 | 2.25 | 99% |
| | | | | 1:20 | 253 | 12% |
| | | | | 1:80 | 226 | 21% |
| | | | | 1:160 | 213 | 26% |
| 7mer Core (47) | Neg Control | 287 | 7mer Core (47) | 1:5 | 1.5 | 99% |
| | | | | 1:20 | 230 | 20% |
| | | | | 1:80 | 224 | 22% |
| | | | | 1:160 | 280 | 2% |
| ST A (28) | Neg Control | 287 | ST A (28) | 1:5 | 0.25 | 100% |
| | | | | 1:20 | 32 | 89% |
| | | | | 1:80 | 103 | 64% |
| | | | | 1:160 | 184 | 36% |
| ST B11 (21) | Neg Control | 173 | ST B11 (21) | 1:5 | 0 | 100% |
| | | | | 1:20 | 116 | 33% |
| | | | | 1:80 | 145 | 16% |
| | | | | 1:160 | 143 | 17% |
| ST B7 (9) | Neg Control | 154 | ST B7 (9) | 1:5 | 17 | 89% |
| | | | | 1:20 | 130 | 16% |
| | | | | 1:80 | 167 | -8% |
| | | | | 1:160 | 152 | 1% |
| ST B9 (12) | Neg Control | 154 | ST B9 (12) | 1:5 | 0.5 | 100% |
| | | | | 1:20 | 125 | 19% |
| | | | | 1:80 | 187 | -21% |
| | | | | 1:160 | 133 | 14% |
| C 11 Hepta Core (53) | Neg Control | 284 | C 11 HeptaCore (53) | 1:5 | 0 | 100% |
| | | | | 1:20 | 298 | -5% |
| | | | | 1:80 | 302 | -6% |
| | | | | 1:160 | 285 | 0% |
| ST C (38) | Neg Control | 284 | ST C (38) | 1:5 | 4.5 | 98% |
| | | | | 1:20 | 6 | 98% |
| | | | | 1:80 | 357 | -26% |
| | | | | 1:160 | 350 | -23% |

TABLE 8

Serotype B bactericidal activity data (CCUG 26397)

| Pre-Immune Serum | Comparative Basis | Average CFU/well | Immune Serum | Dilution | Average CFU/well | % Killing |
|---|---|---|---|---|---|---|
| KLH Carrier | Neg Control | 304 | KLH Carrier | 1:5 | 170 | 44% |
| | | | | 1:20 | 299 | 2% |
| | | | | 1:80 | 174 | 43% |
| | | | | 1:160 | 273 | 10% |

TABLE 8-continued

Serotype B bactericidal activity data (CCUG 26397)

| Pre-Immune Serum | Comparative Basis | Average CFU/well | Immune Serum | Dilution | Average CFU/well | % Killing |
|---|---|---|---|---|---|---|
| Tetra Core (49) | Neg Control | 304 | Tetra Core (49) | 1:5 | 87 | 71% |
| | | | | 1:20 | 290 | 5% |
| | | | | 1:80 | 302 | 1% |
| | | | | 1:160 | 294 | 3% |
| 7mer Core (47) | Neg Control | 650 | 7mer Core (47) | 1:5 | 177 | 73% |
| | | | | 1:20 | 650 | 0% |
| | | | | 1:80 | 650 | 0% |
| | | | | 1:160 | 650 | 0% |
| ST A (28) | Neg Control | 650 | ST A (28) | 1:5 | 89 | 86% |
| | | | | 1:20 | 650 | 0% |
| | | | | 1:80 | 650 | 0% |
| | | | | 1:160 | 650 | 0% |
| ST B11 (21) | Neg Control | 337 | ST B11 (21) | 1:5 | 60 | 82% |
| | | | | 1:20 | 304 | 10% |
| | | | | 1:80 | 364 | −8% |
| | | | | 1:160 | 261 | 23% |
| ST B7 (9) | Neg Control | 263 | ST B7 (9) | 1:5 | 5 | 98% |
| | | | | 1:20 | 277 | −5% |
| | | | | 1:80 | 264 | 0% |
| | | | | 1:160 | 127 | 52% |
| ST B9 (12) | Neg Control | 421 | ST B9 (12) | 1:5 | 0 | 100% |
| | | | | 1:20 | 136 | 68% |
| | | | | 1:80 | 299 | 29% |
| | | | | 1:160 | 351 | 17% |
| C 11 HeptaCore (53) | Neg Control | 421 | C 11 HeptaCore (53) | 1:5 | 3 | 99% |
| | | | | 1:20 | 317 | 25% |
| | | | | 1:80 | 323 | 23% |
| | | | | 1:160 | 363 | 14% |
| ST C (38) | Neg Control | 421 | ST C (38) | 1:5 | 5 | 99% |
| | | | | 1:20 | 346 | 18% |
| | | | | 1:80 | 295 | 30% |
| | | | | 1:160 | 303 | 28% |

TABLE 9

Serotype C Killing - *Moraxella Catarrhalis* CCUG 26404

| Pre-Immune Serum | Comparative Basis | Average CFU/well | Immune Serum | Dilution | Average CFU/well | % Killing |
|---|---|---|---|---|---|---|
| KLH Carrier | Neg Control | 263 | KLH Carrier | 1:5 | 146 | 44% |
| | | | | 1:20 | 243 | 8% |
| | | | | 1:80 | 227 | 14% |
| | | | | 1:160 | 282 | −7% |
| Tetra Core (49) | Neg Control | 263 | TetraCore (49) | 1:5 | 46 | 83% |
| | | | | 1:20 | 207 | 21% |
| | | | | 1:80 | 161 | 39% |
| | | | | 1:160 | 213 | 19% |
| 7mer Core (47) | Neg Control | 650 | 7mer Core (47) | 1:5 | 18 | 97% |
| | | | | 1:20 | 650 | 0% |
| | | | | 1:80 | 650 | 0% |
| | | | | 1:160 | 650 | 0% |
| ST A (28) | Neg Control | 650 | ST A (28) | 1:5 | 3.5 | 99% |
| | | | | 1:20 | 650 | 0% |
| | | | | 1:80 | 650 | 0% |
| | | | | 1:160 | 650 | 0% |
| ST B11 (21) | Neg Control | 650 | ST B11 (21) | 1:5 | 4 | 99% |
| | | | | 1:20 | 650 | 0% |
| | | | | 1:80 | 650 | 0% |
| | | | | 1:160 | 650 | 0% |
| ST B7 (9) | Neg Control | 650 | ST B7 (9) | 1:5 | 53 | 92% |
| | | | | 1:20 | 650 | 0% |
| | | | | 1:80 | 650 | 0% |
| | | | | 1:160 | 650 | 0% |
| ST B9 (12) | Neg Control | 428 | ST B9 (12) | 1:5 | 97 | 77% |
| | | | | 1:20 | 337 | 21% |
| | | | | 1:80 | 262 | 39% |
| | | | | 1:160 | 451 | −5% |

TABLE 9-continued

Serotype C Killing - *Moraxella Catarrhalis* CCUG 26404

| Pre-Immune Serum | Comparative Basis | Average CFU/well | Immune Serum | Dilution | Average CFU/well | % Killing |
|---|---|---|---|---|---|---|
| C 11 HeptaCore (53) | Neg Control | 428 | C 11 HeptaCore (53) | 1:5 | 7 | 98% |
| | | | | 1:20 | 209 | 51% |
| | | | | 1:80 | 309 | 28% |
| | | | | 1:160 | 319 | 25% |
| ST C (38) | Neg Control | 428 | ST C (38) | 1:5 | 3 | 99% |
| | | | | 1:20 | 196 | 54% |
| | | | | 1:80 | 487 | −14% |
| | | | | 1:160 | 338 | 21% |

It is intended that the foregoing detailed description be regarded as illustrative rather than limiting, and that it be understood that it is the following claims, including all equivalents, that are intended to define the spirit and scope of this invention.

The invention claimed is:

1. A synthetic oligosaccharide 1a or 1b:

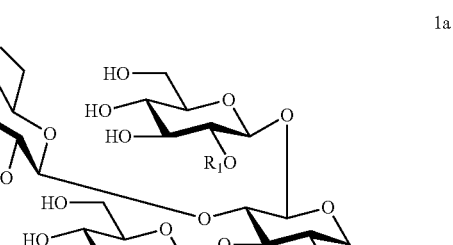

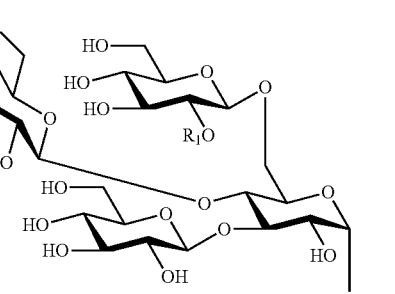

where $R^1$ and $R^2$ are selected from the following table

| $R^1$ | $R^2$ |
|---|---|
| αGlc(1-2) | H |
| | αGlc(1-2) |
| | βGal(1-4)αGlc(1-2) |
| | αGal(1-4)βGal(1-4)αGlc(1-2) |
| H | αGlc(1-2) |
| | βGal(1-4)αGlc(1-2) |
| | αGal(1-4)βGal(1-4)αGlc(1-2) |
| βGal(1-4)αGlc(1-2) | H |
| | αGlc(1-2) |
| | βGa1(1-4)αGlc(1-2) |
| | αGal(1-4)βGal(1-4)αGlc(1-2) |

-continued

| R¹ | R² |
|---|---|
| αGal(1-4)βGal(1-4)αGlc(1-2) | H |
| | αGlc(12) |
| | βGal(1-4)αGlc(1-2) |
| | αGal(1-4)βGal(1-4)αGlc(1-2) |

X is H or a protecting group, L is a linker, and Y is H or a carrier.

2. The oligosaccharide of claim 1, wherein R¹ is H and R² is α-Glc(1→2).

3. The oligosaccharide of claim 1, wherein R¹ is H and R² is β-Gal-(1→4)-α-Glc 1→2).

4. The oligosaccharide of claim 1, wherein R¹ is H and R² is α-Gal-(1→4)-β-Gal-(1→4)-α-Glc(1→2).

5. The oligosaccharide of claim 1, wherein R¹ is α-Glc-(1→2) and R² is H.

6. The oligosaccharide of claim 1, wherein R¹ is α-Glc-(1→2) and R² is α-Glc-(1→2).

7. The oligosaccharide of claim 1, wherein R¹ is α-Glc-(1→2) and R² is β-Gal-(1→4)-α-Glc(1→2).

8. The oligosaccharide of claim 1, wherein R¹ is α-Glc-(1→2) and R² is α-Gal(1→4)-β-Gal(1→4)-α-Glc(1→2).

9. The oligosaccharide of claim 1, wherein R¹ is β-Gal-(1→4)-α-Glc(1→2) and R² is H.

10. The oligosaccharide of claim 1, wherein R¹ is β-Gal-(1→4)-α-Glc(1→2) and R² is α-Glc(1→2).

11. The oligosaccharide of claim 1, wherein R¹ is β-Gal-(1→4)-α-Glc(1→2) and R² is α-Gal-(1→4)-α-Glc(1→2).

12. The oligosaccharide of claim 1, wherein R¹ is β-Gal-(1→4)-α-Glc(1→2) and R² is α-Gal-(1→4)-β-Gal-(1→4)-α-Glc(1→2).

13. The oligosaccharide of claim 1, wherein R¹ is α-Gal-(1→4)-β-Gal-(1→4)-α-Glc(1→2) and R² is H.

14. The oligosaccharide of claim 1, wherein R¹ is α-Gal-(1→4)-β-Gal-(1→4)-α-Glc(1→2) and R² is α-Glc(1→2).

15. The oligosaccharide of claim 1, wherein R¹ is α-Gal-(1→4)-β-Gal-(1→4)-α-Glc(1→2) and R² is β-Gal-(1→4)-α-Glc(1→2).

16. The oligosaccharide of claim 1, wherein R¹ is α-Gal-(1→4)-β-Gal-(1→4)-α-Glc(1→2) and R² is α-Gal-(1→4)-β-Gal-(1→4)-α-Glc(1→2).

17. The oligosaccharide of claim 1, wherein L is an alkylene thiol linker.

18. The synthetic oligosaccharide of claim 1, wherein Y is a carrier selected from the group consisting of proteins, peptides, lipids, polymers, dendrimers, virosomes, and virus-like particles or combination thereof.

19. The synthetic oligosaccharide of claim 18, wherein the carrier is a carrier protein.

20. The synthetic oligosaccharide of claim 19, wherein the carrier protein is selected from the group consisting of bacterial toxoids, toxins, exotoxins, and nontoxic derivatives thereof 21. The synthetic oligosaccharide of claim 20, wherein the carrier protein is selected from the group consisting of tetanus toxoid, tetanus toxin Fragment C, diphtheria toxoid, CRM, cholera toxoid, Staphylococcus aureus exotoxins or toxoids, Escherichia coli heat labile enterotoxin, Pseudomonas aeruginosa exotoxin A, genetically detoxified variants thereof; bacterial outer membrane proteins, serotype B outer membrane protein complex (OMPC), outer membrane class 3 porin (rPorB), porins; keyhole limpet hemocyanine (KLH), hepatitis B virus core protein, thyroglobulin, albumins, and ovalbumin; pneumococcal surface protein A (PspA), pneumococcal adhesin protein (PsaA); purified protein derivative of tuberculin (PPD); transferrin binding proteins, peptidyl agonists of TLR-5; and derivatives and/or combinations of the above carriers.

22. The synthetic oligosaccharide of claim 21, wherein the carrier protein is selected from the group consisting of CRM 197, Neisseria meningitidis, bovine serum albumin (BSA), human serum albumin (HSA), poly(lysine:glutamic acid), flagellin of motile bacteria, and derivatives and/or combinations thereof.

23. The synthetic oligosaccharide of claim 21, wherein the carrier protein is selected from the group consisting of tetanus toxoid, CRM 197, and OMPC.

24. A composition comprising a synthetic oligosaccharide of claim 1 and a pharmaceutically acceptable vehicle.

25. The composition of claim 24, comprising a second oligosaccharide 1c or 1d:

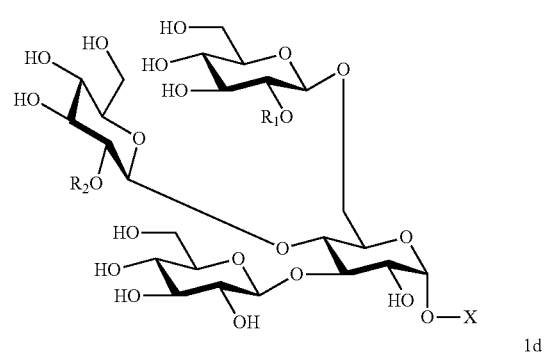

1c

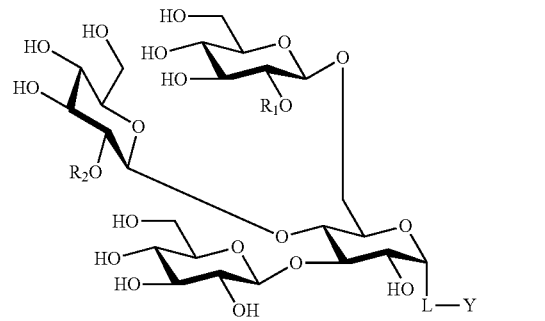

1d where R¹ and R² are selected from the following table

| R1 | R2 |
|---|---|
| αGlc(1-2) | H |
| | αGlc(1-2) |
| | βGal(1-4)aGlc(1-2) |
| | αGal(1-4))βGal(1-4)αGlc(1-2) |
| | αGlcNAc(1-2) |
| | βGal(1-4)αGlcNAc(1-2) |
| | αGal(1-4)βGal(1-4)αGlcNAc(1-2) |
| H | H |
| | αGlc(1-2) |
| | βGal(1-4)αGlc(1-2) |
| | αGal(1-4)βGal(1-4)αGlc(1-2) |
| | αGlcNAc(1-2) |
| | βGal(1-4)αGlcNAc(1-2) |
| | αGal(1-4)βGal(1-4)αGlcNAc(1-2) |

-continued

| R1 | R2 |
|---|---|
| βGal(1-4)αGlc(1-2) | H |
|  | αGlc(1-2) |
|  | βGal(1-4)αGlc(1-2) |
|  | αGal(1-4)βGal(1-4)αGlc(1-2) |
|  | αGlcNAc(1-2) |
|  | βGal(1-4)αGlcNAc(1-2) |
|  | αGal(1-4)βGal(1-4)αGlcNAc(1-2) |
| αGal(1-4)βGal(1-4)αGlc(1-2) | H |
|  | αGlc(1-2) |
|  | βGal(1-4)αGlc(1-2) |
|  | αGal(1-4)βGal(1-4)αGlc(1-2) |
|  | αGlcNAc(1-2) |
|  | βGal(1-4)αGlcNAc(1-2) |
|  | αGal(1-4)βGal(1-4)αGlcNAc(1-2) |

X is H or a protecting group, L is a linker, and Y is H or a carrier.

* * * * *